United States Patent
Wensley et al.

(10) Patent No.: US 10,034,988 B2
(45) Date of Patent: Jul. 31, 2018

(54) METHODS AND DEVICES FOR COMPOUND DELIVERY

(71) Applicant: FONTEM HOLDINGS 1 B.V., Amsterdam (NL)

(72) Inventors: Martin Wensley, Los Gatos, CA (US); Michael Hufford, Chapel Hill, NC (US); Jeffrey Williams, Draper, UT (US); Peter Lloyd, Walnut Creek, CA (US)

(73) Assignee: FONTEM HOLDINGS I B.V., Amsterdam (NL)

( * ) Notice: Subject to any disclaimer, the term of this patent is extended or adjusted under 35 U.S.C. 154(b) by 206 days.

(21) Appl. No.: 14/168,338

(22) Filed: Jan. 30, 2014

(65) Prior Publication Data

US 2014/0144429 A1     May 29, 2014

Related U.S. Application Data

(63) Continuation of application No. PCT/US2013/072426, filed on Nov. 27, 2013.
(Continued)

(51) Int. Cl.
 *A61M 11/00*     (2006.01)
 *A61M 11/04*     (2006.01)
(Continued)

(52) U.S. Cl.
 CPC .......... *A61M 11/041* (2013.01); *A61M 15/06* (2013.01); *A61M 16/0066* (2013.01);
(Continued)

(58) Field of Classification Search
 CPC ...... A61M 15/0065; A61M 15/0003–15/0001; A61M 15/00–15/001; A61M 15/004–15/0043; A61M 15/0045–15/0051; A61M 15/0068–15/0083; A61M 15/0086–15/0088;
(Continued)

(56) References Cited

U.S. PATENT DOCUMENTS 2,057,353 A * 10/1936 Whittemore ............. 128/203.27
2,415,748 A     2/1947 Lowell
(Continued)

FOREIGN PATENT DOCUMENTS

CN     1127983 A     7/1996
CN     2648836 Y    10/2004
(Continued)

OTHER PUBLICATIONS

U.S. Appl. 14/092,405, filed Nov. 27, 2013, Wensley et al.
(Continued)

*Primary Examiner* — Todd J Scherbel
*Assistant Examiner* — Ned T Heffner
(74) *Attorney, Agent, or Firm* — Perkins Coie LLP; Kenneth H. Ohriner

(57) ABSTRACT

Provided herein are methods and devices, systems for delivering one or more compounds to a subject. Also described herein are methods and devices for transitioning a smoker to an electronic nicotine delivery device and for smoking or nicotine cessation.

18 Claims, 26 Drawing Sheets

Related U.S. Application Data

(60) Provisional application No. 61/887,045, filed on Oct. 4, 2013, provisional application No. 61/831,992, filed on Jun. 6, 2013, provisional application No. 61/794,601, filed on Mar. 15, 2013, provisional application No. 61/730,738, filed on Nov. 28, 2012.

(51) Int. Cl.
*A61M 15/06* (2006.01)
*A61M 16/00* (2006.01)

(52) U.S. Cl.
CPC .............. *A61M 2016/0021* (2013.01); *A61M 2205/8206* (2013.01); *A61M 2206/14* (2013.01)

(58) Field of Classification Search
CPC .......... A61M 15/0091–15/0098; A61M 15/06; A61M 15/08–15/085; A61M 2015/008; A61M 2016/0021; A24F 47/002; A24F 13/04; A24F 1/28; A24F 47/00; A24F 47/04; A24F 47/28; A24F 47/004; A24F 47/008; A61K 8/97
USPC ............. 128/200.11–200.16, 200.24, 200.26, 128/202.21, 203.12, 203.23, 203.24, 128/204.13, 204.18, 204.21; 131/270–273
See application file for complete search history.

(56) References Cited

U.S. PATENT DOCUMENTS

| | | | |
|---|---|---|---|
| 4,106,503 A | 8/1978 | Rosenthal et al. | |
| 4,243,605 A | 1/1981 | Eisenhardt, Jr. et al. | |
| 4,446,862 A * | 5/1984 | Baum et al. ............. | 128/203.15 |
| 4,735,217 A * | 4/1988 | Gerth .................... | A24F 47/008 |
| | | | 128/203.17 |
| 4,922,901 A | 5/1990 | Brooks et al. | |
| 4,947,874 A | 8/1990 | Brooks et al. | |
| 4,947,875 A | 8/1990 | Brooks et al. | |
| 4,953,572 A | 9/1990 | Rose et al. | |
| 5,015,741 A | 5/1991 | Osdene et al. | |
| 5,060,671 A | 10/1991 | Counts et al. | |
| 5,093,894 A | 3/1992 | Deevi et al. | |
| 5,224,498 A | 7/1993 | Deevi et al. | |
| 5,228,460 A | 7/1993 | Sprinkel et al. | |
| 5,249,586 A | 10/1993 | Morgan et al. | |
| 5,261,423 A | 11/1993 | Gaudlitz et al. | |
| 5,269,327 A | 12/1993 | Counts et al. | |
| 5,322,075 A | 6/1994 | Deevi et al. | |
| 5,353,813 A | 10/1994 | Deevi et al. | |
| 5,369,723 A | 11/1994 | Counts et al. | |
| 5,372,148 A | 12/1994 | Mccafferty et al. | |
| 5,388,594 A | 2/1995 | Counts et al. | |
| 5,468,936 A | 11/1995 | Deevi et al. | |
| 5,479,948 A | 1/1996 | Counts et al. | |
| 5,487,378 A * | 1/1996 | Robertson et al. ....... | 128/200.16 |
| 5,497,763 A | 3/1996 | Lloyd et al. | |
| 5,498,850 A | 3/1996 | Das | |
| 5,498,855 A | 3/1996 | Deevi et al. | |
| 5,505,214 A | 4/1996 | Collins et al. | |
| 5,507,277 A | 4/1996 | Rubsamen et al. | |
| 5,522,385 A | 6/1996 | Lloyd et al. | |
| 5,530,225 A | 6/1996 | Hajaligol | |
| 5,544,646 A | 8/1996 | Lloyd et al. | |
| 5,573,692 A | 11/1996 | Das et al. | |
| 5,591,368 A | 1/1997 | Fleischhauer et al. | |
| 5,613,504 A | 3/1997 | Collins et al. | |
| 5,613,505 A | 3/1997 | Campbell et al. | |
| 5,649,554 A | 7/1997 | Sprinkel et al. | |
| 5,659,656 A | 8/1997 | Das | |
| 5,665,262 A | 9/1997 | Hajaligol et al. | |
| 5,666,977 A * | 9/1997 | Higgins ................ | A24F 47/008 |
| | | | 128/200.14 |
| 5,692,291 A | 12/1997 | Collins et al. | |
| 5,692,525 A | 12/1997 | Counts et al. | |
| 5,692,526 A | 12/1997 | Adams et al. | |
| 5,718,222 A | 2/1998 | Lloyd et al. | |
| 5,730,158 A | 3/1998 | Collins et al. | |
| 5,743,251 A * | 4/1998 | Howell et al. ........... | 128/200.14 |
| 5,750,964 A | 5/1998 | Counts et al. | |
| 5,778,897 A | 7/1998 | Nordlicht | |
| 5,816,263 A | 10/1998 | Counts et al. | |
| 5,865,185 A | 2/1999 | Collins et al. | |
| 5,894,841 A * | 4/1999 | Voges ................... | A24F 47/008 |
| | | | 128/200.14 |
| 5,915,387 A | 6/1999 | Baggett et al. | |
| 5,934,289 A | 8/1999 | Watkins et al. | |
| 5,954,979 A | 9/1999 | Counts et al. | |
| 5,957,124 A | 9/1999 | Lloyd et al. | |
| 5,960,792 A | 10/1999 | Lloyd et al. | |
| 5,971,951 A | 10/1999 | Ruskewicz | |
| 5,988,176 A | 11/1999 | Baggett et al. | |
| 6,026,820 A | 2/2000 | Baggett et al. | |
| 6,040,560 A | 3/2000 | Fleischhauer et al. | |
| 6,053,176 A | 4/2000 | Adams et al. | |
| 6,062,213 A | 5/2000 | Fuisz et al. | |
| 6,070,575 A | 6/2000 | Gonda et al. | |
| 6,116,237 A * | 9/2000 | Schultz et al. .......... | 128/203.15 |
| 6,116,247 A | 9/2000 | Banyasz et al. | |
| 6,125,853 A | 10/2000 | Susa et al. | |
| 6,131,570 A | 10/2000 | Schuster et al. | |
| 6,155,268 A | 12/2000 | Takeuchi | |
| 6,192,882 B1 | 2/2001 | Gonda | |
| 6,196,218 B1 | 3/2001 | Voges | |
| 6,230,706 B1 | 5/2001 | Gonda et al. | |
| 6,234,167 B1 | 5/2001 | Cox et al. | |
| 6,254,854 B1 | 7/2001 | Edwards et al. | |
| 6,263,872 B1 | 7/2001 | Schuster et al. | |
| 6,349,728 B1 | 2/2002 | Pham | |
| 6,360,739 B1 | 3/2002 | Rand et al. | |
| 6,443,146 B1 * | 9/2002 | Voges ...................... | 128/200.14 |
| 6,503,922 B2 | 1/2003 | Crooks et al. | |
| 6,516,796 B1 | 2/2003 | Beane et al. | |
| 6,532,965 B1 | 3/2003 | Abhulimen et al. | |
| 6,543,442 B2 | 4/2003 | Gonda et al. | |
| 6,557,552 B1 | 5/2003 | Cox et al. | |
| 6,598,602 B1 * | 7/2003 | Sjoholm ............... | A61M 11/005 |
| | | | 128/200.14 |
| 6,615,840 B1 | 9/2003 | Fournier et al. | |
| 6,629,524 B1 | 10/2003 | Goodall et al. | |
| 6,635,283 B2 | 10/2003 | Edwards et al. | |
| 6,637,430 B1 | 10/2003 | Voges et al. | |
| 6,647,987 B2 | 11/2003 | Gonda et al. | |
| 6,655,379 B2 | 12/2003 | Clark et al. | |
| 6,681,769 B2 | 1/2004 | Sprinkel, Jr. et al. | |
| 6,688,313 B2 | 2/2004 | Wrenn et al. | |
| 6,701,922 B2 | 3/2004 | Hindle et al. | |
| 6,749,835 B1 | 6/2004 | Lipp et al. | |
| 6,766,220 B2 | 7/2004 | Mcrae et al. | |
| 6,766,817 B2 | 7/2004 | Da Silva | |
| 6,772,756 B2 | 8/2004 | Shayan | |
| 6,772,757 B2 | 8/2004 | Sprinkel, Jr. | |
| 6,799,572 B2 | 10/2004 | Nichols et al. | |
| 6,799,576 B2 | 10/2004 | Farr et al. | |
| 6,803,545 B2 | 10/2004 | Blake et al. | |
| 6,803,550 B2 | 10/2004 | Sharpe et al. | |
| 6,804,458 B2 | 10/2004 | Sherwood et al. | |
| 6,810,883 B2 | 11/2004 | Felter et al. | |
| 6,845,216 B2 | 1/2005 | Schuster et al. | |
| 6,854,461 B2 | 2/2005 | Nichols et al. | |
| 6,854,470 B1 | 2/2005 | Pu | |
| 6,874,507 B2 | 4/2005 | Farr | |
| 6,875,020 B2 | 4/2005 | Niddrie et al. | |
| 6,883,516 B2 | 4/2005 | Hindle et al. | |
| 6,886,557 B2 | 5/2005 | Childers et al. | |
| 6,889,687 B1 | 5/2005 | Olsson | |
| 6,917,754 B2 | 7/2005 | Pedrotti et al. | |
| 6,923,179 B2 | 8/2005 | Gupta et al. | |
| 6,962,151 B1 | 11/2005 | Knoch et al. | |
| 6,994,096 B2 | 2/2006 | Rostami et al. | |
| 6,995,265 B2 | 2/2006 | Comins et al. | |
| 7,028,686 B2 | 4/2006 | Gonda et al. | |

(56) References Cited

U.S. PATENT DOCUMENTS

| | | |
|---|---|---|
| 7,040,314 B2 | 5/2006 | Nguyen et al. |
| 7,070,765 B2 | 7/2006 | Rabinowitz et al. |
| 7,078,019 B2 | 7/2006 | Rabinowitz et al. |
| 7,090,830 B2 | 8/2006 | Hale et al. |
| 7,117,867 B2 | 10/2006 | Cox et al. |
| 7,128,067 B2 | 10/2006 | Byron et al. |
| 7,132,545 B2 | 11/2006 | Comins et al. |
| 7,147,170 B2 | 12/2006 | Nguyen et al. |
| 7,163,015 B2 | 1/2007 | Moffitt et al. |
| 7,167,776 B2 | 1/2007 | Maharaji et al. |
| 7,182,961 B2 | 2/2007 | Batycky et al. |
| 7,185,659 B2 | 3/2007 | Sharpe |
| 7,234,470 B2 | 6/2007 | Yang |
| 7,252,840 B1 | 8/2007 | Batycky et al. |
| 7,293,565 B2 | 11/2007 | Griffin et al. |
| 7,373,938 B2 | 5/2008 | Nichols et al. |
| 7,384,649 B2 | 6/2008 | Batycky et al. |
| 7,392,809 B2 | 7/2008 | Larson et al. |
| 7,400,940 B2 | 7/2008 | Mcrae et al. |
| 7,435,408 B2 | 10/2008 | Edwards et al. |
| 7,442,388 B2 | 10/2008 | Weers et al. |
| 7,458,373 B2 | 12/2008 | Nichols et al. |
| 7,481,226 B2 | 1/2009 | Cholet |
| 7,530,352 B2 | 5/2009 | Childers et al. |
| 7,537,009 B2 | 5/2009 | Hale et al. |
| 7,540,286 B2 | 6/2009 | Cross et al. |
| 7,550,133 B2 | 6/2009 | Hale et al. |
| 7,581,540 B2 | 9/2009 | Hale et al. |
| 7,585,493 B2 | 9/2009 | Hale et al. |
| 7,645,442 B2 | 1/2010 | Hale et al. |
| 7,690,385 B2 | 4/2010 | Moffitt et al. |
| 7,726,310 B2 | 6/2010 | Andrus et al. |
| 7,726,320 B2 | 6/2010 | Robinson et al. |
| 7,743,766 B2 | 6/2010 | Gupta et al. |
| 7,766,013 B2 | 8/2010 | Wensley et al. |
| 7,767,698 B2 | 8/2010 | Warchol et al. |
| 7,810,505 B2 | 10/2010 | Yang |
| 7,832,410 B2 | 11/2010 | Hon |
| 7,913,688 B2 | 3/2011 | Cross et al. |
| 7,931,020 B2 | 4/2011 | Trees et al. |
| 7,942,147 B2 | 5/2011 | Hodges et al. |
| 7,953,613 B2 | 5/2011 | Gizewski |
| 7,997,280 B2 | 8/2011 | Rosenthal |
| 8,003,080 B2 | 8/2011 | Rabinowitz et al. |
| 8,066,010 B2 | 11/2011 | Newbery et al. |
| 8,074,644 B2 | 12/2011 | Hale et al. |
| 8,156,944 B2 | 4/2012 | Han |
| 8,191,555 B2 | 6/2012 | Herbrich et al. |
| 8,201,554 B2 | 6/2012 | Reinhold et al. |
| 8,205,622 B2 | 6/2012 | Pan |
| 8,251,063 B2 | 8/2012 | Andrus et al. |
| 8,256,433 B2 | 9/2012 | Gonda |
| 8,314,591 B2 | 11/2012 | Terry et al. |
| 8,322,350 B2 | 12/2012 | Lipowicz |
| 8,333,197 B2 | 12/2012 | Cross et al. |
| 8,353,302 B2 | 1/2013 | Olegario et al. |
| 8,365,742 B2 | 2/2013 | Hon |
| 8,371,310 B2 | 2/2013 | Brenneise |
| 8,375,957 B2 | 2/2013 | Hon |
| 8,375,959 B2 | 2/2013 | Dittrich et al. |
| 8,381,738 B2 | 2/2013 | Luan et al. |
| 8,381,739 B2 | 2/2013 | Gonda |
| 8,393,331 B2 | 3/2013 | Hon |
| 8,402,976 B2 | 3/2013 | Fernando et al. |
| 8,424,537 B2 | 4/2013 | Rosenthal |
| 8,479,747 B2 | 7/2013 | O'connell |
| 8,490,628 B2 | 7/2013 | Hon |
| 8,495,998 B2 | 7/2013 | Schennum |
| 8,499,766 B1 | 8/2013 | Newton |
| 8,505,548 B2 | 8/2013 | Hearn |
| 8,506,935 B2 | 8/2013 | Hale et al. |
| 8,511,318 B2 | 8/2013 | Hon |
| 8,515,570 B2 | 8/2013 | Lee |
| 8,528,569 B1 | 9/2013 | Newton |
| 8,539,959 B1 | 9/2013 | Scatterday |
| 8,550,069 B2 | 10/2013 | Alelov |
| 8,558,147 B2 | 10/2013 | Greim et al. |
| 8,578,942 B2 | 11/2013 | Schennum |
| 8,596,460 B2 | 12/2013 | Scatterday |
| 8,634,709 B2 | 1/2014 | Maharajh et al. |
| 8,636,012 B2 | 1/2014 | Le Roux et al. |
| 8,640,713 B2 | 2/2014 | Fiebelkorn |
| 8,678,012 B2 | 3/2014 | Li et al. |
| 8,689,804 B2 | 4/2014 | Fernando et al. |
| 8,689,805 B2 | 4/2014 | Hon |
| 8,695,794 B2 | 4/2014 | Scatterday |
| 8,714,150 B2 | 5/2014 | Alelov |
| 8,857,446 B2 | 10/2014 | Wu |
| 8,903,228 B2 | 12/2014 | Goodman et al. |
| 8,910,641 B2 | 12/2014 | Hon |
| 2001/0032647 A1 | 10/2001 | Schuster et al. |
| 2002/0037316 A1 | 3/2002 | Weers et al. |
| 2003/0051728 A1 | 3/2003 | Lloyd et al. |
| 2003/0056790 A1 | 3/2003 | Nichols et al. |
| 2003/0064052 A1 | 4/2003 | Waters et al. |
| 2003/0070555 A1 | 4/2003 | Reyhanloo |
| 2003/0108342 A1 | 6/2003 | Sherwood et al. |
| 2004/0020500 A1 | 2/2004 | Wrenn et al. |
| 2004/0025865 A1 | 2/2004 | Nichols et al. |
| 2004/0050383 A1 | 3/2004 | Cox et al. |
| 2004/0065324 A1 | 4/2004 | Pivinski |
| 2004/0084044 A1 | 5/2004 | Childers et al. |
| 2004/0099266 A1 | 5/2004 | Cross et al. |
| 2004/0129280 A1 | 7/2004 | Woodson et al. |
| 2004/0129793 A1 | 7/2004 | Nguyen et al. |
| 2004/0149737 A1 | 8/2004 | Sharpe et al. |
| 2004/0200488 A1 | 10/2004 | Felter et al. |
| 2004/0226569 A1 | 11/2004 | Yang et al. |
| 2005/0003003 A1 | 1/2005 | Basu et al. |
| 2005/0016550 A1 | 1/2005 | Katase |
| 2005/0043965 A1 | 2/2005 | Heller et al. |
| 2005/0090798 A1 | 4/2005 | Clark et al. |
| 2005/0169814 A1 | 8/2005 | Rosenthal |
| 2005/0172976 A1 | 8/2005 | Newman et al. |
| 2005/0235991 A1* | 10/2005 | Nichols et al. ......... 128/204.17 |
| 2006/0047368 A1* | 3/2006 | Maharajh ................ F22B 1/28 700/283 |
| 2006/0070633 A1 | 4/2006 | Rostami et al. |
| 2006/0130860 A1 | 6/2006 | Cholet |
| 2006/0174899 A9 | 8/2006 | Luan et al. |
| 2006/0185687 A1 | 8/2006 | Hearn et al. |
| 2006/0196518 A1 | 9/2006 | Hon |
| 2006/0249144 A1* | 11/2006 | DeHaan et al. ......... 128/200.14 |
| 2007/0068523 A1 | 3/2007 | Fishman |
| 2007/0074734 A1 | 4/2007 | Braunshtyen et al. |
| 2007/0102013 A1 | 5/2007 | Adams et al. |
| 2007/0163610 A1 | 7/2007 | Lindell et al. |
| 2007/0186940 A1 | 8/2007 | Bhattacharyya et al. |
| 2007/0267031 A1 | 11/2007 | Lik |
| 2007/0267032 A1 | 11/2007 | Shan |
| 2008/0108822 A1 | 5/2008 | King et al. |
| 2008/0138294 A1 | 6/2008 | Gonda et al. |
| 2008/0138398 A1 | 6/2008 | Gonda |
| 2008/0168987 A1 | 7/2008 | Denny et al. |
| 2008/0216828 A1 | 9/2008 | Wensley et al. |
| 2008/0216851 A1 | 9/2008 | Olegario et al. |
| 2008/0227088 A1 | 9/2008 | Albino et al. |
| 2008/0241255 A1 | 10/2008 | Rose et al. |
| 2008/0257367 A1 | 10/2008 | Paterno et al. |
| 2008/0315011 A1 | 12/2008 | Pesu |
| 2009/0004249 A1 | 1/2009 | Gonda |
| 2009/0004250 A1 | 1/2009 | Gonda |
| 2009/0005423 A1 | 1/2009 | Gonda |
| 2009/0014020 A1 | 1/2009 | Yoss et al. |
| 2009/0084865 A1 | 4/2009 | Maharajh |
| 2009/0095311 A1 | 4/2009 | Han |
| 2009/0126745 A1 | 5/2009 | Hon |
| 2009/0130178 A1 | 5/2009 | Oronsky et al. |
| 2009/0133691 A1 | 5/2009 | Yamada et al. |
| 2009/0151717 A1 | 6/2009 | Bowen et al. |
| 2009/0196930 A1* | 8/2009 | Surber et al. ................ 424/489 |
| 2009/0230117 A1 | 9/2009 | Fernando et al. |
| 2009/0234129 A1 | 9/2009 | Comins et al. |
| 2009/0258075 A1 | 10/2009 | Hale et al. |

(56) References Cited

U.S. PATENT DOCUMENTS

| | | |
|---|---|---|
| 2009/0260641 A1 | 10/2009 | Monsees et al. |
| 2009/0272379 A1 | 11/2009 | Thorens et al. |
| 2009/0283103 A1 | 11/2009 | Nielsen et al. |
| 2010/0031968 A1 | 2/2010 | Sheikh et al. |
| 2010/0063111 A1 | 3/2010 | Lindell et al. |
| 2010/0200008 A1 | 8/2010 | Taieb |
| 2010/0236546 A1 | 9/2010 | Yamada et al. |
| 2010/0236562 A1 | 9/2010 | Hearn et al. |
| 2010/0260688 A1 | 10/2010 | Warchol et al. |
| 2010/0288293 A1 | 11/2010 | Slasli et al. |
| 2010/0294268 A1 | 11/2010 | Wensley et al. |
| 2010/0313901 A1 | 12/2010 | Fernando et al. |
| 2010/0319686 A1 | 12/2010 | Schennum |
| 2011/0005535 A1 | 1/2011 | Xiu |
| 2011/0011160 A1 | 1/2011 | Gerde |
| 2011/0011396 A1 | 1/2011 | Fang |
| 2011/0094523 A1* | 4/2011 | Thorens et al. ............ 131/194 |
| 2011/0120456 A1* | 5/2011 | Immel ..................... 128/200.23 |
| 2011/0126848 A1 | 6/2011 | Zuber et al. |
| 2011/0147486 A1 | 6/2011 | Oliver et al. |
| 2011/0155153 A1 | 6/2011 | Thorens et al. |
| 2011/0168194 A1 | 7/2011 | Lik |
| 2011/0209717 A1 | 9/2011 | Li |
| 2011/0232654 A1 | 9/2011 | Mass |
| 2011/0233043 A1 | 9/2011 | Cross et al. |
| 2011/0240013 A1 | 10/2011 | Hale et al. |
| 2011/0240022 A1 | 10/2011 | Hodges et al. |
| 2011/0265806 A1 | 11/2011 | Alarcon et al. |
| 2011/0277756 A1 | 11/2011 | Terry et al. |
| 2011/0277757 A1* | 11/2011 | Terry et al. ............ 128/202.21 |
| 2011/0277760 A1 | 11/2011 | Terry et al. |
| 2011/0277761 A1 | 11/2011 | Terry et al. |
| 2011/0277764 A1 | 11/2011 | Terry et al. |
| 2011/0277780 A1 | 11/2011 | Terry et al. |
| 2011/0290244 A1 | 12/2011 | Schennum |
| 2011/0290248 A1 | 12/2011 | Schennum |
| 2011/0290249 A1 | 12/2011 | Schennum |
| 2011/0290268 A1 | 12/2011 | Schennum |
| 2011/0303231 A1 | 12/2011 | Li et al. |
| 2011/0304282 A1 | 12/2011 | Li et al. |
| 2011/0309157 A1 | 12/2011 | Yang et al. |
| 2012/0006342 A1 | 1/2012 | Rose et al. |
| 2012/0042886 A1 | 2/2012 | Piskorz |
| 2012/0048266 A1 | 3/2012 | Alelov |
| 2012/0090630 A1 | 4/2012 | Lik |
| 2012/0111324 A1 | 5/2012 | Kraft et al. |
| 2012/0111347 A1 | 5/2012 | Lik |
| 2012/0145169 A1 | 6/2012 | Yangyang et al. |
| 2012/0145170 A1 | 6/2012 | O'connell |
| 2012/0160251 A1 | 6/2012 | Hammel et al. |
| 2012/0167906 A1 | 7/2012 | Gysland |
| 2012/0174914 A1 | 7/2012 | Pirshafiey |
| 2012/0186594 A1 | 7/2012 | Liu |
| 2012/0199146 A1 | 8/2012 | Marangos |
| 2012/0204889 A1 | 8/2012 | Yunqiang |
| 2012/0227752 A1 | 9/2012 | Alelov |
| 2012/0227753 A1 | 9/2012 | Newton |
| 2012/0260926 A1 | 10/2012 | Martin |
| 2012/0260927 A1 | 10/2012 | Liu |
| 2012/0273589 A1 | 11/2012 | Lik |
| 2012/0279512 A1 | 11/2012 | Lik |
| 2012/0285475 A1 | 11/2012 | Liu |
| 2012/0285476 A1 | 11/2012 | Hon |
| 2012/0291791 A1 | 11/2012 | Pradeep |
| 2012/0312313 A1 | 12/2012 | Frija |
| 2012/0318882 A1 | 12/2012 | Abehasera |
| 2012/0325228 A1 | 12/2012 | Williams |
| 2013/0008457 A1 | 1/2013 | Zheng et al. |
| 2013/0019887 A1 | 1/2013 | Liu |
| 2013/0025609 A1 | 1/2013 | Liu |
| 2013/0032139 A1 | 2/2013 | Hale et al. |
| 2013/0032159 A1 | 2/2013 | Capuano |
| 2013/0037041 A1 | 2/2013 | Worm et al. |
| 2013/0042865 A1 | 2/2013 | Monsees et al. |
| 2013/0056013 A1 | 3/2013 | Terry et al. |
| 2013/0068239 A1 | 3/2013 | Youn |
| 2013/0074854 A1 | 3/2013 | Lipowicz |
| 2013/0081642 A1 | 4/2013 | Safari |
| 2013/0087160 A1 | 4/2013 | Gherghe |
| 2013/0098377 A1 | 4/2013 | Borschke et al. |
| 2013/0104916 A1 | 5/2013 | Bellinger et al. |
| 2013/0118510 A1 | 5/2013 | Kaljura et al. |
| 2013/0125906 A1 | 5/2013 | Lik |
| 2013/0139833 A1 | 6/2013 | Lik |
| 2013/0139836 A1 | 6/2013 | Blick et al. |
| 2013/0140200 A1 | 6/2013 | Scatterday et al. |
| 2013/0146489 A1 | 6/2013 | Scatterday et al. |
| 2013/0152954 A1 | 6/2013 | Youn |
| 2013/0152956 A1 | 6/2013 | Von Borstel et al. |
| 2013/0153449 A1 | 6/2013 | Agirbas |
| 2013/0157995 A1 | 6/2013 | Kem et al. |
| 2013/0160764 A1 | 6/2013 | Liu |
| 2013/0160765 A1 | 6/2013 | Liu |
| 2013/0167853 A1 | 7/2013 | Liu |
| 2013/0167854 A1 | 7/2013 | Shin |
| 2013/0168880 A1 | 7/2013 | Duke |
| 2013/0169230 A1 | 7/2013 | Li et al. |
| 2013/0173293 A1 | 7/2013 | Hyde et al. |
| 2013/0173294 A1 | 7/2013 | Hyde et al. |
| 2013/0173295 A1 | 7/2013 | Hyde et al. |
| 2013/0173296 A1 | 7/2013 | Hyde et al. |
| 2013/0173297 A1 | 7/2013 | Hyde et al. |
| 2013/0180524 A1 | 7/2013 | Shahaf et al. |
| 2013/0180525 A1 | 7/2013 | Cross et al. |
| 2013/0180533 A1 | 7/2013 | Kim et al. |
| 2013/0192615 A1 | 8/2013 | Tucker et al. |
| 2013/0192616 A1 | 8/2013 | Tucker et al. |
| 2013/0192617 A1 | 8/2013 | Thompson |
| 2013/0192618 A1 | 8/2013 | Li |
| 2013/0192619 A1 | 8/2013 | Tucker et al. |
| 2013/0192620 A1 | 8/2013 | Tucker et al. |
| 2013/0192621 A1 | 8/2013 | Li et al. |
| 2013/0192622 A1 | 8/2013 | Tucker et al. |
| 2013/0192623 A1 | 8/2013 | Tucker et al. |
| 2013/0199528 A1 | 8/2013 | Goodman et al. |
| 2013/0199551 A1 | 8/2013 | Le Roux et al. |
| 2013/0206154 A1 | 8/2013 | Fernando et al. |
| 2013/0213417 A1 | 8/2013 | Chong et al. |
| 2013/0213418 A1 | 8/2013 | Tucker et al. |
| 2013/0213419 A1 | 8/2013 | Tucker et al. |
| 2013/0213420 A1 | 8/2013 | Hon |
| 2013/0220315 A1 | 8/2013 | Conley et al. |
| 2013/0220316 A1 | 8/2013 | Oglesby et al. |
| 2013/0220847 A1 | 8/2013 | Fisher et al. |
| 2013/0228190 A1 | 9/2013 | Weiss et al. |
| 2013/0247924 A1 | 9/2013 | Scatterday et al. |
| 2013/0248385 A1 | 9/2013 | Scatterday et al. |
| 2013/0255675 A1 | 10/2013 | Liu |
| 2013/0255702 A1 | 10/2013 | Griffith, Jr. et al. |
| 2013/0263869 A1 | 10/2013 | Zhu |
| 2013/0276779 A1 | 10/2013 | Hale et al. |
| 2013/0276798 A1 | 10/2013 | Hon |
| 2013/0276802 A1 | 10/2013 | Scatterday et al. |
| 2013/0276804 A1 | 10/2013 | Hon |
| 2013/0284190 A1 | 10/2013 | Scatterday et al. |
| 2013/0284191 A1 | 10/2013 | Scatterday et al. |
| 2013/0284192 A1 | 10/2013 | Peleg et al. |
| 2013/0284194 A1 | 10/2013 | Newton |
| 2013/0298905 A1 | 11/2013 | Levin et al. |
| 2013/0298922 A1 | 11/2013 | Xiang et al. |
| 2013/0306064 A1 | 11/2013 | Thorens et al. |
| 2013/0306065 A1 | 11/2013 | Thorens et al. |
| 2013/0306084 A1 | 11/2013 | Flick |
| 2013/0306085 A1 | 11/2013 | Sanchez et al. |
| 2013/0312739 A1 | 11/2013 | Rome et al. |
| 2013/0312742 A1 | 11/2013 | Monsees et al. |
| 2013/0312776 A1 | 11/2013 | Newton et al. |
| 2013/0313139 A1 | 11/2013 | Scatterday et al. |
| 2013/0319407 A1 | 12/2013 | Liu |
| 2013/0319429 A1 | 12/2013 | Tayyarah et al. |
| 2013/0319431 A1 | 12/2013 | Cyphert et al. |
| 2013/0319435 A1 | 12/2013 | Flick |
| 2013/0319436 A1 | 12/2013 | Liu |
| 2013/0319437 A1 | 12/2013 | Liu |

(56) References Cited

U.S. PATENT DOCUMENTS

| | | |
|---|---|---|
| 2013/0319438 A1 | 12/2013 | Liu |
| 2013/0319439 A1 | 12/2013 | Gorelick et al. |
| 2013/0319440 A1 | 12/2013 | Capuano |
| 2013/0319989 A1 | 12/2013 | Liu |
| 2013/0319999 A1 | 12/2013 | Plojoux et al. |
| 2013/0333711 A1 | 12/2013 | Liu |
| 2013/0333712 A1 | 12/2013 | Scatterday |
| 2013/0336358 A1 | 12/2013 | Liu |
| 2013/0340750 A1 | 12/2013 | Thorens et al. |
| 2013/0340775 A1 | 12/2013 | Juster et al. |
| 2013/0340778 A1 | 12/2013 | Liu |
| 2013/0340779 A1 | 12/2013 | Liu |
| 2013/0341218 A1 | 12/2013 | Liu |
| 2013/0342157 A1 | 12/2013 | Liu |
| 2014/0000636 A1 | 1/2014 | O'connell |
| 2014/0000637 A1 | 1/2014 | O'connell |
| 2014/0000638 A1 | 1/2014 | Sebastian et al. |
| 2014/0007891 A1 | 1/2014 | Liu |
| 2014/0007892 A1 | 1/2014 | Liu |
| 2014/0014124 A1 | 1/2014 | Glasberg et al. |
| 2014/0014125 A1 | 1/2014 | Fernando et al. |
| 2014/0014126 A1 | 1/2014 | Peleg et al. |
| 2014/0020693 A1 | 1/2014 | Cochand et al. |
| 2014/0020696 A1 | 1/2014 | Liu |
| 2014/0020697 A1 | 1/2014 | Liu |
| 2014/0020699 A1 | 1/2014 | Dittrich et al. |
| 2014/0034070 A1 | 2/2014 | Schennum |
| 2014/0034071 A1 | 2/2014 | Levitz et al. |
| 2014/0048086 A1 | 2/2014 | Zhanghua et al. |
| 2014/0048444 A1 | 2/2014 | Scatterday |
| 2014/0053831 A1 | 2/2014 | Leamon et al. |
| 2014/0053856 A1 | 2/2014 | Liu |
| 2014/0053857 A1 | 2/2014 | Liu |
| 2014/0053858 A1 | 2/2014 | Liu |
| 2014/0060524 A1 | 3/2014 | Liu |
| 2014/0060525 A1 | 3/2014 | Hale et al. |
| 2014/0060527 A1 | 3/2014 | Liu |
| 2014/0060528 A1 | 3/2014 | Liu |
| 2014/0060529 A1 | 3/2014 | Zhang |
| 2014/0060532 A1 | 3/2014 | Hale et al. |
| 2014/0060552 A1 | 3/2014 | Cohen |
| 2014/0060554 A1 | 3/2014 | Collett et al. |
| 2014/0060555 A1 | 3/2014 | Chang et al. |
| 2014/0060556 A1 | 3/2014 | Liu |
| 2014/0064715 A1 | 3/2014 | Greim et al. |
| 2014/0066618 A1 | 3/2014 | Hale et al. |
| 2014/0069425 A1 | 3/2014 | Zhang |
| 2014/0072605 A1 | 3/2014 | Bennett et al. |
| 2014/0076310 A1 | 3/2014 | Newton et al. |
| 2014/0076338 A1 | 3/2014 | Kaljura et al. |
| 2014/0083442 A1 | 3/2014 | Scatterday |
| 2014/0083443 A1 | 3/2014 | Liu |
| 2014/0096781 A1 | 4/2014 | Sears et al. |
| 2014/0096782 A1 | 4/2014 | Ampolini et al. |
| 2014/0097103 A1 | 4/2014 | Cameron et al. |
| 2014/0107815 A1 | 4/2014 | Lamothe |
| 2014/0190496 A1 | 7/2014 | Wensley et al. |
| 2014/0261408 A1 | 9/2014 | DePiano et al. |
| 2014/0270729 A1 | 9/2014 | DePiano et al. |
| 2014/0270730 A1 | 9/2014 | DePiano et al. |
| 2014/0283855 A1 | 9/2014 | Hawes et al. |
| 2015/0196060 A1 | 7/2015 | Wensley et al. |

FOREIGN PATENT DOCUMENTS

| | | |
|---|---|---|
| CN | 1541577 A | 11/2004 |
| CN | 101084801 A | 12/2007 |
| CN | 201208444 Y | 3/2008 |
| CN | 100381083 C | 4/2008 |
| CN | 101878958 A | 11/2010 |
| CN | 202014571 U | 10/2011 |
| CN | 102266125 A | 12/2011 |
| CN | 102655773 A | 9/2012 |
| CN | 202445136 U | 9/2012 |
| CN | 202941411 U | 5/2013 |
| CN | 103209728 A | 7/2013 |
| CN | 203087526 U | 7/2013 |
| CN | 203194541 U | 9/2013 |
| CN | 103504479 A | 1/2014 |
| CN | 203538366 U | 4/2014 |
| CN | 103948172 A | 7/2014 |
| CN | 203676143 U | 7/2014 |
| CN | 203748678 U | 8/2014 |
| CN | 203884698 U | 10/2014 |
| CN | 203943069 U | 11/2014 |
| CN | 203952431 U | 11/2014 |
| CN | 203952433 U | 11/2014 |
| CN | 104254356 A | 12/2014 |
| CN | 204070546 U | 1/2015 |
| CN | 204120238 U | 1/2015 |
| CN | 104323433 A | 2/2015 |
| CN | 104397880 A | 3/2015 |
| DE | 202010002041 U1 | 5/2010 |
| EP | 0174550 B1 | 1/1991 |
| EP | 0438862 B1 | 11/1994 |
| EP | 0911041 A2 | 4/1999 |
| EP | 0615411 B1 | 7/1999 |
| EP | 0612221 B1 | 11/1999 |
| EP | 0628376 B1 | 12/1999 |
| EP | 0703734 B1 | 6/2000 |
| EP | 0640297 B1 | 10/2000 |
| EP | 0703735 B1 | 7/2001 |
| EP | 0706352 B1 | 3/2002 |
| EP | 0893071 B1 | 3/2002 |
| EP | 0951219 B1 | 11/2002 |
| EP | 0917830 B1 | 12/2002 |
| EP | 0857431 B1 | 3/2003 |
| EP | 1089712 B1 | 5/2003 |
| EP | 0822760 B1 | 6/2003 |
| EP | 0845220 B1 | 9/2003 |
| EP | 1349601 A2 | 10/2003 |
| EP | 1025397 B1 | 5/2004 |
| EP | 1154815 B1 | 7/2004 |
| EP | 1119384 B1 | 6/2005 |
| EP | 1011767 B1 | 11/2005 |
| EP | 1389137 B1 | 7/2006 |
| EP | 1322357 B1 | 1/2007 |
| EP | 1126892 B1 | 4/2007 |
| EP | 1276672 B1 | 11/2007 |
| EP | 1618803 B1 | 12/2008 |
| EP | 2022349 A1 | 2/2009 |
| EP | 2022350 A1 | 2/2009 |
| EP | 2047880 A1 | 4/2009 |
| EP | 1736065 B1 | 6/2009 |
| EP | 1265504 B1 | 7/2009 |
| EP | 1827146 B1 | 9/2009 |
| EP | 2100525 A1 | 9/2009 |
| EP | 2110033 A1 | 10/2009 |
| EP | 2110034 A1 | 10/2009 |
| EP | 2113178 A1 | 11/2009 |
| EP | 1415677 B1 | 12/2009 |
| EP | 2143346 A1 | 1/2010 |
| EP | 1392242 B1 | 5/2010 |
| EP | 1656171 B1 | 6/2010 |
| EP | 2201850 A1 | 6/2010 |
| EP | 2213321 A1 | 8/2010 |
| EP | 1055430 B1 | 9/2010 |
| EP | 2253233 A1 | 11/2010 |
| EP | 1556171 B1 | 12/2010 |
| EP | 2260733 A1 | 12/2010 |
| EP | 2276360 A1 | 1/2011 |
| EP | 1392381 B1 | 3/2011 |
| EP | 2316286 A1 | 5/2011 |
| EP | 2319334 A1 | 5/2011 |
| EP | 2327318 A1 | 6/2011 |
| EP | 2338360 A1 | 6/2011 |
| EP | 2338361 A1 | 6/2011 |
| EP | 2340729 A1 | 7/2011 |
| EP | 2340730 A1 | 7/2011 |
| EP | 2359705 A1 | 8/2011 |
| EP | 2378905 A1 | 10/2011 |
| EP | 2392218 A1 | 12/2011 |
| EP | 2399636 A1 | 12/2011 |
| EP | 2404515 A1 | 1/2012 |

(56) References Cited

FOREIGN PATENT DOCUMENTS

| | | | |
|---|---|---|---|
| EP | 2408494 A1 | 1/2012 |
| EP | 2432339 A1 | 3/2012 |
| EP | 1441785 B1 | 4/2012 |
| EP | 2443946 A1 | 4/2012 |
| EP | 2454956 A1 | 5/2012 |
| EP | 2257195 B1 | 6/2012 |
| EP | 2460422 A1 | 6/2012 |
| EP | 2460423 A1 | 6/2012 |
| EP | 2460424 A1 | 6/2012 |
| EP | 2461857 A1 | 6/2012 |
| EP | 2461858 A1 | 6/2012 |
| EP | 2468116 A1 | 6/2012 |
| EP | 2468117 A1 | 6/2012 |
| EP | 2468118 A1 | 6/2012 |
| EP | 2469969 A1 | 6/2012 |
| EP | 1463883 B1 | 7/2012 |
| EP | 2481308 A1 | 8/2012 |
| EP | 2489391 A2 | 8/2012 |
| EP | 2265138 B1 | 9/2012 |
| EP | 2493342 A1 | 9/2012 |
| EP | 2503912 A1 | 10/2012 |
| EP | 2515690 A1 | 10/2012 |
| EP | 2519121 A1 | 11/2012 |
| EP | 1549440 B1 | 12/2012 |
| EP | 2381805 B1 | 12/2012 |
| EP | 1558098 B1 | 1/2013 |
| EP | 2364101 B1 | 1/2013 |
| EP | 2540173 A1 | 1/2013 |
| EP | 2543265 A2 | 1/2013 |
| EP | 2170280 B1 | 3/2013 |
| EP | 2392217 B1 | 4/2013 |
| EP | 2578095 A2 | 4/2013 |
| EP | 2580970 A1 | 4/2013 |
| EP | 2580971 A1 | 4/2013 |
| EP | 2589306 A1 | 5/2013 |
| EP | 2606756 A1 | 6/2013 |
| EP | 2493341 B1 | 7/2013 |
| EP | 2609820 A1 | 7/2013 |
| EP | 2614731 A1 | 7/2013 |
| EP | 2614732 A1 | 7/2013 |
| EP | 1489931 B1 | 8/2013 |
| EP | 2625975 A1 | 8/2013 |
| EP | 2471392 B1 | 9/2013 |
| EP | 2640205 A2 | 9/2013 |
| EP | 2641490 A1 | 9/2013 |
| EP | 2645890 A1 | 10/2013 |
| EP | 2645891 A1 | 10/2013 |
| EP | 2645892 A1 | 10/2013 |
| EP | 2649891 A1 | 10/2013 |
| EP | 2649892 A1 | 10/2013 |
| EP | 2653047 A2 | 10/2013 |
| EP | 2654469 A1 | 10/2013 |
| EP | 2654470 A1 | 10/2013 |
| EP | 2654471 A1 | 10/2013 |
| EP | 1599243 B1 | 12/2013 |
| EP | 2488054 B1 | 12/2013 |
| EP | 2668858 A1 | 12/2013 |
| EP | 2668859 A2 | 12/2013 |
| EP | 2668860 A2 | 12/2013 |
| EP | 2672848 A2 | 12/2013 |
| EP | 2675302 A1 | 12/2013 |
| EP | 1750788 B1 | 1/2014 |
| EP | 2282649 B1 | 1/2014 |
| EP | 2695531 A1 | 2/2014 |
| EP | 2696711 A2 | 2/2014 |
| EP | 2698070 A1 | 2/2014 |
| EP | 2700324 A1 | 2/2014 |
| EP | 1465693 B1 | 3/2014 |
| EP | 2519122 B1 | 4/2014 |
| EP | 2712322 A1 | 4/2014 |
| EP | 2712350 A1 | 4/2014 |
| EP | 2712511 A1 | 4/2014 |
| EP | 2764783 A1 | 8/2014 |
| EP | 2787848 A1 | 10/2014 |
| GB | 2357035 A | 6/2001 |
| GB | 2466758 A | 7/2010 |
| GB | 2468932 B | 8/2011 |
| GB | 2466758 B | 9/2011 |
| GB | 2488257 B | 2/2013 |
| GB | 2465247 B | 3/2013 |
| GB | 2494315 A | 3/2013 |
| GB | 2496684 A | 5/2013 |
| GB | 2497536 A | 6/2013 |
| GB | 2497616 A | 6/2013 |
| GB | 2500293 A | 9/2013 |
| GB | 2500956 A | 10/2013 |
| GB | 2500957 A | 10/2013 |
| GB | 2501671 A | 11/2013 |
| GB | 2502052 A | 11/2013 |
| GB | 2502053 A | 11/2013 |
| GB | 2502054 A | 11/2013 |
| GB | 2502055 A | 11/2013 |
| GB | 2502162 A | 11/2013 |
| GB | 2502163 A | 11/2013 |
| GB | 2502164 A | 11/2013 |
| GB | 2504075 A | 1/2014 |
| GB | 2504076 A | 1/2014 |
| GB | 2504077 A | 1/2014 |
| JP | 2004283244 A | 10/2004 |
| JP | 2005-034021 A | 2/2005 |
| KR | 20110132290 A | 12/2011 |
| WO | WO 95/01137 A1 | 1/1995 |
| WO | WO 95/27411 A1 | 10/1995 |
| WO | WO 95/27412 A1 | 10/1995 |
| WO | WO 96/32854 A2 | 10/1996 |
| WO | WO 96/36247 A1 | 11/1996 |
| WO | WO 98/16088 A1 | 4/1998 |
| WO | WO 98/17130 A1 | 4/1998 |
| WO | WO 99/20939 A1 | 4/1999 |
| WO | WO 99/20940 A1 | 4/1999 |
| WO | WO 00/21598 A1 | 4/2000 |
| WO | WO 01/82725 A1 | 11/2001 |
| WO | WO 02/43514 A1 | 6/2002 |
| WO | WO 02/051466 A2 | 7/2002 |
| WO | WO 03/012565 A1 | 2/2003 |
| WO | WO 03/013618 A1 | 2/2003 |
| WO | WO 03/046695 A2 | 6/2003 |
| WO | WO 03/049792 A1 | 6/2003 |
| WO | WO 03/053502 A1 | 7/2003 |
| WO | WO 03/055486 A1 | 7/2003 |
| WO | WO 03/059413 A2 | 7/2003 |
| WO | WO 03/070031 A1 | 8/2003 |
| WO | WO 03/094900 A1 | 11/2003 |
| WO | WO 03/105529 A1 | 12/2003 |
| WO | WO 2004/022242 A1 | 3/2004 |
| WO | WO 2004/022243 A1 | 3/2004 |
| WO | WO 2004/041007 A2 | 5/2004 |
| WO | WO 2004/043175 A1 | 5/2004 |
| WO | WO 2004/050139 A2 | 6/2004 |
| WO | WO 2004/066762 A2 | 8/2004 |
| WO | WO 2004/080216 A1 | 9/2004 |
| WO | WO 2004/095955 A1 | 11/2004 |
| WO | WO 2004/106170 A2 | 12/2004 |
| WO | WO 2005/099494 A1 | 10/2005 |
| WO | WO 2005/120614 A1 | 12/2005 |
| WO | WO 2006/067627 A1 | 6/2006 |
| WO | WO 2006/070288 A2 | 7/2006 |
| WO | WO 2007/042941 A2 | 4/2007 |
| WO | WO 2007/078273 A1 | 7/2007 |
| WO | WO 2007/131449 A1 | 11/2007 |
| WO | WO 2007/131450 A1 | 11/2007 |
| WO | WO 2008/015441 A1 | 2/2008 |
| WO | WO 2008/069970 A2 | 6/2008 |
| WO | WO 2008/094693 A2 | 8/2008 |
| WO | WO 2009/001078 A2 | 12/2008 |
| WO | WO 2009/001082 A1 | 12/2008 |
| WO | WO 2009/001085 A2 | 12/2008 |
| WO | WO 2009/044280 A3 | 4/2009 |
| WO | WO 2009/044281 A1 | 4/2009 |
| WO | WO 2009/105919 A1 | 9/2009 |
| WO | WO 2009/112182 A1 | 9/2009 |
| WO | WO 2009/118085 A1 | 10/2009 |
| WO | WO 2009/120057 A1 | 10/2009 |
| WO | WO 2009/127401 A1 | 10/2009 |

(56) References Cited

FOREIGN PATENT DOCUMENTS

| | | |
|---|---|---|
| WO | WO 2009/135729 A1 | 11/2009 |
| WO | WO 2009/155734 A1 | 12/2009 |
| WO | WO 2010/003480 A1 | 1/2010 |
| WO | WO 2010/073018 A1 | 7/2010 |
| WO | WO 2010/073122 A1 | 7/2010 |
| WO | WO 2010/086074 A1 | 8/2010 |
| WO | WO 2010/090655 A1 | 8/2010 |
| WO | WO 2010/091593 A1 | 8/2010 |
| WO | WO 2010/107613 A1 | 9/2010 |
| WO | WO 2010/118644 A1 | 10/2010 |
| WO | WO 2010/133342 A1 | 11/2010 |
| WO | WO 2010/145894 A1 | 12/2010 |
| WO | WO 2011/010334 A1 | 1/2011 |
| WO | WO 2011/015825 A1 | 2/2011 |
| WO | WO 2011/015826 A1 | 2/2011 |
| WO | WO 2011/033396 A2 | 3/2011 |
| WO | WO 2011/034723 A1 | 3/2011 |
| WO | WO 2011/042212 A1 | 4/2011 |
| WO | 2011050943 A1 | 5/2011 |
| WO | WO 2011/050964 A1 | 5/2011 |
| WO | WO 2011/061130 A1 | 5/2011 |
| WO | WO 2011/063970 A1 | 6/2011 |
| WO | WO 2011/075722 A3 | 6/2011 |
| WO | WO 2011/076407 A1 | 6/2011 |
| WO | WO 2011/079932 A1 | 7/2011 |
| WO | WO 2011/079933 A1 | 7/2011 |
| WO | WO 2011/107737 A1 | 9/2011 |
| WO | WO 2011/117580 A2 | 9/2011 |
| WO | WO 2011/124033 A1 | 10/2011 |
| WO | WO 2011/127639 A1 | 10/2011 |
| WO | WO 2011/127644 A1 | 10/2011 |
| WO | WO 2011/130886 A1 | 10/2011 |
| WO | WO 2011/137453 A2 | 11/2011 |
| WO | WO 2011/146175 A2 | 11/2011 |
| WO | WO 2011/146264 A2 | 11/2011 |
| WO | WO 2011/146365 A2 | 11/2011 |
| WO | WO 2011/146372 A2 | 11/2011 |
| WO | WO 2011/146375 A2 | 11/2011 |
| WO | WO 2011/147687 A1 | 12/2011 |
| WO | WO 2011/147691 A1 | 12/2011 |
| WO | WO 2011/160788 A1 | 12/2011 |
| WO | WO 2012/019372 A1 | 2/2012 |
| WO | WO 2012/019533 A1 | 2/2012 |
| WO | 2012026963 A2 | 3/2012 |
| WO | WO 2012/026963 A2 | 3/2012 |
| WO | WO 2012/029064 A1 | 3/2012 |
| WO | WO 2012/039720 A1 | 3/2012 |
| WO | WO 2012/043941 A1 | 4/2012 |
| WO | WO 2012/045683 A2 | 4/2012 |
| WO | WO 2012/062619 A1 | 5/2012 |
| WO | WO 2012/065310 A1 | 5/2012 |
| WO | WO 2012/065754 A3 | 5/2012 |
| WO | WO 2012/070107 A1 | 5/2012 |
| WO | 2012085207 A1 | 6/2012 |
| WO | WO 2012/072264 A1 | 6/2012 |
| WO | WO 2012/072762 A1 | 6/2012 |
| WO | WO 2012/072790 A1 | 6/2012 |
| WO | WO 2012/081804 A2 | 6/2012 |
| WO | WO 2012/085082 A1 | 6/2012 |
| WO | WO 2012/085203 A1 | 6/2012 |
| WO | WO 2012/085205 A1 | 6/2012 |
| WO | WO 2012/088675 A1 | 7/2012 |
| WO | WO 2012/091249 A1 | 7/2012 |
| WO | WO 2012/100430 A1 | 8/2012 |
| WO | WO 2012/100523 A1 | 8/2012 |
| WO | WO 2012/109371 A2 | 8/2012 |
| WO | WO 2012/110819 A1 | 8/2012 |
| WO | WO 2012/129787 A1 | 10/2012 |
| WO | WO 2012/129812 A1 | 10/2012 |
| WO | WO 2012/133289 A1 | 10/2012 |
| WO | WO 2012/142293 A3 | 10/2012 |
| WO | WO 2012/164033 A1 | 12/2012 |
| WO | WO 2012/170424 A1 | 12/2012 |
| WO | WO 2012/173322 A1 | 12/2012 |
| WO | WO 2012/177510 A2 | 12/2012 |
| WO | WO 2013/004160 A1 | 1/2013 |
| WO | WO 2013/012157 A1 | 1/2013 |
| WO | WO 2013/014275 A2 | 1/2013 |
| WO | WO 2013/020220 A1 | 2/2013 |
| WO | WO 2013/022936 A1 | 2/2013 |
| WO | WO 2013/024263 A1 | 2/2013 |
| WO | WO 2013/025921 A1 | 2/2013 |
| WO | WO 2013/027066 A2 | 2/2013 |
| WO | WO 2013/030546 A1 | 3/2013 |
| WO | WO 2013/034039 A1 | 3/2013 |
| WO | WO 2013/034452 A1 | 3/2013 |
| WO | WO 2013/034453 A1 | 3/2013 |
| WO | WO 2013/034454 A1 | 3/2013 |
| WO | WO 2013/034455 A1 | 3/2013 |
| WO | WO 2013/034456 A1 | 3/2013 |
| WO | WO 2013/034458 A1 | 3/2013 |
| WO | WO 2013/034459 A1 | 3/2013 |
| WO | WO 2013/034460 A1 | 3/2013 |
| WO | WO 2013/040193 A2 | 3/2013 |
| WO | WO 2013/040275 A1 | 3/2013 |
| WO | WO 2013/040814 A1 | 3/2013 |
| WO | WO 2013/044537 A1 | 4/2013 |
| WO | WO 2013/045914 A1 | 4/2013 |
| WO | WO 2013/045944 A2 | 4/2013 |
| WO | WO 2013/050934 A1 | 4/2013 |
| WO | WO 2013/060607 A1 | 5/2013 |
| WO | WO 2013/060781 A1 | 5/2013 |
| WO | WO 2013/060827 A1 | 5/2013 |
| WO | WO 2013/064600 A1 | 5/2013 |
| WO | WO 2013/064690 A1 | 5/2013 |
| WO | WO 2013/075439 A1 | 5/2013 |
| WO | WO 2013/076098 A3 | 5/2013 |
| WO | WO 2013/076750 A1 | 5/2013 |
| WO | 2013083635 A1 | 6/2013 |
| WO | 2013083636 A1 | 6/2013 |
| WO | WO 2013/083631 A1 | 6/2013 |
| WO | WO 2013/083634 A1 | 6/2013 |
| WO | WO 2013/083635 A1 | 6/2013 |
| WO | WO 2013/083636 A1 | 6/2013 |
| WO | WO 2013/083638 A1 | 6/2013 |
| WO | WO 2013/083963 A1 | 6/2013 |
| WO | WO 2013/088230 A1 | 6/2013 |
| WO | WO 2013/089358 A1 | 6/2013 |
| WO | WO 2013/089551 A1 | 6/2013 |
| WO | WO 2013/091251 A1 | 6/2013 |
| WO | WO 2013/091252 A1 | 6/2013 |
| WO | WO 2013/093469 A2 | 6/2013 |
| WO | WO 2013/093470 A2 | 6/2013 |
| WO | WO 2013/093695 A1 | 6/2013 |
| WO | WO 2013/097158 A1 | 7/2013 |
| WO | WO 2013/098395 A1 | 7/2013 |
| WO | WO 2013/098396 A2 | 7/2013 |
| WO | WO 2013/098397 A2 | 7/2013 |
| WO | WO 2013/098398 A2 | 7/2013 |
| WO | WO 2013/102609 A1 | 7/2013 |
| WO | WO 2013/102611 A2 | 7/2013 |
| WO | WO 2013/102612 A2 | 7/2013 |
| WO | WO 2013/102613 A2 | 7/2013 |
| WO | WO 2013/102614 A2 | 7/2013 |
| WO | WO 2013/102615 A2 | 7/2013 |
| WO | WO 2013/104914 A1 | 7/2013 |
| WO | WO 2013/105739 A1 | 7/2013 |
| WO | WO 2013/110208 A1 | 8/2013 |
| WO | WO 2013/110209 A1 | 8/2013 |
| WO | WO 2013/110210 A1 | 8/2013 |
| WO | WO 2013/110211 A1 | 8/2013 |
| WO | WO 2013/110411 A2 | 8/2013 |
| WO | WO 2013/110412 A1 | 8/2013 |
| WO | WO 2013/113173 A1 | 8/2013 |
| WO | WO 2013/113174 A1 | 8/2013 |
| WO | WO 2013/113612 A1 | 8/2013 |
| WO | WO 2013/116558 A1 | 8/2013 |
| WO | WO 2013/116561 A1 | 8/2013 |
| WO | WO 2013/116567 A1 | 8/2013 |
| WO | WO 2013/116568 A2 | 8/2013 |
| WO | WO 2013/116571 A1 | 8/2013 |
| WO | WO 2013/116572 A1 | 8/2013 |
| WO | WO 2013/116983 A1 | 8/2013 |
| WO | WO 2013/120849 A1 | 8/2013 |

(56) References Cited

FOREIGN PATENT DOCUMENTS

| | | |
|---|---|---|
| WO | WO 2013/126770 A1 | 8/2013 |
| WO | WO 2013/126777 A2 | 8/2013 |
| WO | WO 2013/128176 A1 | 9/2013 |
| WO | WO 2013/128447 A1 | 9/2013 |
| WO | WO 2013/131763 A1 | 9/2013 |
| WO | WO 2013/131764 A1 | 9/2013 |
| WO | WO 2013/138384 A2 | 9/2013 |
| WO | WO 2013/138898 A1 | 9/2013 |
| WO | WO 2013/141906 A1 | 9/2013 |
| WO | WO 2013/141907 A1 | 9/2013 |
| WO | WO 2013/141994 A1 | 9/2013 |
| WO | WO 2013/141998 A2 | 9/2013 |
| WO | WO 2013/142671 A1 | 9/2013 |
| WO | WO 2013/142678 A1 | 9/2013 |
| WO | WO 2013/148810 A1 | 10/2013 |
| WO | WO 2013/149404 A1 | 10/2013 |
| WO | WO 2013/149484 A1 | 10/2013 |
| WO | WO 2013/151295 A1 | 10/2013 |
| WO | WO 2013/152873 A1 | 10/2013 |
| WO | WO 2013/155645 A1 | 10/2013 |
| WO | WO 2013/159245 A1 | 10/2013 |
| WO | WO 2013/164626 A1 | 11/2013 |
| WO | WO 2013/171206 A1 | 11/2013 |
| WO | WO 2013/171208 A1 | 11/2013 |
| WO | WO 2013/171215 A1 | 11/2013 |
| WO | WO 2013/171217 A1 | 11/2013 |
| WO | WO 2013/171221 A1 | 11/2013 |
| WO | WO 2013/173440 A1 | 11/2013 |
| WO | WO 2013/173469 A1 | 11/2013 |
| WO | WO 2013/174002 A1 | 11/2013 |
| WO | WO 2013/178767 A1 | 12/2013 |
| WO | WO 2013/178768 A1 | 12/2013 |
| WO | WO 2013/181788 A1 | 12/2013 |
| WO | WO 2013/181789 A1 | 12/2013 |
| WO | WO 2013/181796 A1 | 12/2013 |
| WO | WO 2013/181797 A1 | 12/2013 |
| WO | WO 2013/182024 A1 | 12/2013 |
| WO | WO 2013/182026 A1 | 12/2013 |
| WO | WO 2013/185357 A1 | 12/2013 |
| WO | WO 2013/185358 A1 | 12/2013 |
| WO | WO 2013/189048 A1 | 12/2013 |
| WO | WO 2013/189050 A1 | 12/2013 |
| WO | WO 2013/189052 A1 | 12/2013 |
| WO | WO 2013/190036 A1 | 12/2013 |
| WO | WO 2014/004648 A1 | 1/2014 |
| WO | WO 2014/005275 A1 | 1/2014 |
| WO | WO 2014/005614 A1 | 1/2014 |
| WO | WO 2014/008623 A1 | 1/2014 |
| WO | WO 2014/008646 A1 | 1/2014 |
| WO | WO 2014/012894 A1 | 1/2014 |
| WO | WO 2014/012905 A1 | 1/2014 |
| WO | WO 2014/012906 A1 | 1/2014 |
| WO | WO 2014/012907 A1 | 1/2014 |
| WO | WO 2014/015461 A1 | 1/2014 |
| WO | WO 2014/015463 A1 | 1/2014 |
| WO | WO 2014/015669 A1 | 1/2014 |
| WO | WO 2014/017794 A1 | 1/2014 |
| WO | WO 2014/029078 A1 | 2/2014 |
| WO | WO 2014/029103 A1 | 2/2014 |
| WO | WO 2014/029105 A1 | 2/2014 |
| WO | WO 2014/029827 A1 | 2/2014 |
| WO | WO 2014/031952 A1 | 2/2014 |
| WO | WO 2014/032275 A1 | 3/2014 |
| WO | WO 2014/032276 A1 | 3/2014 |
| WO | WO 2014/032280 A1 | 3/2014 |
| WO | WO 2014/037794 A2 | 3/2014 |
| WO | WO 2014/039308 A1 | 3/2014 |
| WO | WO 2014/040217 A1 | 3/2014 |
| WO | WO 2014/040221 A1 | 3/2014 |
| WO | WO 2014/040915 A1 | 3/2014 |
| WO | WO 2014/040988 A2 | 3/2014 |
| WO | WO 2014/043887 A1 | 3/2014 |
| WO | WO 2014/047826 A1 | 4/2014 |
| WO | WO 2014/047869 A1 | 4/2014 |
| WO | WO 2014/047948 A1 | 4/2014 |
| WO | WO 2014/047953 A1 | 4/2014 |
| WO | WO 2014/047954 A1 | 4/2014 |
| WO | WO 2014/047955 A1 | 4/2014 |
| WO | WO 2014/054035 A1 | 4/2014 |
| WO | WO 2014/058678 A1 | 4/2014 |
| WO | 2014/085719 A1 | 6/2014 |
| WO | 2014/110119 A1 | 7/2014 |
| WO | 2014/150573 A2 | 9/2014 |
| WO | 2014/187770 A2 | 11/2014 |
| WO | WO-2015042412 A1 | 3/2015 |

OTHER PUBLICATIONS

Aradigm, A respiratory specialty pharmaceutical company fulfiling unmet needs in pulmonary medicine. Feb. 2008.

Benowitz. Clinical pharmacology of nicotine: implications for understanding, preventing, and treating tobacco addiction. Clin Pharmacol Ther. Apr. 2008;83(4):531-41. doi: 10.1038/clpt.2008.3. Epub Feb. 27, 2008.

Brody, et al. Brain nicotinic acetylcholine receptor occupancy: effect of smoking a denicotinized cigarette. Int J Neuropsychopharmacol. Apr. 2009;12(3):305-16. doi: 10.1017/S146114570800922X. Epub Aug. 18, 2008.

Brody, et al. Cigarette smoking saturates brain alpha 4 beta 2 nicotinic acetylcholine receptors. Arch Gen Psychiatry. Aug. 2006;63(8):907-15.

CDC. Quitting smoking among adults—United States, 2001-2010. MMWR 2011;60:1513-19.

Heatherton, et al. The Fagerström Test for Nicotine Dependence: a revision of the Fagerström Tolerance Questionnaire. Br J Addict. Sep. 1991;86(9):1119-27.

Henningfield, et al. Tobacco dependence and withdrawal: science base, challenges and opportunities for pharmacotherapy. Pharmacol Ther. Jul. 2009;123(1):1-16. Epub Apr. 8, 2009.

Houezec. Role of nicotine pharmacokinetics in nicotine addiction and nicotine replacement therapy: a review. Int J Tuberc Lung Dis. Sep. 2003;7(9):811-9.

Polosa, et al. Effect of an electronic nicotine delivery device (e-Cigarette) on smoking reduction and cessation: a prospective 6-month pilot study. BMC Public Health. Oct. 11, 2011;11:786.

Rabinowitz, et al. Fast Onset Medications through Thermally Generated Aerosols. J Pharmacol Exp Ther. May 2004;309(2):769-75. Epub Jan. 29, 2004.

Rose, et al. Pulmonary delivery of nicotine pyruvate: sensory and pharmacokinetic characteristics. Exp Clin Psychopharmacol. Oct. 2010;18(5):385-94. doi: 10.1037/a0020834.

Wayne, et al. Tobacco industry research and efforts to manipulate smoke particle size: implications for product regulation. Nicotine Tob Res. Apr. 2008;10(4):613-25. doi: 10.1080/14622200801978698.

Whitten. Imaging Studies Elucidate Neurobiology of Cigarette Craving. NIDA Notes. Dec. 2008; 22(2):1-16.

WHO. Tobacco fact sheet. May 2012. Accessed Dec. 3, 2012, http://www.who.int/mediacentre/factsheets/fs339/en/index.html.

Williams. eNicotine Technologies. Taking the smoke out of smoking. OMB Meeting PPT. Dec. 18, 2013.

Patton, et al. Inhaling medicines: delivering drugs to the body through the lungs. Nat Rev Drug Discov. Jan. 2007;6(1):67-74.

e-Nicotine Technology to present clinical data at the society for research on nicotine and tobacco. e-Nicotine Technology Press release. Chapel Hill, NC. Jan. 31, 2014.

e-Nicotine Technology announces statistically and clinically significant reductions in smoking urge in clinical trial. e-Nicotine Technology Press release. Chapel Hill, NC. Feb. 14, 2014.

e-Nicotine Technology to bring electronic nicotine delivery products to market to address key unmet needs for smokers and the public health community. e-Nicotine Technology Press release. Chapel Hill, NC. Mar. 10, 2014.

International search report and written opinion dated Mar. 26, 2012 for PCT/US2011/048782.

International search report and written opinion dated Mar. 27, 2014 for PCT/US2013/072426.

Office action dated Sep. 4, 2012 for U.S. Appl. No. 13/460,982.

(56) References Cited

OTHER PUBLICATIONS

Office action dated Jan. 2, 2013 for U.S. Appl. No. 13/460,982.
Office action dated Jun. 25, 2013 for U.S. Appl. No. 13/460,982.
UK search report and opinion dated Feb. 12, 2014 for GB 1321023.2.
Zhang, et al. In Vitro Particle Size Distributions in Electronic and Conventional Cigarette Aerosols Suggest Comparable Deposition Patterns. Nicotine Tob Res. Feb. 2013; 15(2):501-508. doi: 10.1093/ntr/nts165. Epub Oct. 4, 2012.
U.S. Appl. No. 14/491,592, filed Sep. 19, 2014, Wensley et al.
CDC. Smoking-attributable mortality, years of potential life lost, and productivity losses—United States, 2000-2004. MMWR Morb Mortal Wkly Rep. Nov. 14, 2008;57(45):1226-8.
Gonda, I. Aerosols for delivery of therapeutic and diagnostic agents to the respiratory tract. Crit Rev Ther Drug Carrier Syst. 1990;6(4):273-313.
Kumar, et al. Initial Observations of Cell-Mediated Drug Delivery to the Deep Lung. Cell Transplant. 2011; 20(5): 609-618.
U.S. Appl. No. 14/603,217, filed Jan. 22, 2015.
International search report and written opinion dated May 1, 2015 for PCT Application No. US2015/012512.
Korean Intellectual Property Office, International Search Report and Written Opinion for PCT/US2014/056578, dated Jan. 12, 2015, 15 pages.
Korean Intellectual Property Office, International Search Report and Written Opinion for PCT/US2016/014158, dated May 3, 2016, 15 pages.
Japanese Patent Office, "Office Action", for JP2015-544216 with English translation, Sep. 15, 2017, 9 pgs.
Extended European Search Report for European Patent Application No. 15740106.8; dated Sep. 26, 2017; 9 pages.
Chinese Office Action with Search Report dated Nov. 7, 2017 for Chinese Application No. 201380071459.4, 9 pages.
United States Patent and Trademark Office, Office Action in U.S. Appl. No. 14/603,207; dated Jan. 24, 2018; 9 pages.
United States Patent and Trademark Office, Office Action in U.S. Appl. No. 15/004,431; dated Mar. 22, 2018; 27 pages.

* cited by examiner

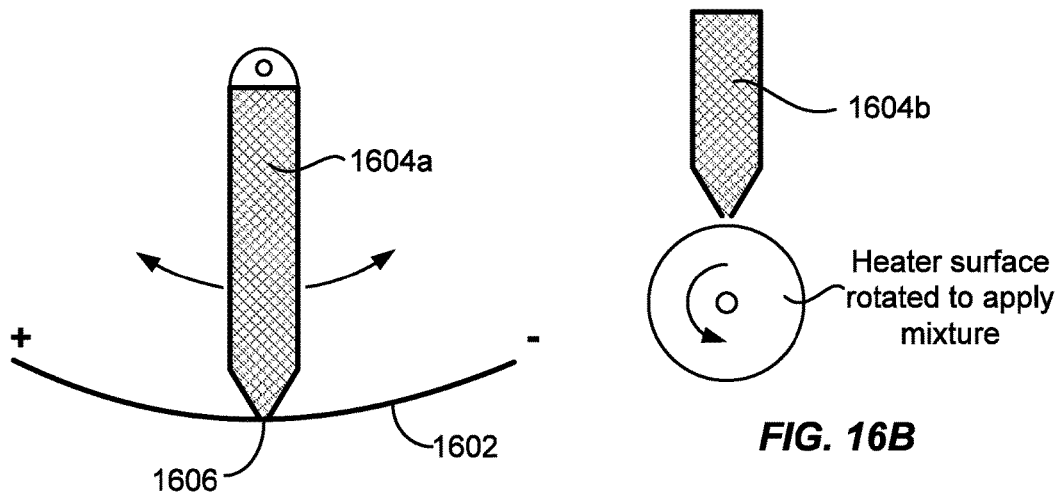
FIG. 16A
FIG. 16B
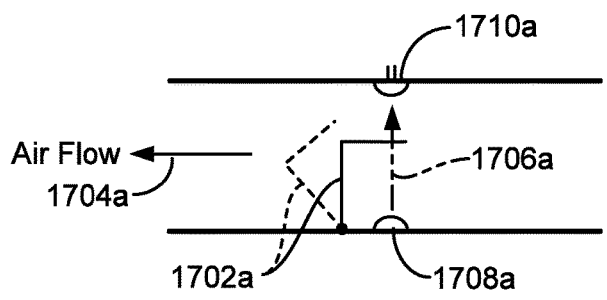
FIG. 17A
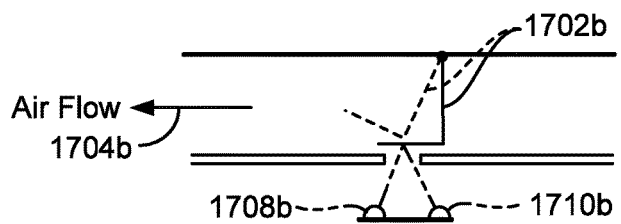
FIG. 17B

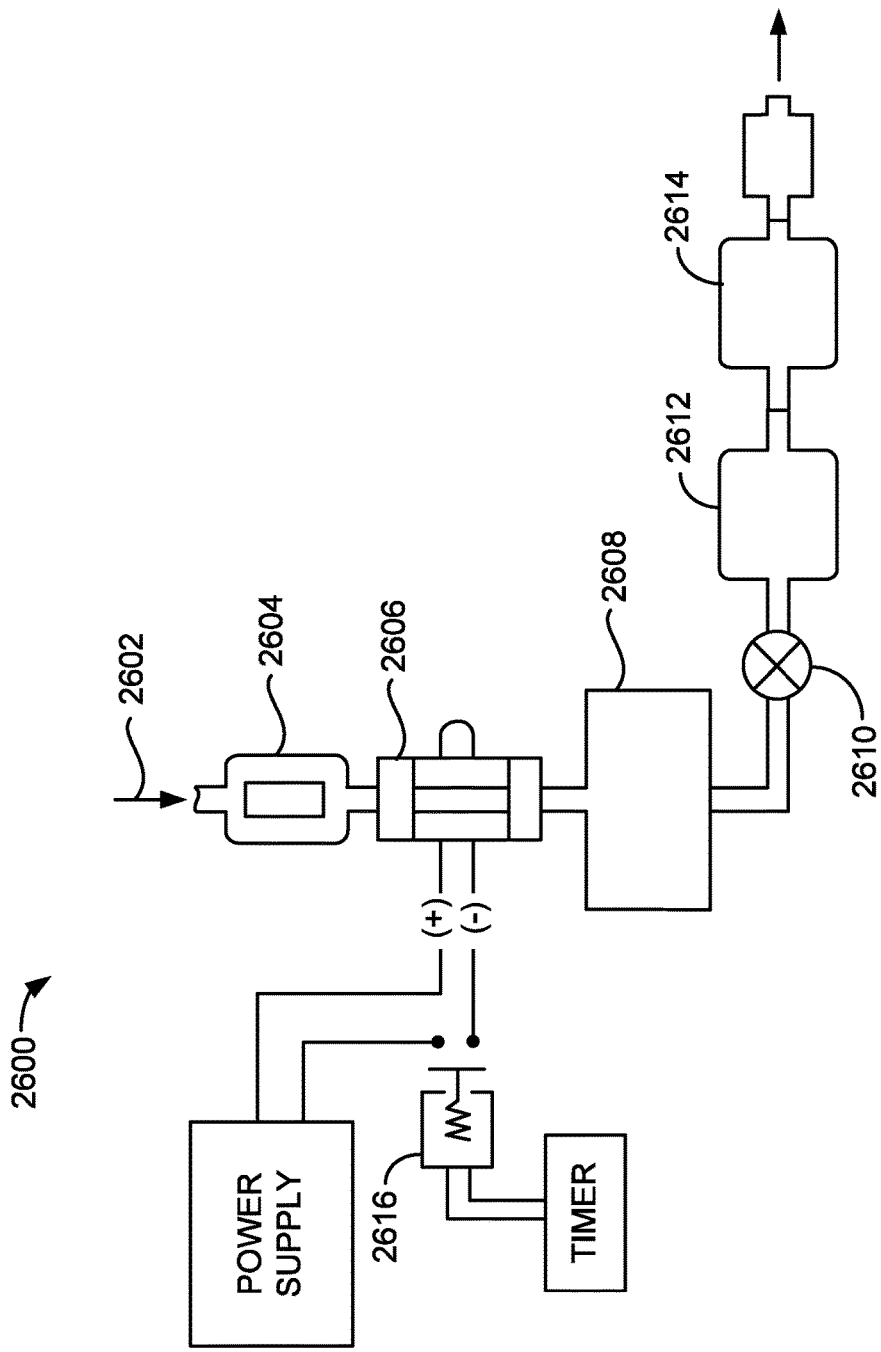

METHODS AND DEVICES FOR COMPOUND DELIVERY

CROSS-REFERENCE

This application is a continuation of PCT Application No. PCT/US13/72426, filed Nov. 27, 2013, which claims the benefit of U.S. Provisional Application No. 61/730,738, filed on Nov. 28, 2012, 61/794,601, filed on Mar. 15, 2013, 61/831,992, filed on Jun. 6, 2013, and 61/887,045, filed on Oct. 4, 2013, which applications are incorporated herein by reference in their entirety.

BACKGROUND

There is a need for new methods and devices for administering compounds, such as pharmaceutical agents, to a subject. In particular, there is a need for methods and devices for delivery of compounds to a subject where the compounds are aerosolized to fall within a specified particle size range. In some cases, particles within a specified size range can be efficiently delivered to the deep lung. For example, there is an urgent need for improved methods and devices to deliver nicotine to a subject in specified doses and in a specified particle range size without the carcinogens and other chemicals associated with combustible tobacco products.

In 2011, an estimated 19% of U.S. adults were current smokers (43.8 million people), and an estimated 950 children become addicted to smoking daily. Smokers spend approximately $83 billion to support their habit, and half of smokers will die from their habit. Studies indicate that about 85% of smokers want to quit; however, only about 5% succeed.

Current nicotine replacement therapies (NRTs) are not effective for approximately 85% of users. In some cases, existing NRTs and electronic cigarettes (eCigs) fail to provide sufficient doses of nicotine. Many smokers using NRTs under-dose, resulting in break-through cravings, which can lead to smoking lapses and eventual relapse. Smokers also vary widely in terms of their daily nicotine intake, ranging from "social smokers" who may only consume 1 or 2 cigarettes in the presence of friends and/or with alcohol, to heavy smokers who consume 60 or more cigarettes per day. Thus, a need exists to provide effective, customized doses of nicotine to individuals attempting to use recreational nicotine products or to leverage these devices to help quit smoking or nicotine intake all together.

Furthermore, to facilitate nicotine delivery and smoking cessation using an electronic nicotine delivery device, a need exists to control nicotine particle size generated from an electronic nicotine delivery device to match the rapid nicotine pharmacokinetics (PK) from smoking, which can result in deep lung absorption of nicotine. Deep lung absorption of nicotine can facilitate rapid delivery of nicotine to the brain, which can result in a subsequent cessation of nicotine cravings. When smoking combustible tobacco products, nicotine laden smoke particles are carried proximally on tar droplets (0.1-1.0 μM in diameter), are inhaled and travel to the small airways and alveoli in the deep lung. Nicotine off-gasses from particles and defuses to, and deposits on, the alveoli wall where it can be rapidly absorbed into the blood stream. A typical electronic cigarette does not produce an aerosol of nicotine with a particle size for deep lung delivery. Aerosol particles with an aerodynamic diameter larger than 5 μm can be too large to reach the deep lung because the particles can impact in the mouth and upper airway, resulting in a slow PK. Conversely, aerosol particles with a median aerodynamic diameter of less than 1 μm can be small enough to reach the deep lung but can be too light to gravitationally settle and can be exhaled, which can result in low dose delivery. Additionally, aerosols with small aerosol particle size can contain a larger percentage of the mass in the gas phase, which rapidly diffuses to the mouth and upper airway. Aerosol particles with an aerodynamic diameter of about 1 μm to about 5 μm can be small enough to reach the deep lung but large enough to gravitationally settle in alveoli, which can result in a rapid PK. A need exists for electronic nicotine delivery devices that produce such particles. In addition, a need exists for producing nicotine aerosols that produce such particles using the liquid drug. Moreover, a need exists for methods of using such devices to help users achieve a particular health goal or goals.

Also, a need exists for considering behavioral factors in smoking relapse and for integrating smoking cessation programs with social media to facilitate and maintain behavior change.

There is also a need for a drug delivery platform that is capable of dispensing a variety of drugs to a subject in a specified dose or in a specified particle size range.

SUMMARY

In one aspect, a condensation aerosol generating device for generating a condensation aerosol from a liquid formulation is provided, the device comprising: a) a reservoir comprising a liquid formulation; and b) a passageway comprising a heater element, an inlet, and an outlet, wherein the heater element is disposed in the passageway between the inlet and the outlet, wherein the reservoir is in fluid communication with the heater element, and wherein the passageway is configured to produce a condensation aerosol in the device, wherein the condensation aerosol has a mass median aerodynamic diameter (MMAD) of from about 1 μm to about 5 μm. In some cases, the heater element comprises a wick element and/or a coil. In some cases, the wick element comprises an electrically resistive material. The wick element and coil are formed from the same rod. The rod comprises a pliable material, the coil is a wire coil wrapped around the wick element, and the wick element is capable of being heated. In some cases, the coil spans a length of from about 0.25 cm to about 0.39 cm (from about 0.1 inch to about 0.15 inches) along the length of the wick element.

In some cases, the device further comprises a positive displacement or a peristaltic pump in fluid communication with the reservoir with the displacement pump configured to pump the liquid formulation comprising the liquid formulation to the heater element.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Novel features are set forth with particularity in the appended claims. A better understanding of the features and advantages will be obtained by reference to the following detailed description that sets forth illustrative embodiments, in which the principles are utilized, and the accompanying drawings of which:

FIGS. 16A and 16B illustrate embodiments for applying an agent (e.g., nicotine) to a heater element.

FIGS. 17A and 17B illustrate embodiments of mechanisms for generating an aerosol.

FIG. 26 illustrates a schematic of a test apparatus used for testing the effects of altering system parameters of an aerosol delivery device on particle size distribution.

FIGS. 27A, 27B, 27C, and 27D illustrate a schematic of a test bed used for generating an aerosol in the test apparatus of FIG. 26.

Figure 28:
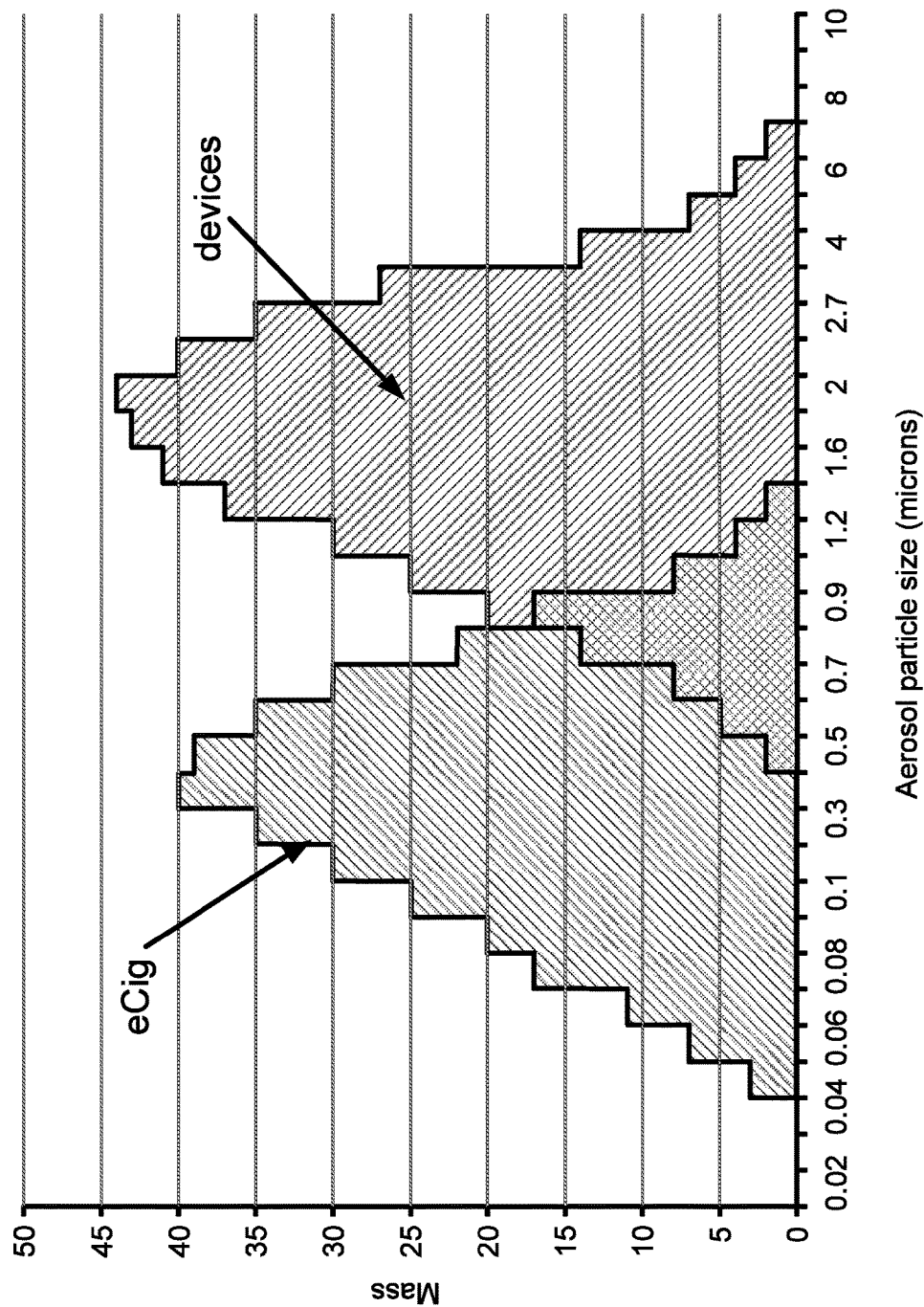

FIG. 28 shows a comparison of particle sizes of an aerosol created by an e-cigarette (e-cig) vs. an aerosol created by a device as provided herein.

Figure 29A:
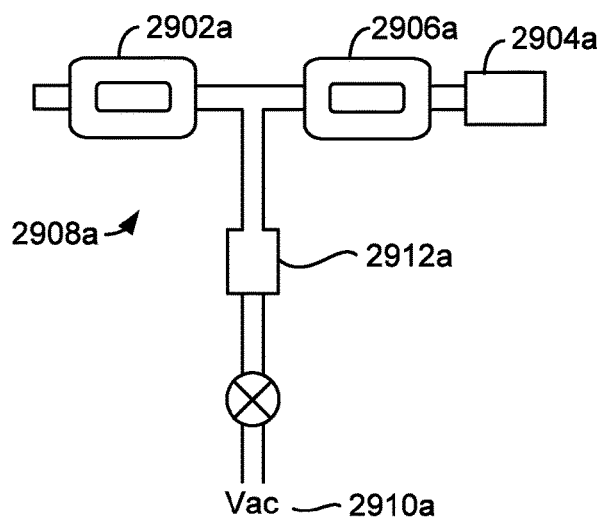
Figure 29B:
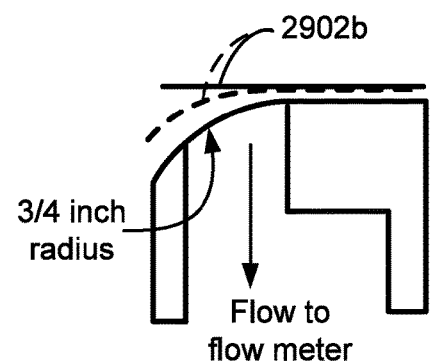

FIG. 29A illustrate a schematic of a test apparatus used for testing flow control. FIG. 29B illustrates a close-up of the valve (2904a) that is part of the test apparatus in FIG. 29A.

Figure 30A:
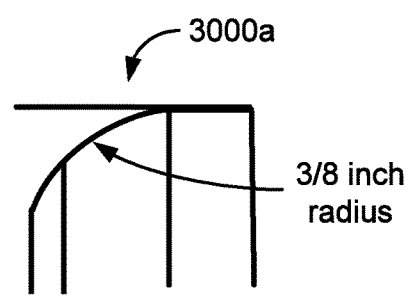
Figure 30B:
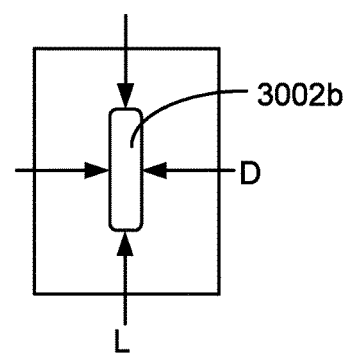

FIG. 30A illustrates an alternative valve flap for use in the valve (2904a) in FIG. 29A. FIG. 30B illustrates a slot for use in the bypass (2908a) in FIG. 29A.

FIGS. 31A, 31B, 31C, 31D, and 31E, illustrate embodiments of airflow configurations and heater element.

FIGS. 32A, 32B, 32C, 32D, and 32E illustrate embodiments of flow-through passageways.

Figure 33:
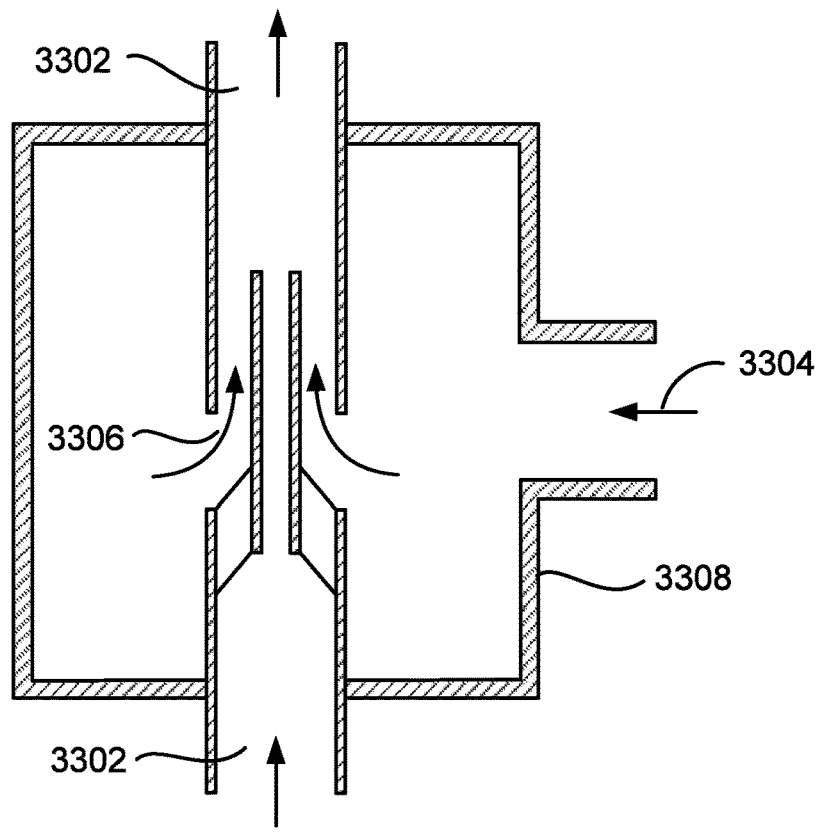

FIG. 33 illustrates an additional embodiment of a flow-through passageway.

Figure 34:
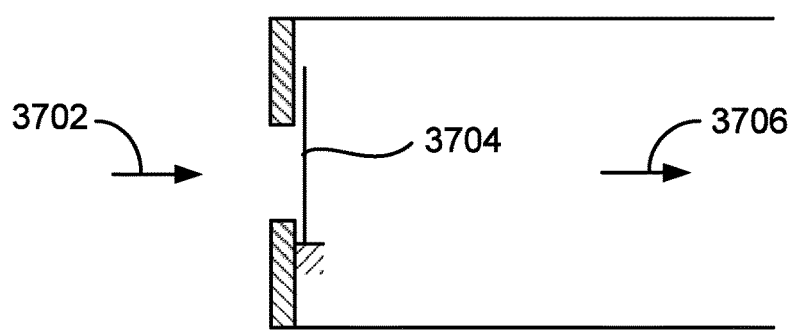

FIG. 34 illustrates an embodiment of a flow control valve.

Figure 35:
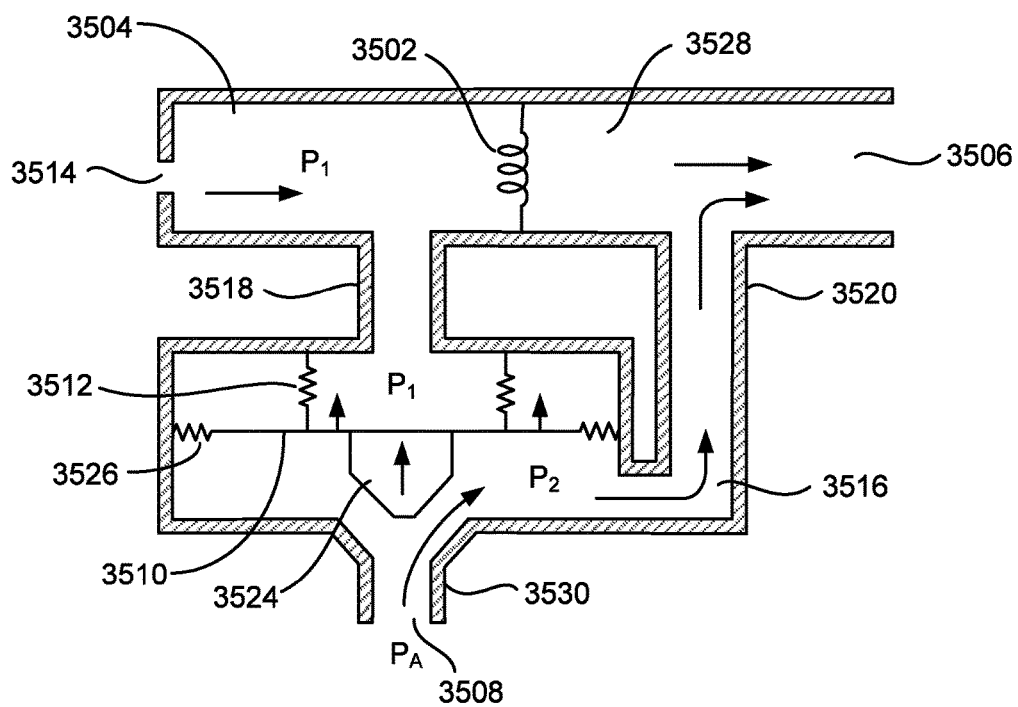

FIG. 35 illustrates an embodiment of a device comprising a primary and secondary airway.

Figure 36:
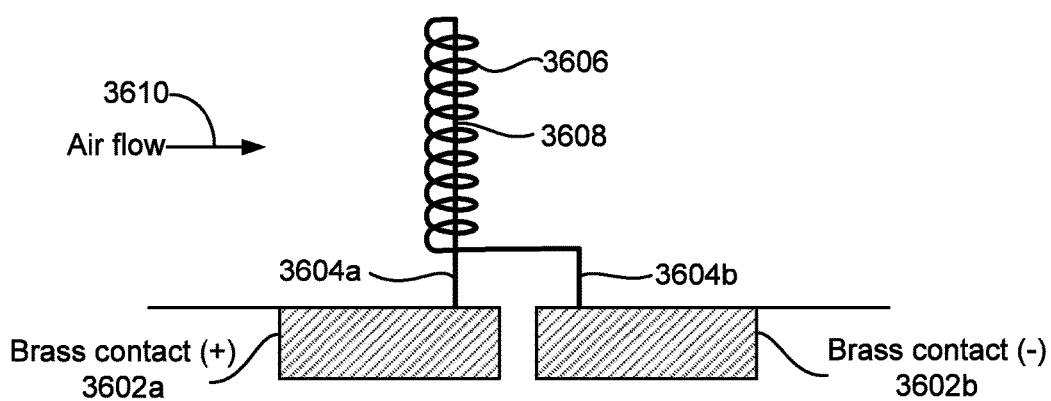

FIG. 36 illustrates another embodiment of a heater element.

Figure 37A:
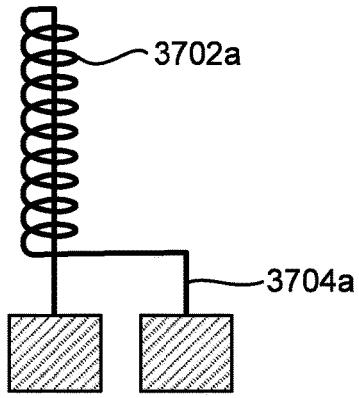
Figure 37B:
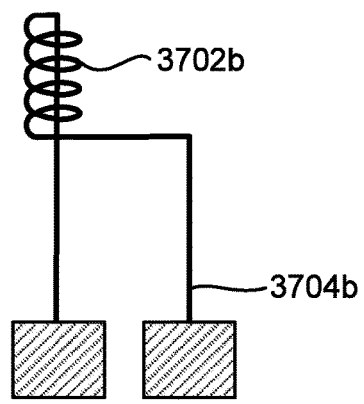

FIGS. 37A and 37B illustrate embodiments of a heater element similar to that shown in FIG. 36. FIG. 37A depicts a wire coil spanning a large percentage of the length of one end of the wire. FIG. 37B depicts a wire coil spanning a smaller percentage of the length of one end of the wire than shown in FIG. 37A.

Figure 38:
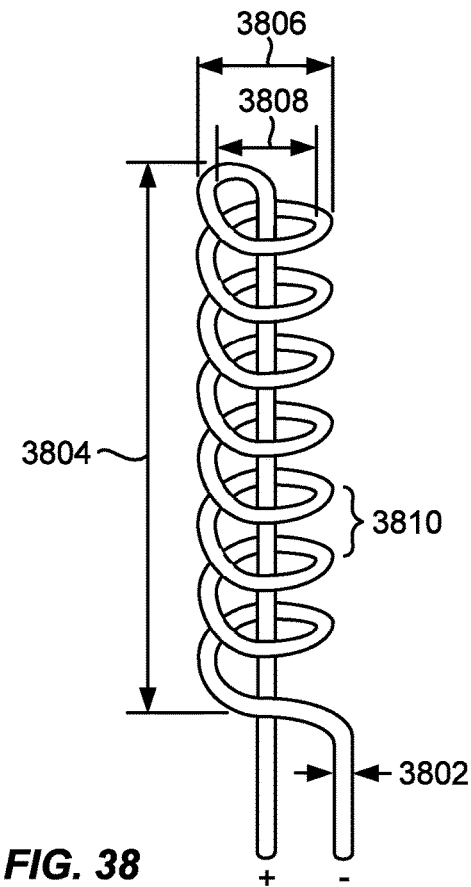

FIG. 38 is an enlarged representation of the wire coil from the heater element of FIG. 36.

Figure 39:
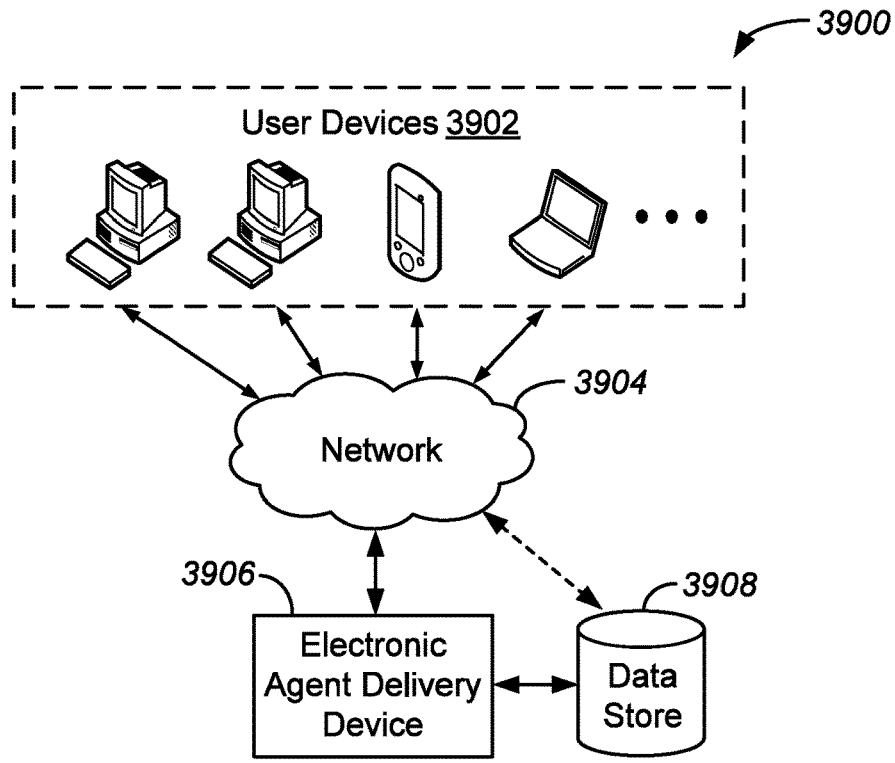

FIG. 39 illustrates components of eHealth-enabled electronic agent (e.g., nicotine) delivery system, in accordance with an embodiment.

Figure 40:
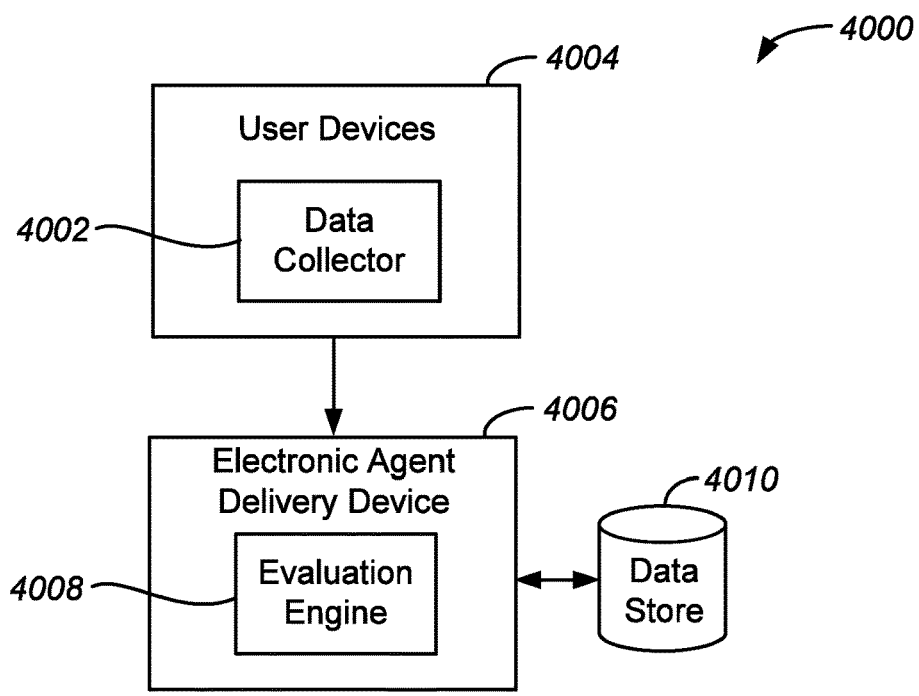

FIG. 40 illustrates example components of an electronic agent (e.g., nicotine) delivery system, in accordance with an embodiment.

Figure 41:
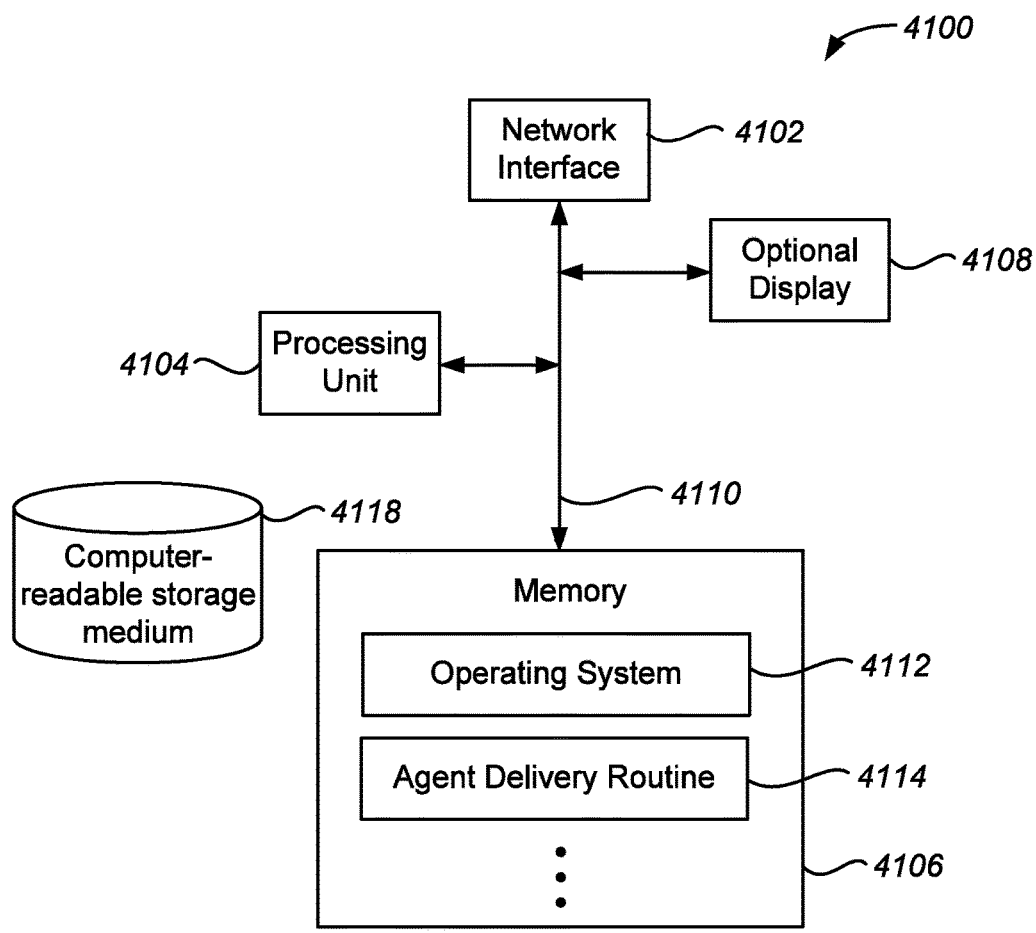

FIG. 41 illustrates example components of an electronic agent (e.g., nicotine) delivery device for implementing aspects described herein, in accordance with an embodiment.

Figure 42:
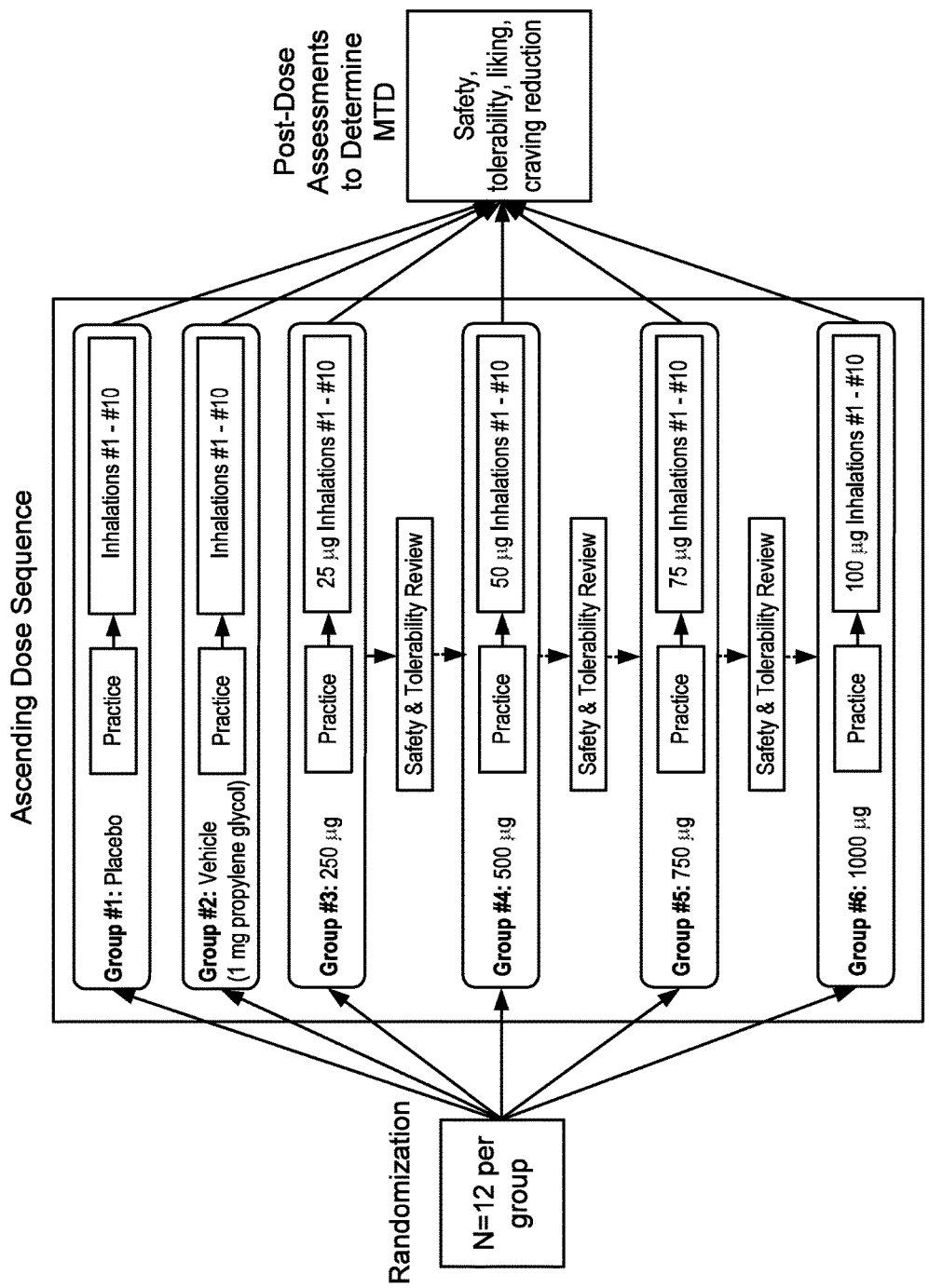

FIG. 42 illustrates an escalating dose protocol utilized during part 1 of a two part study for assessing the safety, tolerability, pharmacokinetics, and pharmacodynamics of a condensation aerosol comprising nicotine and propylene glycol produced from an electronic agent (e.g., nicotine) delivery device as provided herein.

Figure 43:
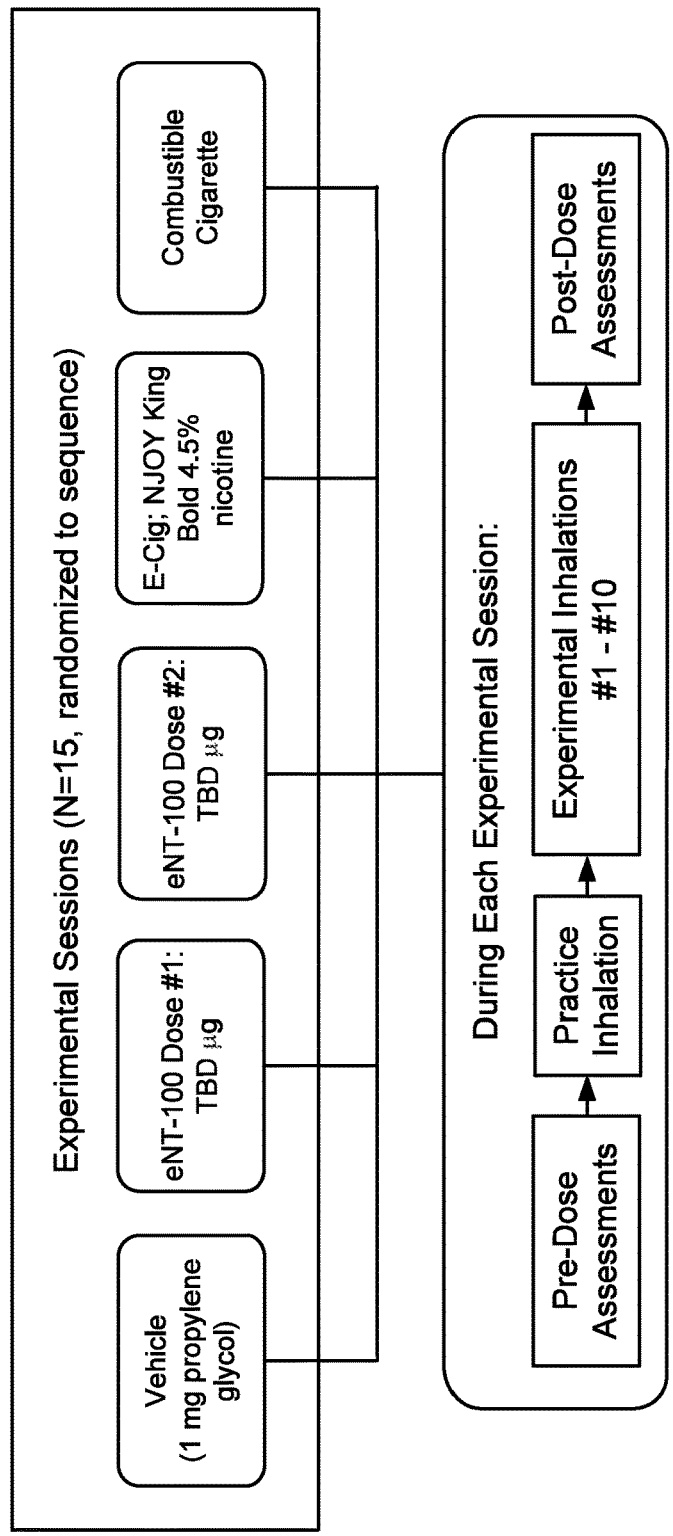

FIG. 43 illustrates a trial design for part 2 of a two part study for assessing the safety, tolerability, pharmacokinetics, and pharmacodynamics of a condensation aerosol comprising nicotine and propylene glycol produced from an electronic agent (e.g., nicotine) delivery device as provided herein.

Figure 44A:
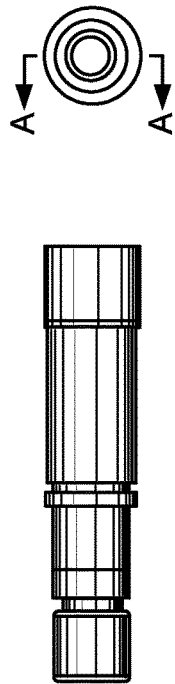
Figure 44B:
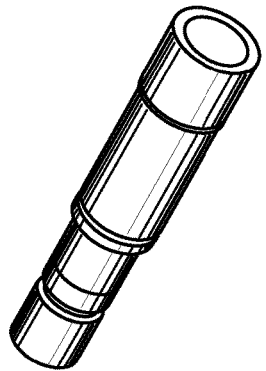
Figure 44C:
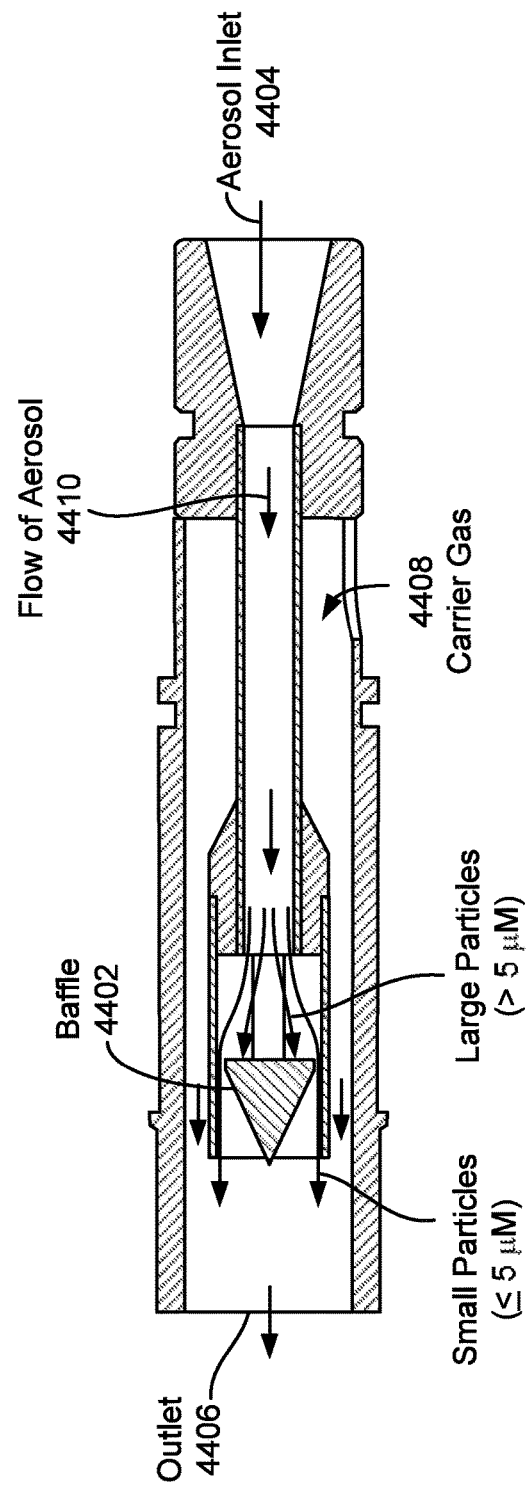

FIGS. 44A, 44B, and 44C illustrate embodiments of a passageway comprising a baffle for removing particles of a non-optimal size. FIGS. 44A and 44B illustrate exterior views of a passageway comprising a baffle. FIG. 44C illustrates an interior view of a passageway comprising a baffle.

DETAILED DESCRIPTION

I. Overview

Provided herein are devices, systems, kits, compositions, computer readable medium, and methods for electronic delivery of an agent to a subject. For example the devices, systems, computer readable medium, and methods can be used for electronic nicotine delivery, which can facilitate recreational nicotine delivery, full or partial smoking cessation, or facilitate full or partial cessation of nicotine intake. The subject can be a human. The human subject can be a smoker or an individual who uses tobacco or nicotine containing products. Devices described herein can generate an aerosol comprising an agent (e.g., nicotine), and the agent (e.g., nicotine) aerosol can have a known and consistent amount of agent (e g., nicotine). Also, devices and methods for dose titration are provided.

The devices, systems, kits, compositions, and computer readable medium provided herein can be part of an electronic agent (e.g., nicotine) delivery platform. The electronic platform for delivering an agent (e.g., nicotine) can be used to deliver the agent (e.g., nicotine) to a subject in a particular dose, with a particular mean particle size, pH, and airflow characteristics, which can affect back of the throat impaction and upper airway deposition. In one embodiment, the electronic delivery platform regulates a schedule of delivery of an agent (e.g., nicotine) to a user over time. Furthermore, provided herein are methods of tracking usage of an agent (e.g., nicotine) to suggest a dosing strategy based on the goal or goals of the user. In some cases, a user is a human. In some cases, a user is a human who smokes or otherwise uses tobacco or a nicotine containing product.

Provided herein are devices for generating a condensation aerosol comprising particles of a size suitable for delivery to the lungs of a subject. In some cases, a subject is a human. In some cases, a subject is a human who smokes or otherwise uses tobacco or nicotine containing products. The particles can be of a size suitable to delivery to the deep lung (i.e., alveoli) of the subject. The particles can be any of the sizes provided herein. In some cases, the particles can comprise a mass median aerodynamic diameter (MMAD) of from about 1 to about 5 µm. The particles can have a geometric standard deviation (GSD) of less than 2. The condensation aerosol can be generated from a formulation comprising a pharmaceutically active agent. The formulation can be in a liquid or solid phase prior to vaporization. The agent can be any agent as provided herein; in some cases, the agent is nicotine, and in some cases the nicotine is stabilized using one or more carriers (e.g., vegetable glycerin and/or propylene glycol). The device can comprise a heater element as provided herein and a configuration of flow-through passages or chambers suitable for generating condensation aerosols comprising particles of a size suitable for delivery to the deep lungs of a subject. For example, a device can comprise a primary flow-through chamber in fluid communication with a secondary flow-through chamber. The primary flow-through chamber can comprise an upstream and downstream opening, and the upstream opening can be an inlet for a carrier gas. The device can comprise an aerosol generation chamber, wherein the aerosol generation chamber is located (disposed) between the upstream and downstream openings within the primary flow through chamber. The aerosol generation chamber can comprise a heater element as provided herein and a source of a formulation comprising a pharmaceutically active agent (e.g. nicotine) as provided herein. The aerosol generation chamber can further comprise a configuration whereby the flow rate of the carrier gas entering the aerosol generation chamber is effective to condense a vapor generated from a formulation comprising a pharmaceutically active agent (e.g. nicotine) as provided herein within the aerosol generation chamber.

Devices and methods for aliquoting an agent (e.g., nicotine) to ensure dose-to-dose uniformity are provided herein. Furthermore, devices and methods are provided herein for sensing an inhalation by a user and triggering a device. Devices and methods are also provided herein for inhalation flow control.

Devices and methods of use of a closed loop design to control heating are provided herein. For example, a device provided herein can incorporate electronics that control for variability in battery condition and ensure consistent heating by direct measurement of resistance through the heater element to control for changes in battery voltage/charge.

Devices and methods are provided herein for transitioning a smoker away from cigarettes. For example, devices and methods are provided for enabling a subject to achieve full smoking or nicotine cessation. Devices and methods are provided for enabling a subject to achieve full smoking or nicotine cessation without relapse. Also, devices and methods are provided for enabling a subject to achieve full smoking or nicotine cessation with reduced, minimal, or no withdrawal symptoms. In some cases, a subject is a human. In some cases, a subject is a human who smokes or otherwise uses tobacco or a nicotine containing product.

eHealth tools provided herein can yield customized doses of an agent (e.g., nicotine) to a subject. In some cases, customized dosing regimens are provided, which can include instructions to dose at specific intervals, driven by reminders on the device. Devices and methods for providing customized feedback and behavioral support to a subject are also provided. In some cases, the customized feedback and/or behavioral support comprise simple instructions. The customized feedback and/or behavioral support can comprise use of social media to leverage social networks to help induce and/or maintain behavior change.

Also provided herein are methods of identifying individual user goals and matching user goals to an agent (e.g., nicotine) dose algorithm. Furthermore, provided herein are devices and methods for giving customized feedback to achieve a nicotine administration goal. Also, provided herein are devices and methods for giving customized feedback to achieve an agent administration goal. In some cases, an individual is a human. In some cases, an individual is a human who smokes or otherwise uses tobacco or a nicotine containing product.

II. Devices

FIG. 1 illustrates an embodiment of an electronic agent (e.g., nicotine) delivery device for controlling and reducing aerosol particle size for deep lung delivery and rapid pharmacokinetics. An agent, e.g., nicotine (102) is held in an agent (e.g., nicotine) reservoir (104), and can be wicked into a dosing mechanism (106). Upon inhalation, agent (e.g., nicotine) droplets are pulled out of the dosing mechanism. Small droplets are entrapped in airflow in the airway (108). A heater (110) can be in electrical communication with a battery (112). Larger droplets inertially impact with a heater (110), deposit, and are vaporized and reduced in size. Vapor condenses to form an optimum size aerosol by controlling airflow and vaporization rate.

Dosing

Provided herein are methods for administering agent (e.g., nicotine) challenge doses to a subject. In some cases, a subject is a human who smokes or otherwise uses tobacco or nicotine containing products. Methods are provided herein for generating condensation aerosols comprising particles comprising a mass median aerodynamic diameter (MMAD) effective for delivery to the deep lung of a subject. The methods can comprise supplying or delivering a liquid formulation comprising a pharmaceutically active agent (e.g. nicotine) to a passageway; vaporizing the liquid formulation using a heater element in the passageway to produce a vaporized liquid formulation; and flowing a carrier gas through the passageway at a flow rate effective to allow condensation of the vaporized liquid formulation into particles comprising a size effective for delivery to the deep lung. The size of the particles following condensation can be an MMAD of from about 1 to about 5 μm. The flow rate can be about 1 to about 10 liters per minute (LPM) (a range from about $1.667 \times 10^{-5}$ m$^3$/s to about $1.667 \times 10^{-4}$ m$^3$/s), e.g., at a vacuum of about 1 to about 15 inches of water (a range from about 249 Pa to about 3738 Pa). The flow resistance of the device can be about 0.05 to about 0.15 (cm of H$_2$O)$^{1/2}$/LPM. The liquid formulation can be supplied or delivered from a reservoir. The reservoir can comprise a tube, e.g., a capillary tube. The reservoir can be in fluid communication with the heater element. In some cases, the liquid formulation comprising a pharmaceutically active agent (e.g., nicotine) is delivered to the heater element through the use of a positive displacement pump. The positive displacement pump can be a reciprocating, metering, rotary-type, hydraulic, peristaltic, gear, screw, flexible impeller, diaphragm, piston, or progressive cavity pump, or any other pump utilizing positive displacement as known in the art. The positive displacement pump can be in fluid communication with the heater element. The positive displacement pump can be in fluid communication or fluidically coupled to a reservoir comprising a pharmaceutically active agent (e.g., nicotine). The positive displacement pump can be in fluid communication with the heater element and a reservoir comprising a pharmaceutically active agent (e.g., nicotine). The pharmaceutically active agent (e.g., nicotine) can be a liquid formulation. The positive displacement pump can be within the passageway or external to the passageway. The heater element can be any heater element as provided herein. The carrier gas can be air.

Methods for aliquoting an agent (e.g., nicotine) to ensure dose-to-dose uniformity are provided herein. For example, an element comprising porous materials can wick out fluid comprising agent (e.g., nicotine) at a particular rate in order to measure out a dose to provide dose-to-dose uniformity. A tube, e.g., a capillary tube can be used to measure out a dose. In one embodiment, heat is used as a means of ejecting a dose. A material or geometry of a device can be used to measure out a dose. In one embodiment, providing dose consistency controls for variability in environment and device. In another embodiment, inhalation flow control ensures that variability in inhalations by a user are controlled and corrected for, which can result in dose-to-dose consistency and predictable and desirable aerosol particle sizes.

In some cases, an agent (e.g., nicotine) is metered out into a pre-vaporization area in a device (dosing mechanism) through capillary action. The metering can occur between inhalations of a user of a device. Upon inhalation by a subject, an agent (e.g., nicotine) can be drawn into a vaporization chamber or onto a heater element. The agent can be a pharmaceutically active agent. The agent can be in a formulation that is liquid. The liquid formulation comprising a pharmaceutically active agent (e.g., nicotine) can be drawn or metered out into a vaporization chamber or onto a heater element upon inhalation by a subject. The human subject can be a smoker or user of tobacco or nicotine containing substances. The agent (e.g., nicotine) in the vaporization chamber or heater element can be vaporized and subsequently condense to form an aerosol. The aerosol can comprise agent (e.g., nicotine) particles of an optimum size to achieve certain biological effects (e.g., deep lung delivery producing rapid pharmacokinetics). Devices described herein can comprise a mechanism for separating out and reducing large aerosol particles to a size that can navigate to the deep lung of a subject. In the deep lung, the particles can settle and be rapidly absorbed. Also provided herein are methods for controlling aerosol particle size, pH, and other inhalation characteristics, which can ensure deep lung delivery and rapid pharmacokinetics. For example, the aerosol size control can result in rapid, cigarette-like nicotine absorption, which can help to satisfy nicotine cravings. Aerosol particles comprising nicotine produced by a heater element or device as provided herein can achieve peak plasma concentrations similar to peak plasma concentrations achieved by smoking a cigarette. Aerosol particles comprising nicotine produced by a heater element or device as provided herein can achieve peak plasma concentrations in a time frame similar to the time frame required to achieve peak plasma concentrations achieved by smoking a cigarette. The condensation aerosol comprising nicotine produced by any of the devices provided herein can result in rapid, cigarette-like nicotine absorption resulting in nicotine plasma concentrations similar or substantially similar to the nicotine arterial or venous plasma concentration achieved from smoking a cigarette. Smoking a single cigarette can produce peak increments of plasma nicotine concentration of 5-30 ng/ml.

Figure 12:
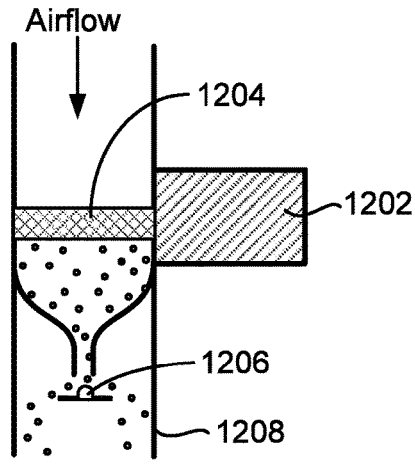
FIG. 12 illustrates an embodiment of a method of removal of an agent (e.g., nicotine) mixture from a reservoir and dispensing the nicotine into desired doses.

FIG. 12 illustrates an embodiment of a method of removal of an agent (e.g., nicotine) mixture from a reservoir and dispensing the agent (e.g., nicotine) into desired doses. FIG. 12 shows an agent (e.g., nicotine) reservoir (1202) next to a frit (1204) or porous material, such as a metal (stainless steel) or a ceramic, and allowing the agent (e.g., nicotine) to wick into it. Then, upon inhalation, the air can draw the agent (e.g., nicotine) into the airway (1208) and onto the heater element (1206). In some cases, the mixture is a liquid formulation comprising an agent (e.g., nicotine).

Figure 13:
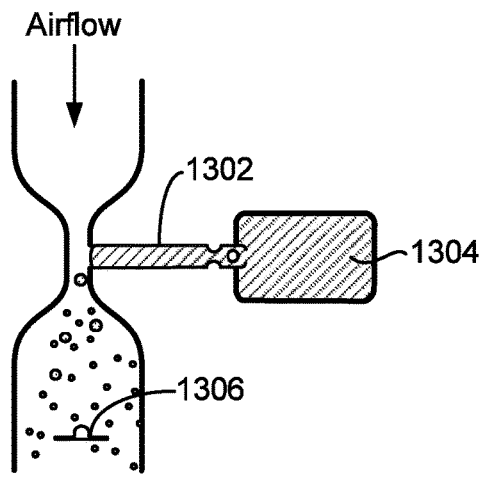
FIG. 13 illustrates another embodiment of a method for measuring an agent (e.g., nicotine) dose.

FIG. 13 illustrates another embodiment of a method for measuring a dose. Another method of dosing out the mixture is to draw the material out using a venturi. The device can comprise a tube, e.g., a capillary tube (1302), an agent (e.g., nicotine) reservoir (1304), and a heater element (1306). In some cases, the mixture is a liquid formulation comprising an agent (e.g., nicotine).

Figure 14:
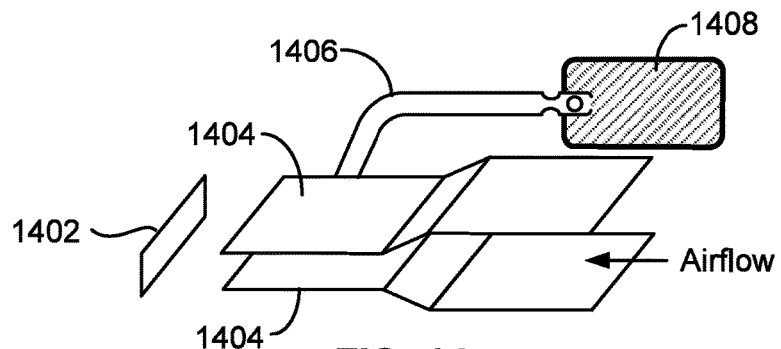
FIG. 14 illustrates another embodiment for measuring an agent (e.g., nicotine) dose.

FIG. 14 illustrates another embodiment of a method for measuring a dose. In this embodiment, an agent (e.g., nicotine) mixture can be wicked into a space between two parallel plates. The device can comprise a heater element (1402), plates (1404), tube, e.g., capillary tube (1406), and an agent (e.g., nicotine) reservoir (1408). In some cases, the mixture is a liquid formulation comprising an agent (e.g., nicotine).

Figure 15:
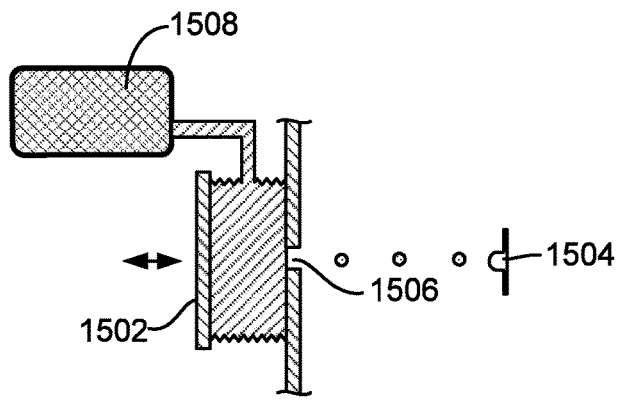
FIG. 15 illustrates another embodiment for measuring an agent (e.g., nicotine) dose.

FIG. 15 illustrates another embodiment for measuring a dose. An agent (e.g., nicotine) mixture can be ejected using a piezoelectric device (1502) and an attached chamber with an opening or orifice (1506). When the piezo is activated, either as a single pulse or as a series of pulses (vibrated) the mixture can be driven from the opening. By controlling the amplitude of the pulse or the number of pulses, the amount of material dosed can be controlled. The device can comprise an agent (e.g., nicotine) reservoir (1508) and a heater element (1504). In one embodiment, a piezo electric device is mounted on an end or a side of the reservoir and receipt of an electrical pulse causes the piezo to deflect and push a small amount of the agent (e.g., nicotine) formulation out of a tube, e.g., capillary tube mounted on another end of the reservoir onto a heater element. In some cases, the agent formulation is liquid.

All of the forgoing mechanisms to power the dispensing of a mixture (heat, piezo) can be powered by a user performing a maneuver such as pushing a button or lever. Mechanical energy from the user can also allow for alternative methods of applying agent (e.g., nicotine) to a heater surface. An agent (e.g., nicotine) can be applied to the heater element (1602), where the reservoir is moved over the heater surface in a sweeping (see FIG. 16A) or rolling motion (see FIG. 16B). The heater surface can be etched or pitted to accept the mixture.

To have the device generate an agent (e.g., nicotine) aerosol upon inhalation by a user, a movable member (e.g., vane (1702a or 1702b)) can be used that moves upon air flow (1704a or 1704b) caused by inhalation (see e.g., FIG. 17A or 17B). This member can break an optical path (1706a) (e.g., when no inhalation is occurring), move out of an optical path (1706a) when inhalation occurs (see e.g., FIG. 17A), or can complete an optical path when inhalation occurs (by, e.g., reflection; see e.g., FIG. 17B). An LED (1708a or 1708b) can be used to generate the light. To ensure that a sensor or detector (1710a or 1710b) does not get confused by stray light, the LED (1708a or 1708b) can be strobed in a particular pattern and only when that pattern is detected is an inhalation present. In some cases, optical light pipes can be used to route the light to the valve and to route the light back to the detector.

Figure 18:
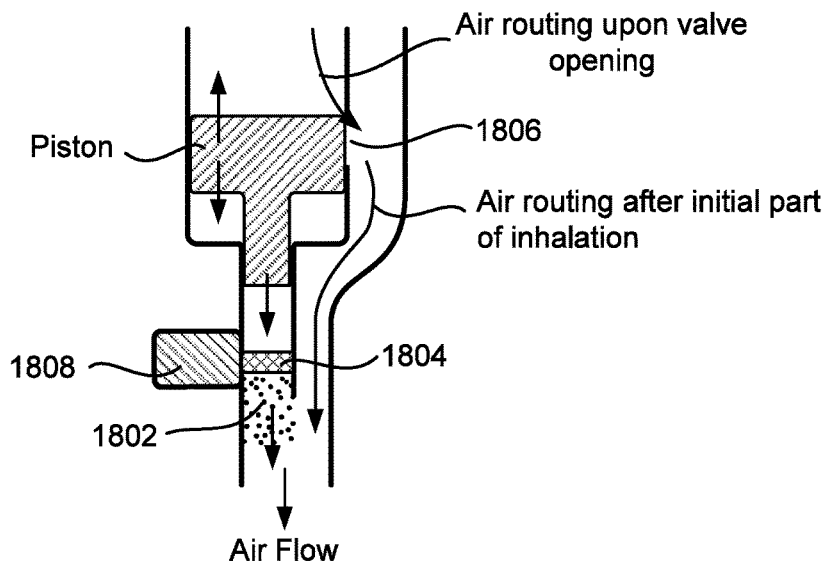
FIG. 18 illustrates an embodiment of a mechanism for dispensing an agent (e.g., nicotine) mixture.
Figure 19:
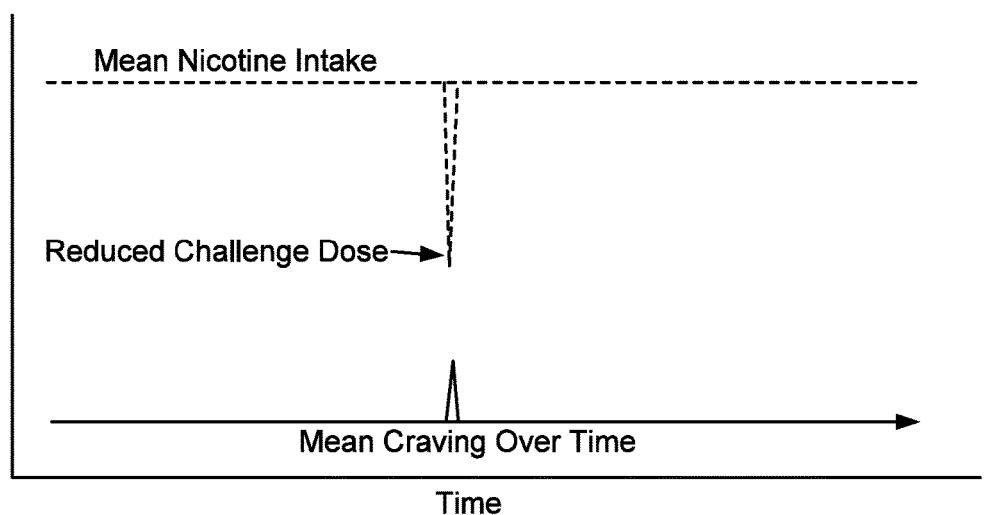
FIG. 19 illustrates feedback to a nicotine user regarding nicotine intake and mean craving over time.
Figure 20:
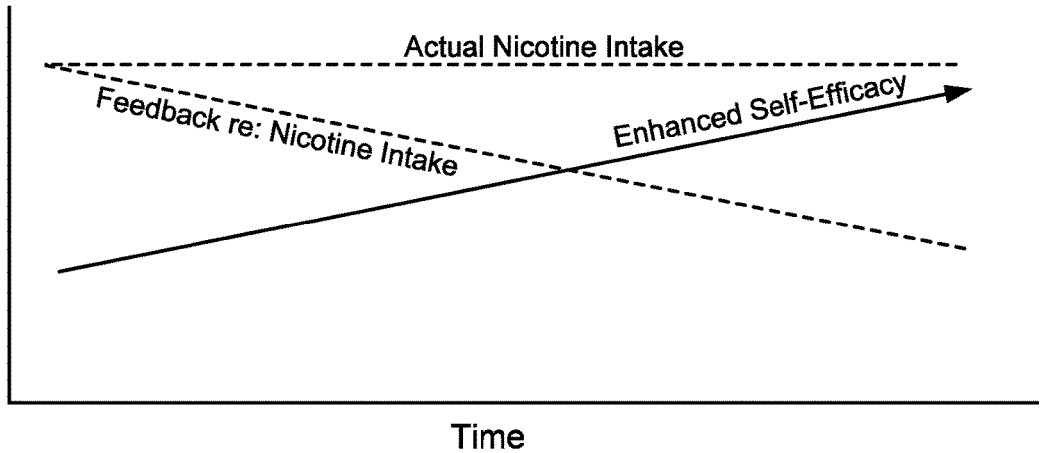
FIG. 20 illustrates customized feedback to a user of an electronic nicotine delivery device.

To dispense the agent (e.g., nicotine) mixture (1802) out of some of the frits (1804) or capillaries using the pressure from the inhalation a valve can be designed to create increased pressure in the initial part of the inhalation and decrease the resistance for the duration of the inhalation (see e.g., FIG. 18).

Figure 23:
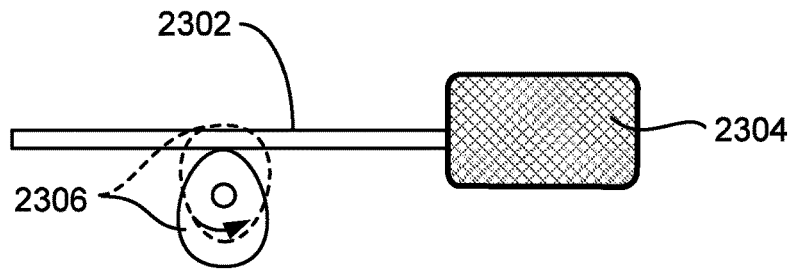
FIG. 23 illustrates another embodiment for measuring an agent (e.g., nicotine) dose.

FIG. 23 illustrates another embodiment of a method for measuring a dose. Another method of dosing out the mixture is to draw the material out using a peristaltic pump comprising a rotatable cam. The device can comprise a tube, e.g., capillary tube (2302), agent (e.g., nicotine) reservoir (2304), and a rotatable cam (2306) to pull or draw an agent (e.g., nicotine) mixture from the nicotine reservoir. In one embodiment, an agent (e.g., nicotine) delivery device comprises a disposable component that comprises the tube, e.g., capillary tube, and agent (e.g., nicotine) reservoir and a reusable component comprising the rotatable cam, wherein the tube, e.g., capillary tube and agent (e.g., nicotine) reservoir are mechanically connected to the rotatable cam by mating the disposable component to the reusable component. In some cases, the mixture is a liquid formulation comprising an agent (e.g., nicotine).

Figure 24:
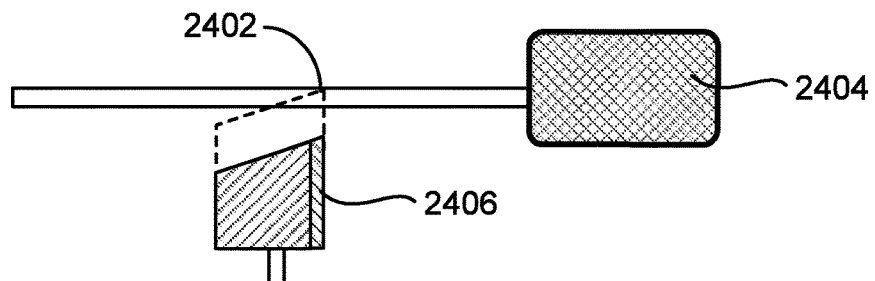
FIG. 24 illustrates another embodiment for measuring an agent (e.g., nicotine) dose.

FIG. 24 illustrates another embodiment of a method for measuring a dose. The device can comprise a tube, e.g., capillary tube (2402), agent (e.g., nicotine) reservoir (2404), and a cam made of variable durometer material (2406). The cam can comprise an area of high durometer material surrounded by low durometer material, wherein the tube, e.g., capillary tube can be sealed within the high durometer material. In one embodiment, an agent (e.g., nicotine) mixture can be pushed out of the tube, e.g., capillary tube by compression, wherein pressure is exerted on the low durometer material of the cam to cause compression of the tube, e.g., capillary tube, within the high durometer material. In one embodiment, an agent (e.g., nicotine) delivery device comprises a disposable component that comprises the tube, e.g., capillary tube and the agent (e.g., nicotine) reservoir and a reusable component comprising the cam made of variable durometer material, wherein the tube, e.g., capillary tube and agent (e.g., nicotine) reservoir are mechanically connected to the cam made of variable durometer material by mating the disposable component to the reusable component. In some cases, the mixture is a liquid formulation comprising an agent (e.g., nicotine).

Figure 25A:
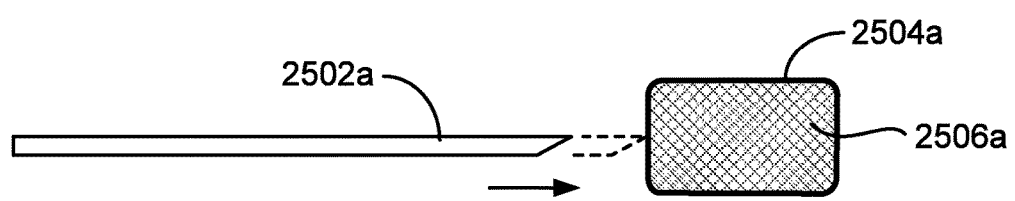
FIGS. 25A and 25B illustrate another embodiment of a method of removal of an agent (e.g., nicotine) mixture from a reservoir.
Figure 25B:
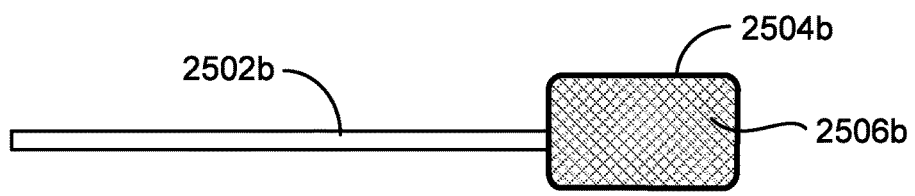
Figure 27A:
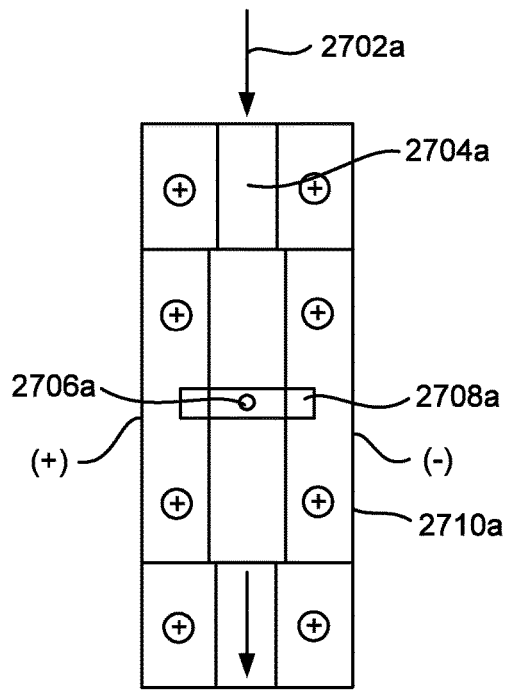
Figure 27B:
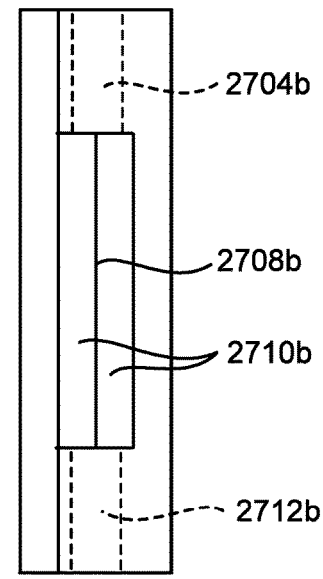
Figure 27C:
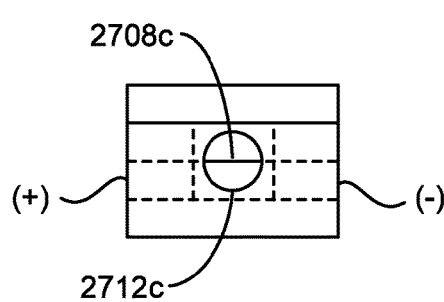
Figure 27D:
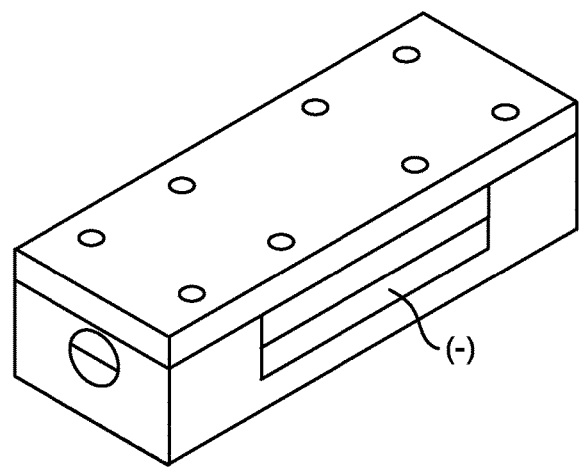

FIG. 25 illustrates an embodiment of a method of removal of an agent (e.g., nicotine) mixture from a reservoir. FIG. 25A shows a tube, e.g., capillary tube (2502a) adjacent to, but separate from, an agent (e.g., nicotine) reservoir (2504a) comprising an agent (e.g., nicotine) mixture (2506a). FIG. 25B shows that the tube, e.g., capillary tube (2502b) can pierce the agent (e.g., nicotine) reservoir (2504b) such that the agent (e.g., nicotine) mixture (2506b) within the agent (e.g., nicotine) reservoir can move into the tube, e.g., capillary tube and subsequently onto a heater element as provided herein. In one embodiment, the agent (e.g., nicotine) reservoir comprises a septum or seal, wherein the tube, e.g., capillary tube pierces the septum or seal. In one embodiment, the agent (e.g., nicotine) reservoir is a collapsible bag or container. In one embodiment, the collapsible bag or container is made of plastic, foil, or any other collapsible material known in the art. In a further embodiment, the tube, e.g., capillary tube can directly pierce an agent (e.g., nicotine) reservoir that is made of a collapsible material. In one embodiment, the tube, e.g., capillary tube is not inserted into the agent (e.g., nicotine) reservoir prior to a first use of the device, wherein upon first use, the tube, e.g., capillary tube, is inserted into the agent (e.g., nicotine) reservoir such that an agent (e.g., nicotine) mixture can move from the agent (e.g., nicotine) reservoir into the tube, e.g., capillary tube and subsequently onto a heater element as provided herein. In some cases, the mixture is a liquid formulation comprising an agent (e.g., nicotine).

Flavorings

A flavoring can be used to pair nicotine administration with certain gustatory and/or olfactory sensations. Subsequent administration of agent (e.g., nicotine) doses can be reduced while retaining the flavoring to help the user reduce their agent (e.g., nicotine) dependency and enable cravings to be fully or partially sated using the flavoring as a conditioned stimulus.

Particle Size

The particle size can be from about 1 to about 10 microns, about 1 to about 9 microns, about 1 to about 7 microns, about 1 to 6 microns, about 1 to about 5 microns, about 1 to about 4 microns, about 1 to about 3 microns, or about 1 to about 2 microns. The particle size is a mass median aerodynamic diameter (MMAD).

Agent (e.g., Nicotine) Reservoir

Figure 4:
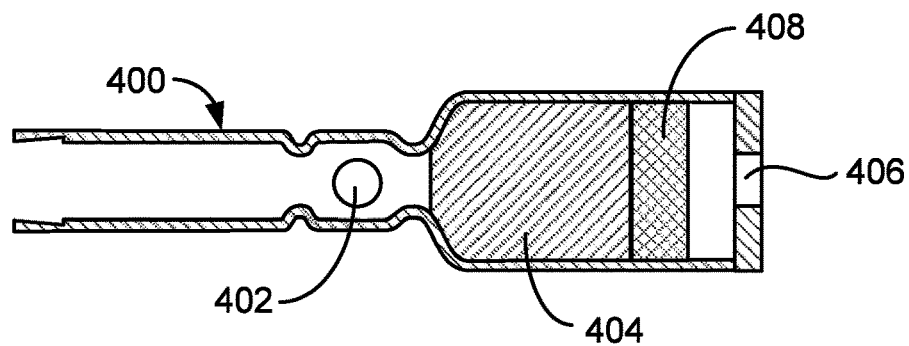
FIG. 4 illustrates an embodiment of an agent (e.g., nicotine) reservoir.

FIG. 4 illustrates an embodiment of an agent (e.g., nicotine) reservoir (404) that can be used in an electronic agent (e.g., nicotine) delivery device provided herein. A tube, e.g., capillary tube (400) with a valve (402) does not need to be inserted into a separate reservoir, but can be the reservoir (404) itself by extending away from the ejection end. The diameter of the tube, e.g., capillary tube, can be increased to store more mixture. To allow for the mixture to be pulled from the reservoir without creating a low pressure, which could resist the mixture leaving, the back end can have a vent (406). To stop an agent (e.g., nicotine) from vaporizing or evaporating from the back end a section of the reservoir could be filled with a soft material such as a wax or grease plug. This plug (408) can be drawn along the reservoir as the mixture is used. In one embodiment, the agent (e.g., nicotine) reservoir is cylindrical. In one embodiment, the agent (e.g., nicotine) reservoir holds a formulation comprising 200 mg of agent (e.g., nicotine) mixed with 1000 mg of propylene glycol. In one embodiment, the agent (e.g., nicotine) reservoir holds a formulation comprising 200 ug of agent (e.g., nicotine) mixed with 1000 ug of propylene glycol. In some cases, the agent (e.g., nicotine) formulation is a liquid formulation.

Figure 5:
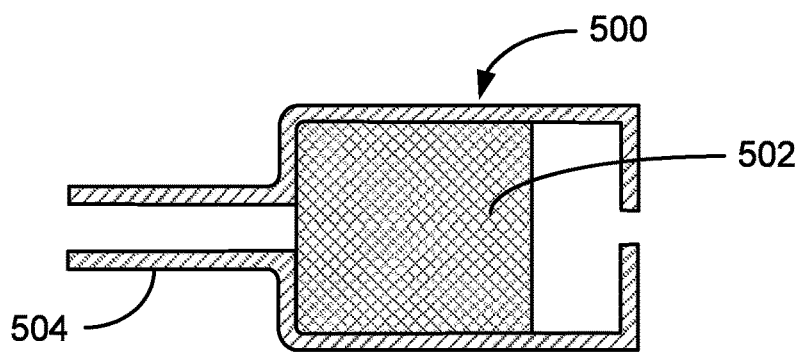
FIG. 5 illustrates another embodiment of an agent (e.g., nicotine) reservoir.

FIG. 5 illustrates another embodiment of a reservoir. An agent (e.g., nicotine) reservoir (500) can be a porous, open cell foam (502) within a cartridge; a tube, e.g., capillary tube (504) can extend from the reservoir.

Figure 6:
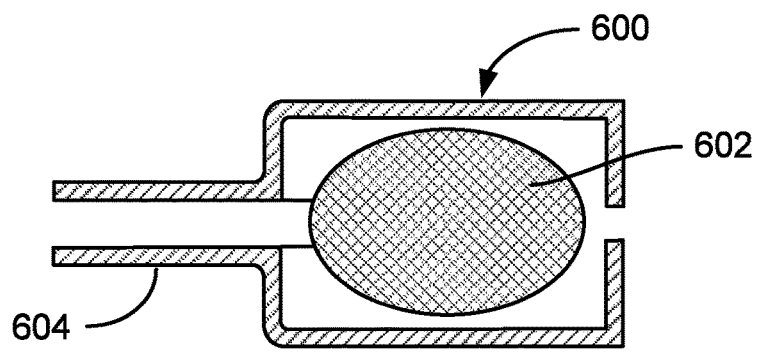
FIG. 6 illustrates another embodiment of an agent (e.g., nicotine) reservoir.

FIG. 6 illustrates another embodiment of an agent (e.g., nicotine) reservoir. The mixture can be held in a collapsible bag (602) which can be held within a secondary container (600). A tube, e.g., capillary tube (604) can extend from the reservoir.

In one embodiment, doses of a liquid agent (e.g., liquid nicotine) are held in a safe dose cartridge container until needed. A container for an agent (e.g., nicotine) can comprise a sealing mechanism that can keep the agent (e.g., nicotine) in the container even if the container is crushed. In one embodiment, the sealing mechanism comprises septum sealing. Methods are provided herein for safely puncturing and reclosing access to a drug (e.g., nicotine) cartridge. In one embodiment, a septum and a puncturing needle is used to extract an agent (e.g., nicotine) from a cartridge. A semi-porous material can be used to ensure that the rate of agent (e.g., nicotine) transfer is safe. For example, materials can include a frit or other material (e.g., ceramic, foam, or metal) that has a convoluted or open structure.

In one embodiment, a device comprises a dose cartridge, or a disposable dose cartridge. In another embodiment, the dose cartridge houses an agent (e.g., nicotine) formulation and an aerosol creation mechanism as described herein. In one embodiment, the dose cartridge comprises a reservoir comprising an agent (e.g., nicotine) formulation, optionally with a dispensing tube, e.g., capillary tube, for dispensing the agent (e.g., nicotine) formulation. In another embodiment, the dose cartridge has a mouthpiece comprising a cap to help prevent contamination, provide a tamper resistance feature, or provide a child resistance feature. In one embodiment, the cap covers both the mouthpiece and any air inlets. In another embodiment, the cap is reusable.

In one embodiment, the dose cartridge comprises a heater element, such as metal foil made of stainless steel or any other electrically resistive material. In one embodiment, the heater element comprises a coil of wire or wire coil which can be from about 0.12 to about 0.5 mm in diameter. In one embodiment, the dose cartridge comprises two heater elements.

Tube, e.g., Capillary Tube

Figure 1:
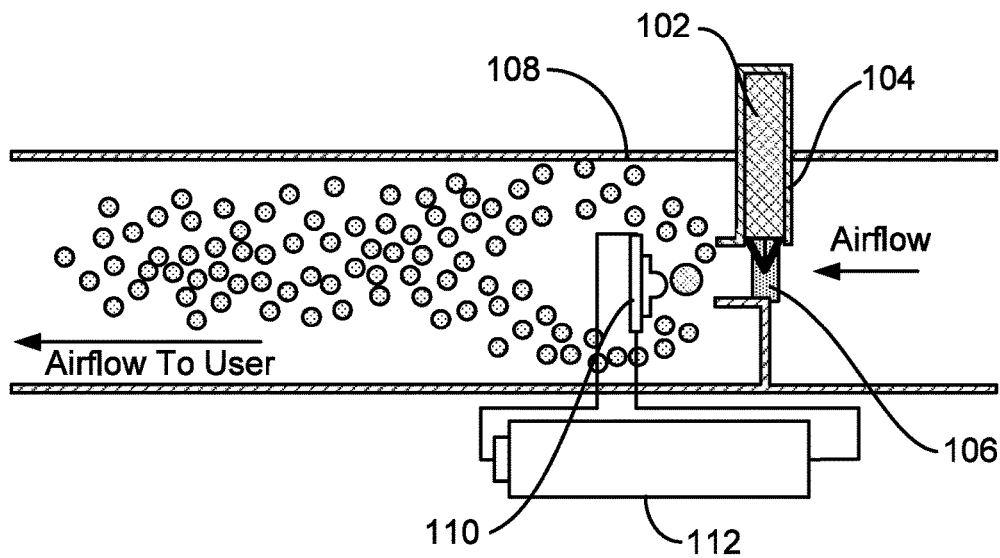
FIG. 1 illustrates an embodiment of an electronic nicotine delivery device.
Figure 2A:
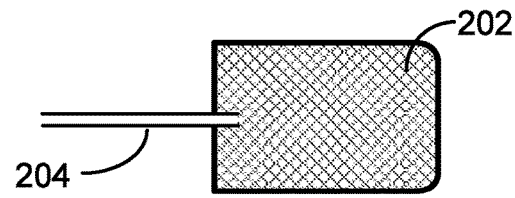
FIGS. 2A and 2B illustrate an embodiment of electronic agent (e.g., nicotine) delivery device.
Figure 2B:
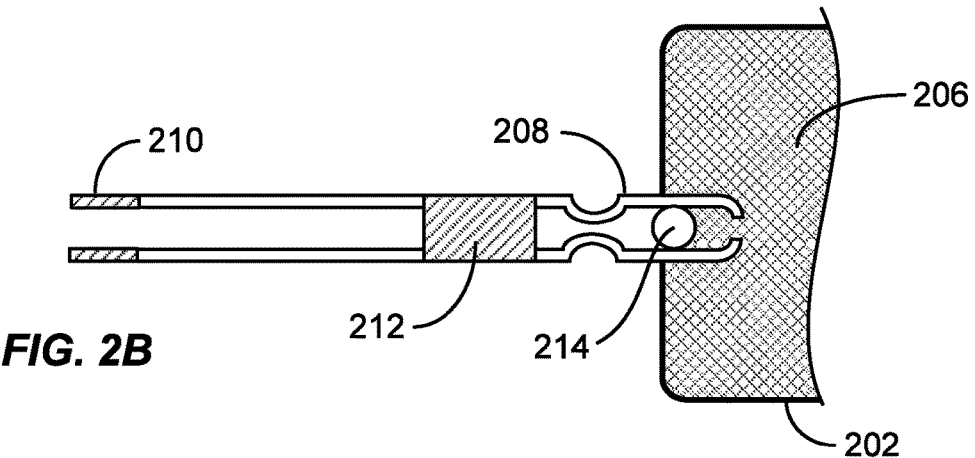
Figure 3A:
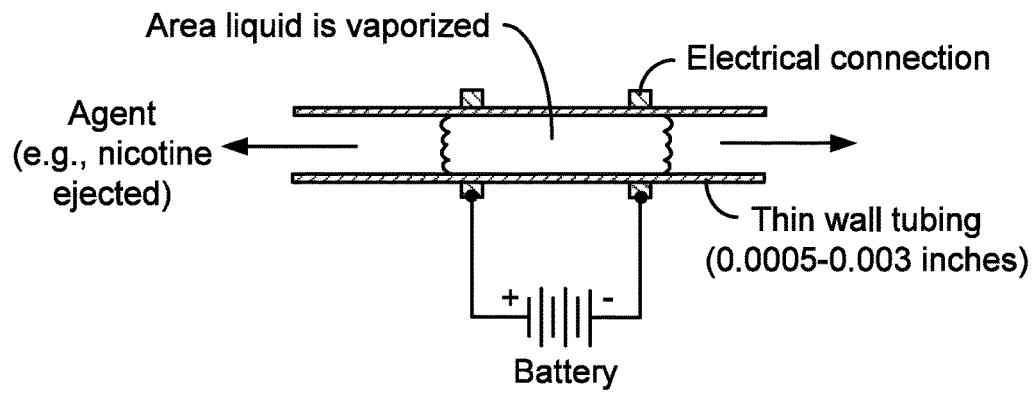
FIGS. 3A and 3B illustrate embodiments of a heater element.
Figure 3B:
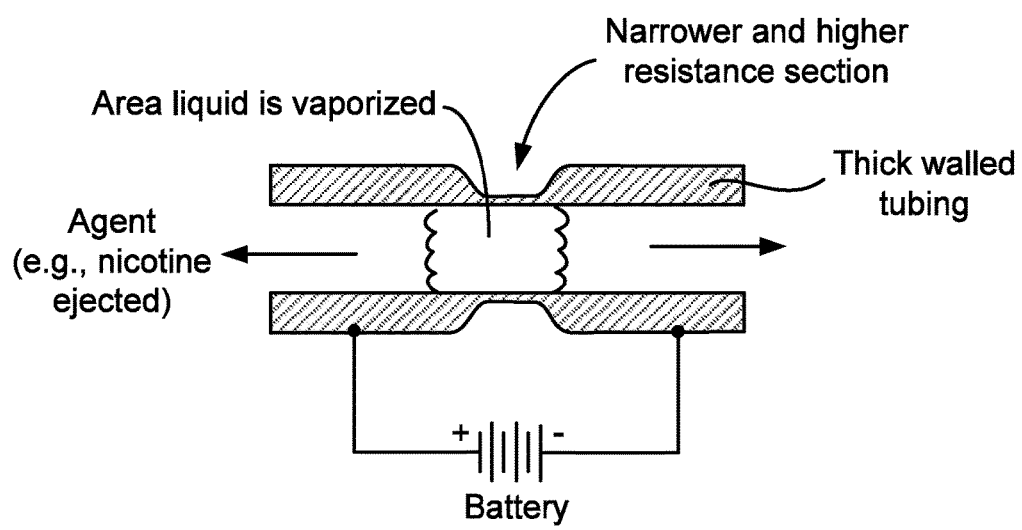

FIGS. 2A and 2B illustrate embodiments of components of an electronic nicotine delivery device. FIG. 2A illustrates an agent (e.g., nicotine) reservoir (202) and a tube, e.g., capillary tube (204). FIG. 2B illustrates an expanded view of the device. The agent (e.g., nicotine) reservoir can comprise an agent (e.g., nicotine)/propylene glycol (PG) mixture (206). The tube, e.g., capillary tube can comprise a region on the interior which has been coated with an agent (e.g., nicotine)/PG philic material (208) to promote wicking out of a reservoir. A region on the interior which has been coated with an agent (e.g., nicotine)/PG phobic material (210) (such as polytetrafluoroethylene (PTFE)) can lie at the open end. This coating can cause the agent (e.g., nicotine)/PG to stop wicking short of the open end, thereby reducing the surface area of the mixture exposed to air, and air devoid of agent (e.g., nicotine) vapor. The tube, e.g., capillary tube can comprise a heated section (212) of the tube, e.g., capillary tube which, upon heating, can cause the mixture in the tube to vaporize and expand, pushing the mixture from the open end. A ball valve (214) can be trapped between two indentations in the tube, e.g., capillary tube, the end indentation being such that the ball, if pushed by fluid, will form a seal. This configuration can allow the liquid to be ejected from the end upon heating rather than back into the reservoir. All four of these elements can form a pump which can eject a known dose of the mixture from the end of the tube, e.g., capillary tube.

To eject a dose of an agent (e.g., nicotine)/PG mix with a 1:10 ratio, 1 mm$^3$ of material can be in the tube, e.g., capillary tube. For a tube, e.g., capillary tube with an interior diameter of 0.5 mm, the length can be ~5 mm.

Valve

A valve can be a check valve, and the check valve can be a ball which can be made of a metal, such as stainless steel or can be made of a plastic, such as nylon, delrin, or a homopolymer acetal. The ball can have a diameter less than the interior diameter of the tube, e.g., capillary tube sufficient to allow an agent (e.g., nicotine)/PG mix to wick by it.

Heater Element

A heater element can be any heater element as provided herein. The heater element can be used to generate a condensation aerosol from a liquid formulation comprising a pharmaceutically active agent as provided herein. The condensation aerosol can comprise particles of a size suitable for delivery to the lungs of a subject as provided herein. In some cases, the heater element comprises a coil. The coil can be a wire coil. The coil can further comprise a wick element capable of being heated. The heater element can vaporize the liquid formulation when the liquid formulation is delivered to the heater element. In some cases, the liquid formulation comprising a pharmaceutically active agent (e.g., nicotine) is delivered to the heater element through the use of a positive displacement pump. The positive displacement pump can be a reciprocating, metering, rotary-type, hydraulic, peristaltic, gear, screw, flexible impeller, diaphragm, piston, or progressive cavity pump, or any other pump utilizing positive displacement as known in the art. The positive displacement pump can be in fluid communication with the heater element. The positive displacement pump can be in fluid communication or fluidically coupled to a reservoir comprising a pharmaceutically active agent (e.g., nicotine). The positive displacement pump can be in fluid communication with the heater element and a reservoir comprising a pharmaceutically active agent (e.g., nicotine). The pharmaceutically active agent (e.g., nicotine) can be a liquid formulation. The positive displacement pump can be within the passageway or external to the passageway. The heater element can comprise a rod comprising electrically resistive material. The rod can be a wire. The rod can be a pliable rod. The rod can comprise a coil, wherein a segment of the rod can pass through the interior of the coil. The coil can be a wire coil. The heater element can comprise a wick element capable of being heated. The wick element capable of being heated can pass through and exit the center of the coil. In some cases the heater element comprises a heatable wick element. The rod can comprise the heatable wick element. In some cases, the rod comprises a coil and a heatable wick element, wherein the heatable wick element is a segment of the rod that passes through the interior or center of the coil.

FIGS. 3A and 3B illustrate configurations of a heater element. The tube, e.g., capillary tube can be made of stainless steel, or a similar matter, which has an electrical resistance substantially greater than other metals (aluminum, brass, iron). The tube, e.g., capillary tube can be made of a thin wall material (FIG. 3A), or a section of the wall can be narrowed (FIG. 3B) to result in that section having an electrical resistance such that when an electrical current is passed across the section heating happens. Alternately the tube, e.g., capillary tube can be wrapped with a heater wire. This configuration can allow for the tube, e.g., capillary tube to be made of a non-electrically conductive material such as Kapton (polyimide), which can withstand heat. Electrical heating can be powered directly from a battery or can be powered from a charged capacitor.

A heater element can be used to vaporize an agent (e.g., nicotine)/PG mixture to form an aerosol with a particle size (MMAD=Mass Median Aerodynamic Diameter) of about 1 to about 5 μm. Aerosols with this particle size can deposit in the deep lung and result in rapid PK.

Figure 7:
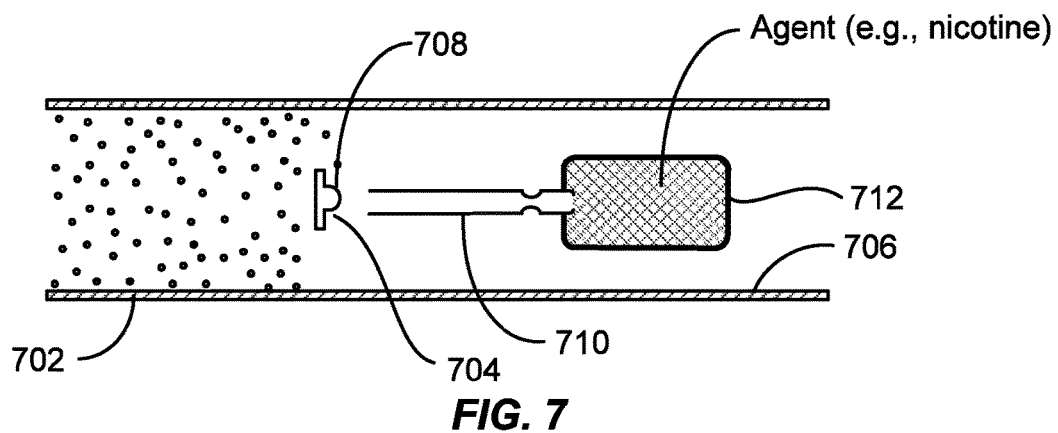
FIG. 7 illustrates an embodiment of a heater element.
Figure 8:
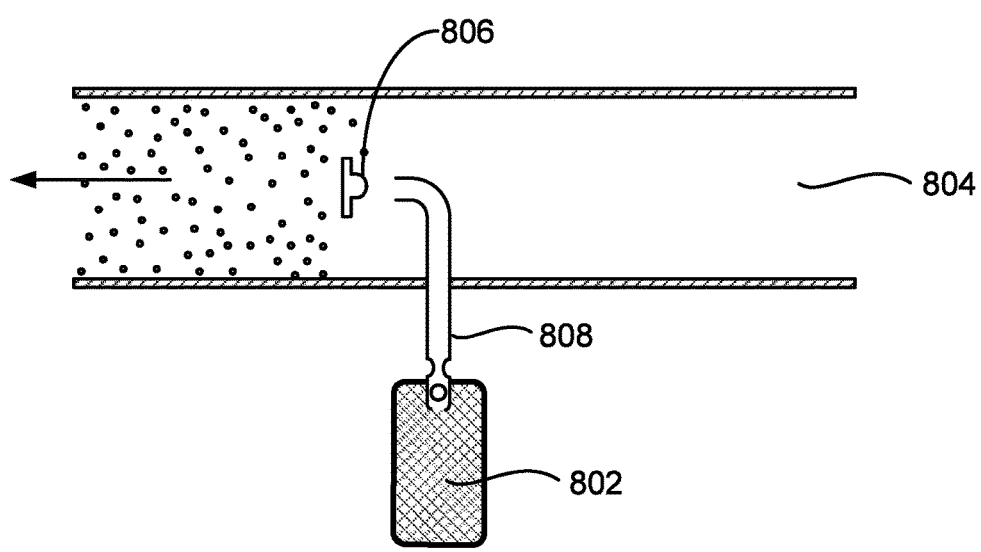
FIG. 8 illustrates an embodiment of an electronic agent (e.g., nicotine) delivery device.

FIG. 7 illustrates a configuration of a heater element (704) in an airway (706). The heater element can be made of a thin stainless steel foil. The foil can be of a thickness of about 0.0005 to about 0.005 inches (a range from about 0.01 mm to about 0.13 mm) thick, or from about 0.0005 to about 0.001 inches (a range from about 0.01 mm to about 0.025 mm) so that less electrical current is needed to vaporize the mixture. The foil can be of a thickness of about, less than, more than, at least or at most 0.0005, 0.0006, 0.0007, 0.0008, 0.0009, 0.001, 0.002, 0.003, 0.003, 0.004, or 0.005 inches (a range from about 0.01 mm to about 0.13 mm). The heater element (704) can be positioned at the exit of the tube, e.g., capillary tube (710) so that the mixture can deposit (708) on the heater element (704). The heater element (704) can be positioned in an airway (706) so that a user upon inhalation can cause the aerosol to pass through the mouthpiece (702) and be drawn into the lungs. The agent (e.g., nicotine) reservoir (712) can be in the airway. FIG. 8 illustrates that in some cases, an agent (e.g., nicotine) reservoir (802) can be placed outside of an airway (804), while the heater element (806) can be in the airway (804). A tube, e.g., capillary tube (808) can enter the airway (804).

Figures 31A, 31B:
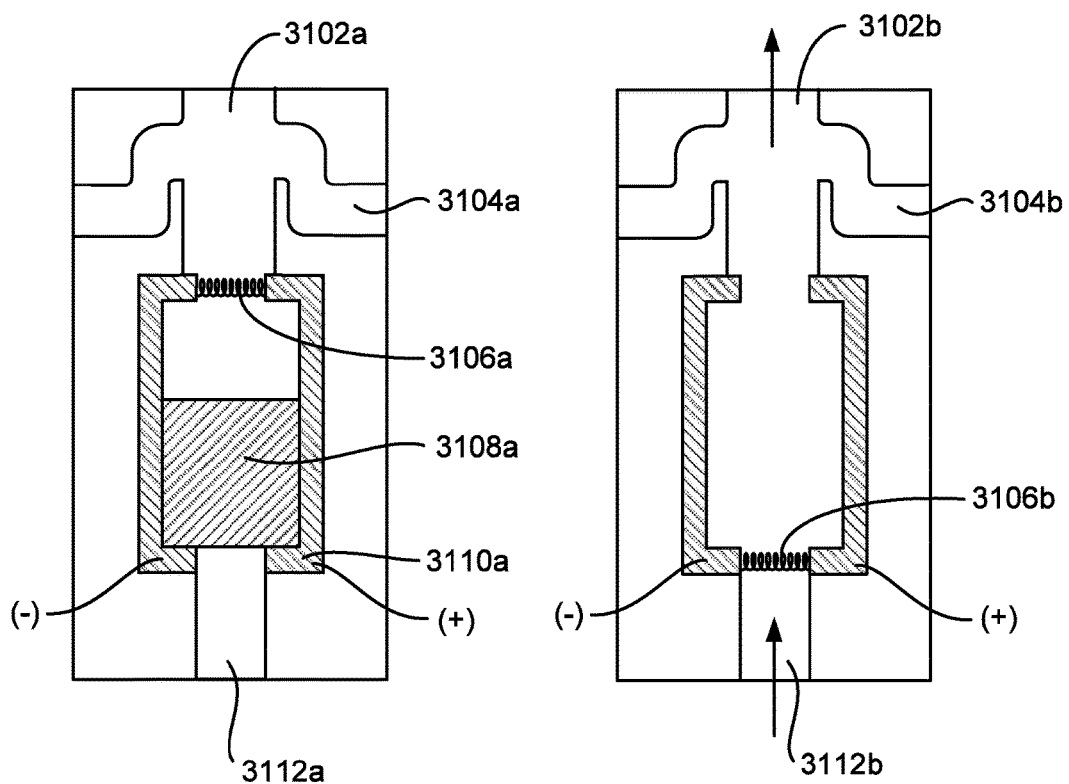
Figure 31C:
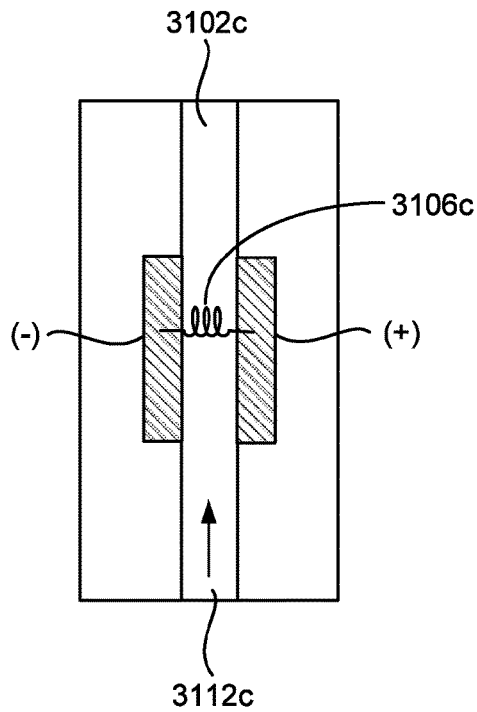
Figure 31D:
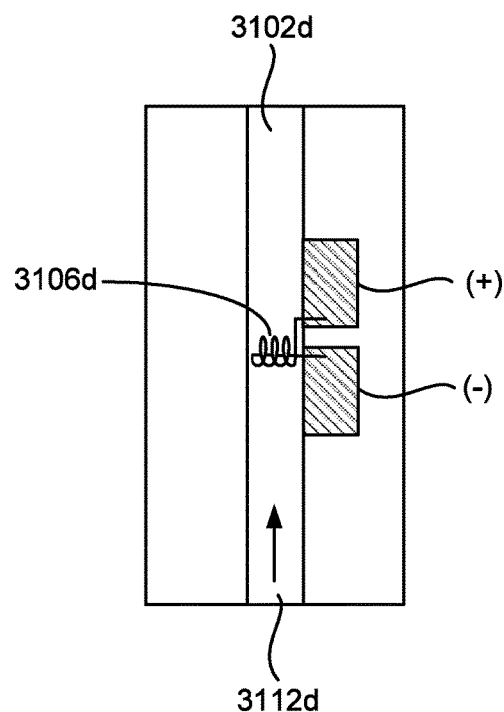
Figure 31E:
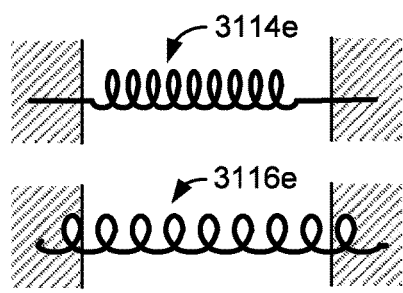

FIGS. 31A-D illustrates another configuration of a heater element (3106*a-d*) in an airway (3112*a-d*). FIG. 31A depicts a device (ENT-100-A), comprising a primary carrier gas inlet (3112*a*), positive and negative brass contacts (3110*a*), a heater element (3106*a*) comprising a coil located distally from the inlet to the primary airway (3112*a*) and two bypass inlets (3104*a*) located (disposed) downstream of the heater element but prior to the outlet (3102*a*). FIG. 31B depicts a device designated ENT-100-B, which is the same as ENT-100-A except that the heater element has been moved to be proximal to the inlet of the primary airway (3112*b*). FIG. 31C depicts a device designated ENT-100-C, which is similar to the ENT-100-A device except that the wire coil heater element has been moved to an intermediate position relative to the location of the coil in ENT-100-A and ENT-100-B. Any of the devices depicted in FIG. 31A-C can comprise the wire coil heater element designated "A Coil" (3114*e*) or "B Coil" (3116*e*) as illustrated in FIG. 31E. The coil in both types of heater elements comprise inner diameter of 0.26 inches (about 6.6 mm). The "A Coil" comprises a stretch of coil followed by a straight lead on either end of the coil which connects to the brass contacts. The "B Coil" comprises a stretch of coil, wherein the coil itself connects to the brass contacts. FIG. 31D depicts a device designated ENT-100-D with a primary passageway (3112*d*) for air to flow through, brass contacts (+1-) embedded within the wall of the primary passageway, and a heater element (3106*d*) comprising a wire wherein one end of the wire wraps around another segment of the wire, wherein a wire coil is formed with an end of the wire passes through the center of the wire coil. An example of this type of heater element is shown in FIGS. 36-38. In some cases, a liquid formulation comprising a pharmaceutically active agent (e.g., nicotine) is delivered to the heater element of FIGS. 31A-D from a reservoir comprising the liquid formulation comprising a pharmaceutically active agent (e.g., nicotine) through the use of a tube, e.g., capillary tube as provided herein, wherein the tube, e.g., capillary tube is coupled or capable of being coupled to the reservoir. In some cases, a liquid formulation comprising a pharmaceutically active agent (e.g., nicotine) is delivered to the heater element of FIGS. 31A-D from a reservoir comprising the liquid formulation comprising a pharmaceutically active agent (e.g., nicotine) through the use of a positive displacement pump as provided herein, wherein the positive displacement pump is fluidically coupled to the reservoir.

Figure 9:
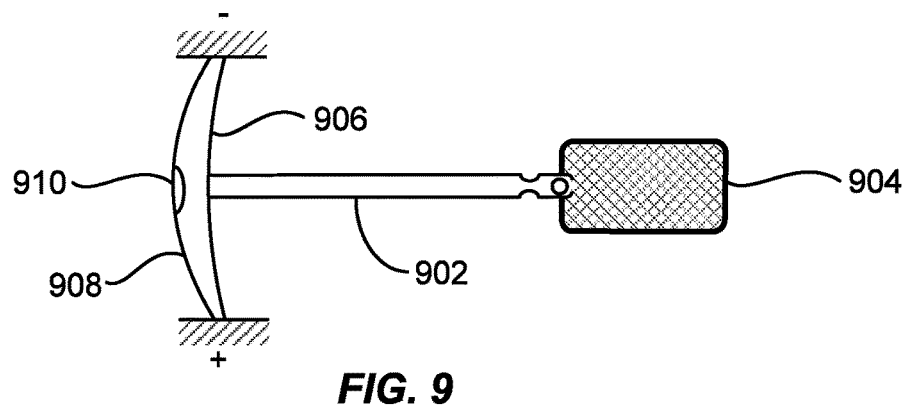
FIG. 9 illustrates another embodiment of a heater element.

FIG. 9 illustrates another embodiment for a heater element. To aid in reducing an agent (e.g., nicotine) from evaporating from the end of a tube, e.g., capillary tube (902) (attached to an agent (e.g., nicotine) reservoir (904)), the heater element (906) can be positioned to cover the end of the tube, e.g., capillary tube when cold. Upon heating the heater would move away from the end (908) due to thermal expansion, opening up the end and allowing the mixture to leave. The position of deposited material (910) is shown.

Figure 10A:
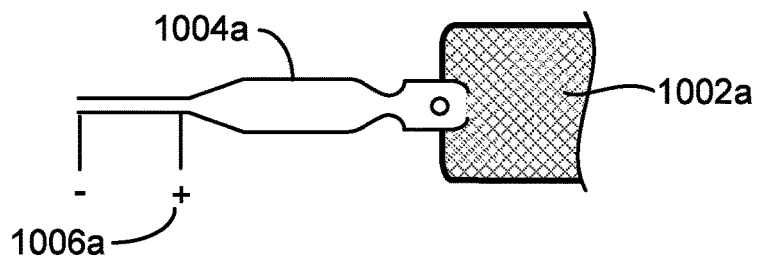
FIGS. 10A and 10B illustrate additional embodiments of a heater element.
Figure 10B:
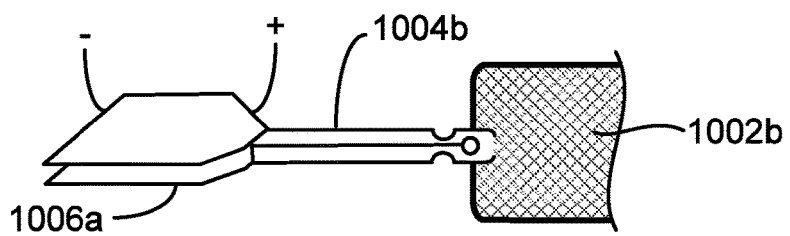

FIGS. 10A and 10B illustrate additional configurations of a heater element. FIG. 10A illustrates that a heater element (1006*a*) can be positioned at the end of the tube, e.g., capillary tube (1004*a*), where the tube, e.g., capillary tube can be attached to an agent (e.g., nicotine) reservoir (1002*a*). FIG. 10B illustrates an agent (e.g., nicotine) reservoir (1002*b*) and a tube, e.g., capillary tube (1004*b*), where the geometry of the tube, e.g., capillary tube is modified at the end (1006*b*) by narrowing or flattening to aid in vaporization.

FIG. 22 illustrates another embodiment of a heater element. The heater element (2200) can be a rod comprising a coil (2202) that can be made of stainless steel, or a similar matter, which has an electrical resistance substantially greater than other metals (aluminum, brass, iron). In some cases, the rod is a wire, wherein the coil is a wire coil. The rod can comprise an electrically resistive material. The electrically resistive material can have an electrical resistance such that when an electrical current is passed across the rod heating happens. The rod is connected to brass contacts (2204) through segments of the rod that do not form the coil. In some cases, the segments of the rod that connect to the brass contacts comprise leads. The brass contacts can serve to pass electrical current across the rod, including the coil. The electrical current can serve to heat the coil and vaporize material (i.e. an agent (e.g., nicotine) mixture) that contacts or is delivered to the coil. The coil can be an open coil that can allow for air to flow between the coils and carry away the vaporized material. In FIG. 22, the brass contacts (2204) are located (disposed) on either side of an airflow channel and the rod, including the coil, span the channel. In some cases, the coil can be oriented parallel to the flow of a carrier gas (e.g., air). In some cases, the coil can be oriented perpendicular to the flow of a carrier gas (e.g., air). In FIG. 22, a tube, e.g., capillary tube (2206) attached to a reservoir (2208) comprising an agent (e.g., nicotine) mixture is located at one end of the coil and an agent (e.g., nicotine) mixture is dispensed from the end of the tube, e.g., capillary tube onto the coil. The agent (e.g., nicotine) mixture, once dispensed, can wick along the coil to cover the entire or part of the coil. The coil can be heated which can vaporize the agent (e.g., nicotine) mixture.

FIGS. 36-38 illustrate yet another embodiment of a heater element. In this embodiment, a first (3602*a*; +) and a second (3602*b*; –) brass contact or terminal are located adjacent to each other. The brass contacts can be embedded within or placed proximal to a wall of a housing or channel of a device for generating an aerosol as provided herein. The heater element can be a rod comprising electrically resistive material, wherein a first end or lead (3604*a*) is connected to one brass contact (3602a; +), while a second end or lead (3604b) is connected to another, separate brass contact (3602b; −). As illustrated in FIG. 36, a portion or segment of the rod between the leads is configured into a coil (3606). In addition, a separate portion or segment (3608) of the rod passes through the interior of the coil (3606). Supplying current to the rod through the brass contacts (3602a,b) can serve to heat both the coil (3606) as well as the segment (3608) of the rod that passes through the interior of the coil (3606). In some cases, the segment of the rod that runs through the center of the coil is capable of holding a liquid formulation comprising an agent (i.e. nicotine) as provided herein. The liquid formulation can wick or be delivered by any of dosing mechanisms provided herein onto the segment of the rod that runs through the center of the coil from a source of the liquid formulation (e.g., a reservoir). In some cases, supplying current to the rod through the brass contacts (3602a,b) serves to heat both the coil (3606) as well as the segment (3608) of the rod that passes through the interior of the coil (3606), wherein a liquid formulations that wicks or is delivered by any of dosing mechanisms provided herein onto the segment of the rod running through the coil is vaporized. In FIG. 36, the coil is oriented perpendicular to the flow of a carrier gas (e.g. air flow) (3610). In some cases, the coil is oriented parallel to the flow of a carrier gas (e.g. air flow) in a device for generating a condensation aerosol as described herein. FIGS. 37A and 37B depict alternate embodiments to the heater element illustrated in FIG. 36, wherein the number of coils shown in the heater element of FIG. 37A is reduced in the heater element of FIG. 37B. As shown in FIG. 37, alternating the number of coils (3702b, 3702b) in the coil serves to increase the length of the non-coil segments (3704a, 3704b) of the rod and decrease the length of the rod covered by the coil. FIG. 38 illustrates components of the rod and coil in the heater element illustrated in FIG. 36, including the diameter of the rod (3802), total length of the coil (3804) (e.g., 0.1 to 0.15 inches (a range from about 2.54 mm to about 3.81 mm)), inner diameter of the coil (3808) (e.g., 0.027-0.040 inches (about 0.6 mm to about 1.02 mm)), outer diameter of the coil (3806) (e.g., 0.047-0.06 inches (a range from about 1.19 mm to about 1.53 mm)), and pitch of the coil (3810).

Removal of Particles

Figure 11:
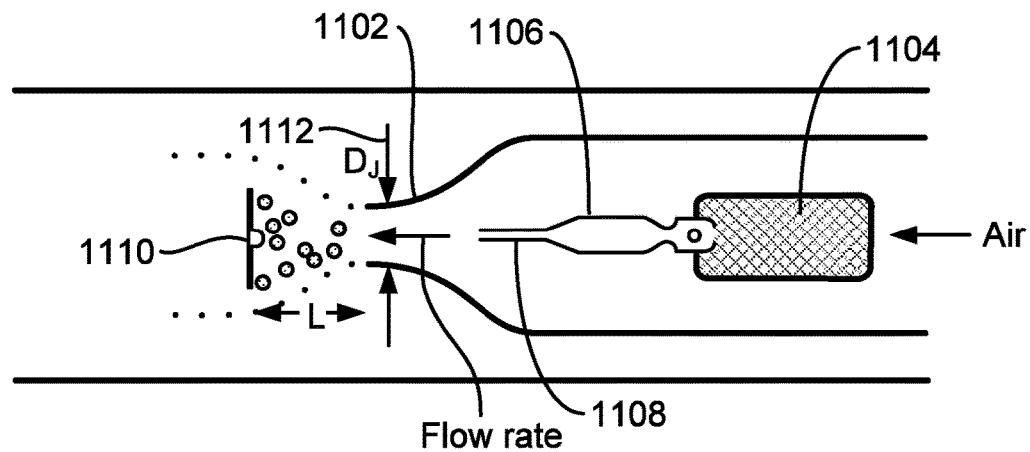
FIG. 11 illustrates inertial impaction.

In some cases, an issue with vaporization within the capillary can arise. First, liquid droplets can be ejected by vapor pushing the material out. Second, because the high vapor concentration can be high within the capillary end, rapid condensation and aggregation leading to larger than optimum particle size can result. To reduce the particle size of the aerosol the large particles can be removed and revaporized. Removal can be accomplished thru inertial impaction (FIG. 11). FIG. 11 shows an agent (e.g., nicotine) reservoir (1104), tube, e.g., capillary tube (1106), heater element 1 (1108), and a heater element 2 (1110). One consideration is whether a restriction in a nozzle (1102) can cause an unacceptable increase in the air flow resistance. The following formula can be used to calculate the diameter of an orifice ($D_J$) (1112).

$$d_{50}\sqrt{C_c} = \left[\frac{9\pi N D_J^3 (Stk_{50})}{4 P_p Q}\right]^{1/2}$$

Where $d_{50}$=is the average aerosol practice size.
Where:
N=viscosity (of air)=1.81×10⁻⁵ $P_a$ sec
$D_J$=The nozzle diameter in meters $Stk_{50}$=Stokes number for a round nozzle=0.24 (dimensionless)
$P_p$=Density of particle, for liquids assumed to be 1000 kg/meter³
Q=Flow rate in liters/mixture (assume 15 L/min (about 2.5×10⁻⁴ m³/s))

Additionally to correct for slip factor the following equation can be used:

$$d_{50}=d_{50}\sqrt{C_c}-0.078 \text{ in microns}$$

Using the above, a table of nozzle sizes vs. particle sizes that will impact can be generated as shown in Table 1:

TABLE 1

| Nozzle Size (mm) | Particle Size (μm) |
|---|---|
| 7 | 6.41 |
| 6 | 5.07 |
| 5 | 3.84 |
| 4 | 2.72 |

If a particle size of approximately 5 μm is desired, a nozzle with a diameter of about 6 mm can be used, which can be acceptable for a pressure drop at 15 L/min (about 2.5×10⁻⁴ m³/s) flow rate of inhalation.

A device for generating a condensation aerosol from a liquid formulation comprising a pharmaceutically active agent (e.g., nicotine) as provided herein comprises a means for removing aerosol particles of a size not optimal for deep lung delivery and subsequent rapid PK. The non-optimal particles can have an MMAD of greater than 5 μm. The means for removing the non-optimal particles can be a solid structure within a passageway in which a condensation aerosol generated as provided herein flows. In some cases, the structure is a planar surface attached to one or more walls of the passageway, wherein the planar structure comprises one or more holes wherein particles of specific sizes (e.g. less than 5 μm) pass through. In some cases, the structure comprises a planar surface attached to the passageway such that the planar surface has a diameter or width that occupies a portion of the diameter or width of the passageway such that only particles of an optimal size flow or are diverted around the planar surface while non-optimally sized particles impact the surface and are incapable of flowing around the surface. The optimally sized particles have an MMAD of less than or equal to 5 μm, an MMAD of about 1 to about 5 μm, or an MMAD of greater than 5 μm. The structure can be a baffle or baffle plate. FIGS. 44 A-C illustrate an embodiment of a passageway comprising a baffle for removing condensation aerosol particles whose size is not optimal for deep lung delivery and subsequent rapid PK. FIGS. 44A and B illustrate exterior views of the passageway comprising the baffle, while FIG. 44C provides an interior view of a cone shaped baffle (4402) and its orientation within a passageway through which a condensation aerosol flows (4410). In FIG. 44C, a condensation aerosol comprising a pharmaceutically active agent (e.g., nicotine) generated by any means as provided herein enters a portion of a passageway comprising the baffle (4402) through an aerosol inlet (4404). The aerosol inlet can be a portion of a passageway downstream of a heater element that narrows following the area of the passageway that comprises the heater element. The aerosol inlet (4404) serves to funnel the aerosol through a narrowed passageway prior to the aerosol encountering the planar surface of the cone-shaped baffle (4402). Prior to the baffle (4402), the passageway widens, wherein the diameter of the planar surface of the baffle occupies a substantial portion of the diameter of the widened passageway. Upon entry into the widened passageway, the aerosol flows toward the baffle (4402), wherein large particles (>5 µm) flow into the planar surface of the baffle, while small particles (≤5 µm), flow around the edges of the baffle (4402). As the small particles flow around the baffle (4402), they flow into a wider passageway towards the outlet (4406) of the passageway. The widened passageway downstream of the baffle (4402) entrains the small particles into additional carrier gas (4408) that enters through secondary carrier gas (4408) inlets. In some cases, a flow of carrier gas through the passageway is about 1 to about 10 LPM (a range from about $1.667 \times 10^{-5}$ m$^3$/s to about $1.667 \times 10^{-4}$ m$^3$/s) (e.g., at a vacuum of about 1 to about 15 inches of water (a range from about 249 Pa to about 3738 Pa)), while the carrier gas (4408) entering through the secondary carrier gas (4408) inlets entrains the small particles in an air flow of about 20 to about 80 LPM (a range from about $3 \times 10^{-4}$ m$^3$/s to about $1.3 \times 10^{-3}$ m$^3$/s). In some cases, the passageway depicted in FIG. 44C is connected to and downstream of the passageways depicted in any one of FIGS. 31A-D, wherein the passageway depicted in FIG. 44C is connected at the aerosol inlet (4404). In some cases, the aerosol inlet of the passageway depicted in FIG. 44C is a downstream extension of the passageways depicted in any one of FIGS. 31A-D.

The inner diameter of the passageway at the aerosol inlet of FIG. 44C and downstream of the narrow channel can be can be exactly, about, more than, less than, at least or at most 0.2, 0.21, 0.22, 0.23, 0.24, 0.25, 0.26, 0.27, 0.28, 0.29, 0.3, 0.35, 0.4, 0.45, or 0.5 inches (a range from about 0.508 mm to about 12.7 mm).

Flow Regulation

A device provided herein can be configured to limit a flow of a carrier gas through the passageway or aerosol generation area/chamber to permit condensation of the vaporized liquid formulation. The carrier gas can be air. The flow of a carrier gas through the aerosol generation chamber or passageway comprising or in fluid communication with the heater element can be limited to about 1 to about 10 liters per minute (LPM) (a range from about $1.667 \times 10^{-5}$ m$^3$/s to about $1.667 \times 10^{-4}$ m$^3$/s). The device can be configured to comprise a flow resistance (to inhalation) of about 0.05 to about 0.15 sqrt (cm-H$_2$O)/LPM. The device can be configured to comprise an inhalation resistance comprising a vacuum pressure of about 1 to about 10 inches of H2O (a range from about 249 Pa to about 2488 Pa).

Figure 21:
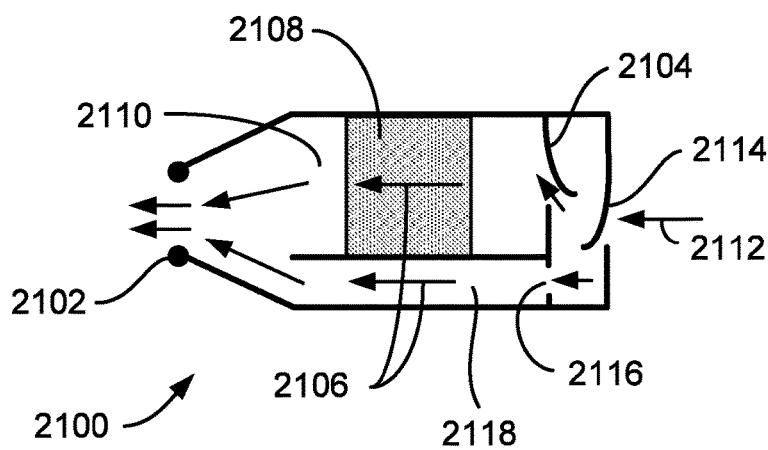
FIG. 21 illustrates an embodiment of a method for flow control.
Figure 22:
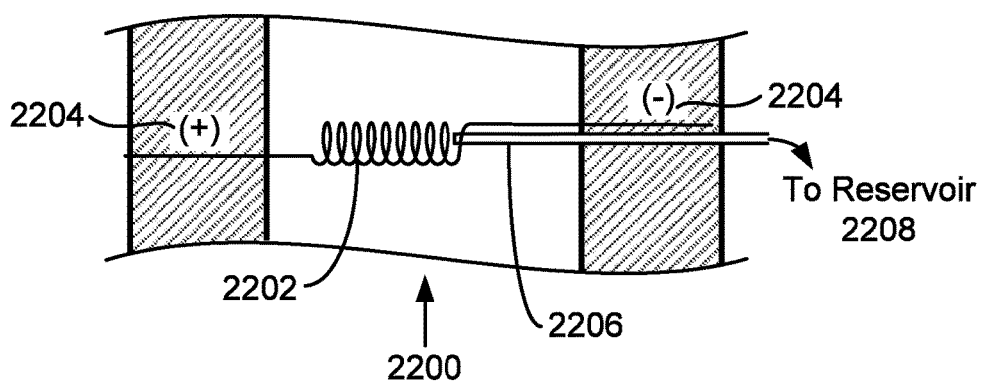
FIG. 22 illustrates an embodiment of a heater element.

FIG. 21 illustrates an embodiment of an electronic agent (e.g., nicotine) delivery device comprising a valve system (2100) for controlling air flow for deep lung delivery and rapid PK. Upon inhalation, negative pressure in a mouthpiece (2102) increases causing a pressure drop across a gas control valve (2104). An increase in the pressure drop can cause the valve (2104) to close and prevent airflow (2106) into an aerosol generating area (2108) within a flow through chamber (2110). The aerosol generating area (2108) can comprise an agent (e.g., nicotine) reservoir comprising an agent (e.g., nicotine) formulation, any of the dosing mechanisms described herein, and a heater for vaporizing an agent (e.g., nicotine) droplets that can be released from the dosing mechanism. Closing of the valve (2104) can subsequently cause an increase in airflow (2106) from an air inlet (2112) across a backflow valve (2114) through a diversion air orifice (2116) and into a diversion air channel (2118). In this manner, the airflow over a vaporizing agent (e.g., nicotine) formulation can be regulated and controlled to an optimal level in order to achieve optimum particle sizing and dosing effectiveness. In one embodiment, the valve system produces an inhalation resistance no greater than that of a cigarette. In one embodiment, the valve system produces an inhalation resistance no greater than 0.08 (cm H$_2$O)$^{1/2}$/LPM.

FIG. 32 A-E illustrates multiple embodiments of a device for regulating the flow of a carrier gas (e.g. air). In each embodiment, the device comprises a primary flow-through passageway (3202A-E) and one or more sources of bypass or additional carrier gas (3204A-E). In each embodiment, the one or more sources of bypass or additional carrier gas (3204A-E) permit an additional or bypass flow of carrier gas (e.g. air) to mix with the carrier gas flowing through the primary flow-through passageway (3202A-E). In some cases, the mixing occurs downstream of an aerosol generation chamber, thereby mixing a condensation aerosol produced in the aerosol generation chamber with a larger volume of carrier gas (e.g. air). The mixing can produce a total flow rate downstream of the mixing of about 20 to about 80 liters per minute (LPM) (a range from about $3 \times 10^{-4}$ m$^3$/s to about $1.3 \times 10^{-3}$ m$^3$/s). FIG. 32A shows a device comprising a primary flow-through passageway (3202*a*) comprising an upstream and downstream section comprising an inner diameter of 0.25 inches (about 6.35 mm), and two secondary flow-through chambers (3204*a*), wherein bypass or additional carrier gas enters the device through two inlets (3206*a*) adjacent to the primary flow-through chamber (3202*a*). The inner diameter of the primary flow through chamber (3202*a*) narrows just prior to entry of the bypass carrier gas. In some cases, the narrowing of the primary flow-through passageway permits formation of condensation aerosol particles comprising particles with an MMAD of about 1 to about 5 uM. The device in FIG. 32A can permit the mixing of the bypass carrier gas with the carrier gas flow through the primary chamber at a ratio of 10:1.

Figure 32A:
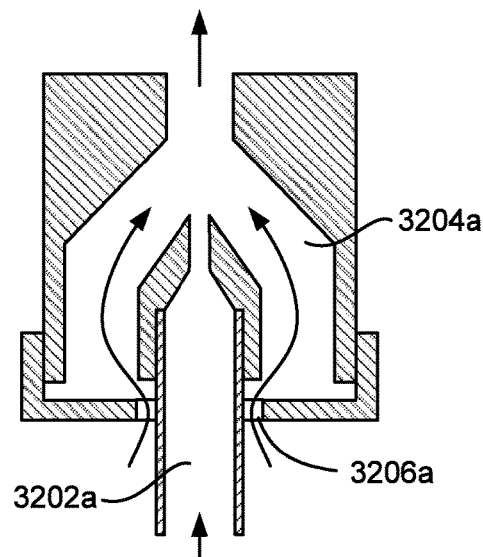
Figure 32B:
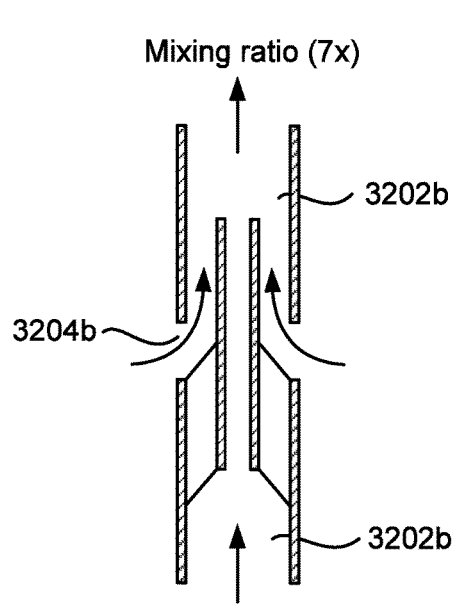

FIG. 32B shows a device comprising a primary flow-through passageway (3202*b*) comprising an upstream and downstream section comprising an inner diameter of 0.25 inches (about 6.35 mm), and two inlets (3204*b*) within the wall of the primary flow-through chamber (3202*b*), wherein bypass or additional carrier gas enters the device. The primary flow through chamber (3202*b*) narrows just prior to entry of the bypass carrier gas to comprise an inner diameter of 0.084 inches (about 2.13 mm) and an outer diameter of 0.108 inches (about 2.74 mm). In some cases, the narrowing of the primary flow-through passageway (3202*b*) permits formation of condensation aerosol particles comprising particles with an MMAD of about 1 to about 5 um. The device in FIG. 32B can permit the mixing of the bypass carrier gas with the carrier gas flow through the primary chamber at a ratio of 7:1.

Figure 32C:
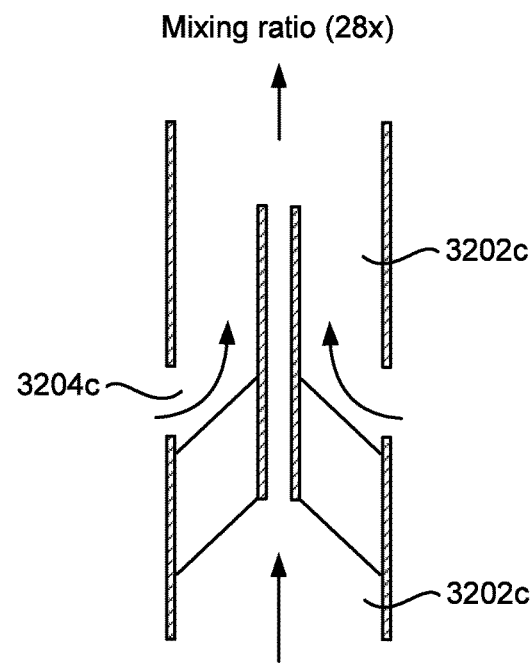

FIG. 32C shows a device comprising a primary flow-through passageway (3202*c*) comprising an upstream and downstream section comprising an inner diameter of 0.5 inches (about 12.7 mm), and two inlets (3204*c*) within the wall of the primary flow-through chamber (3202*c*), wherein bypass or additional carrier gas enters the device. The primary flow through chamber (3202*c*) narrows just prior to entry of the bypass carrier gas to comprise an inner diameter of 0.084 inches (about 2.13 mm) and an outer diameter of 0.108 inches (about 2.74 mm). In some cases, the narrowing of the primary flow-through passageway (3202*c*) permits formation of condensation aerosol particles comprising particles with an MMAD of about 1 to about 5 µm. The device in FIG. 32C can permit the mixing of the bypass carrier gas with the carrier gas flow through the primary chamber at a ratio of 28:1.

Figure 32D:
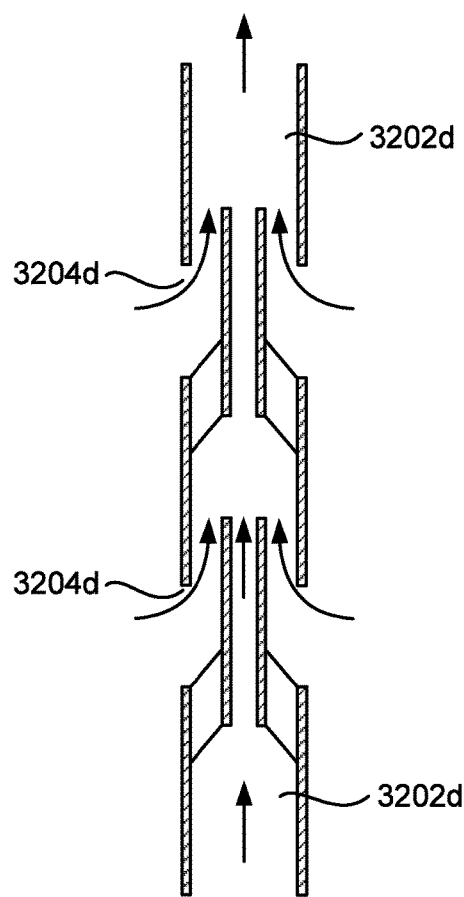

FIG. 32D shows a device comprising a primary flow-through passageway (3202d) comprising an upstream and downstream section comprising an inner diameter of 0.25 inches (about 6.35 mm), and two sets of two inlets (3204d) adjacent to the primary flow-through chamber (3202d), wherein bypass or additional carrier gas enters the device. The flow through chamber narrows just prior to entry of the bypass carrier gas from each set of two inlets to comprise an inner diameter of 0.096 inches (about 2.44 mm) and an outer diameter of 0.125 inches (about 3.175 mm). Following the first set of two inlets, the primary flow through passageway widens to an inner diameter of 0.250 inches (about 6.35 mm), before narrowing again. In some cases, the narrowing of the primary flow-through passageway permits formation of condensation aerosol particles comprising particles with an MMAD of about 1 to about 5 µm. The device in FIG. 32D can permit the mixing of the bypass carrier gas with the carrier gas flow through the primary chamber at a ratio of 35:1.

Figure 32E:
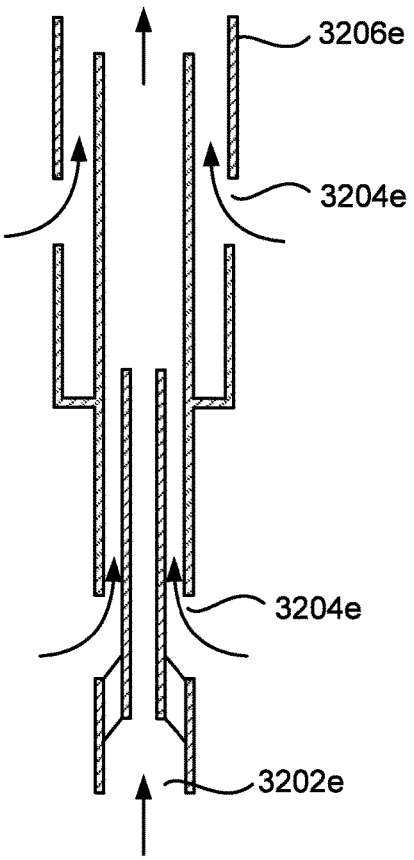

The device in FIG. 32E is similar to the device in FIG. 32D, wherein FIG. 32E shows a device comprising a primary flow-through passageway (3202e) comprising an upstream and downstream section comprising an inner diameter of 0.250 inches (about 6.35 mm), and two sets of two inlets (3204e) adjacent to the primary flow-through chamber (3202e), wherein bypass or additional carrier gas enters the device. The primary flow through chamber (3202e) narrows just prior to entry of the bypass carrier gas from the first set of two inlets to comprise an inner diameter of 0.096 inches (about 2.44 mm) and an outer diameter of 0.125 inches (about 3.175 mm). Following the first set of two inlets, the primary flow through passageway (3202e) widens to an inner diameter of 0.250 inches (about 6.35 mm) and an out diameter of 0.280 inches (about 7.112 mm). Subsequently, the primary flow-through passageway (3202e) opens into a secondary housing (3206e), which has an inner diameter of 0.466 inches (about 11.8 mm). In FIG. 32E, the second pair of inlets (3204e) are located in the wall of a secondary housing (3206e), which is coupled to and encompasses the primary flow-through passageway.

FIG. 33 illustrates another embodiment of a device for regulating the flow of a carrier gas (e.g. air). FIG. 33 shows a device comprising a primary flow-through passageway (3302) comprising an upstream and downstream section comprising an inner diameter of 0.25 inches (about 6.35 mm), and two inlets (3306) within the wall of the primary flow-through chamber (3302), wherein bypass or additional carrier gas enters the device. The primary flow-through chamber narrows (3302) just prior to entry of the bypass carrier gas to comprise an inner diameter of 0.086 inches (about 2.18 mm) and an outer diameter of 0.106 inches (about 2.69 mm). As depicted in FIG. 33, the section of the primary flow-through chamber (3302) is coupled to and encased by a secondary housing (3308). The secondary housing comprises a bypass inlet (3304), which permits entry of bypass or additional carrier gas (e.g. air) to enter the primary flow-through passageway through the inlets (3306). In some cases, the narrowing of the primary flow-through passageway permits formation of condensation aerosol particles comprising particles with an MMAD of about 1 to about 5 µm.

FIG. 35 illustrates another embodiment a device for regulating the flow of a carrier gas (e.g. air). The device comprises a primary airway (3504) that comprises an aerosol generation chamber (3528) comprising a heater element (3502), a restrictive orifice (3514) and a mouthpiece (3506). The heater element (3502) comprises a coil. The heater element can be any heater element comprising a coil as provided herein. The primary airway (3504) is fluidically connected to a secondary airway (3516), through a first channel (3518) located (disposed) between the restrictive orifice (3514) and heater element (3502), and a second channel (3520) located (disposed) between the heater element (3502) and the mouthpiece (3506). The secondary airway (3516) further comprises a third channel (3530) that is a secondary inlet (3508) for a carrier gas (e.g. air) and a diaphragm (3510). The diaphragm (3510) comprises a base member that is connected to a pair of springs (3512) on a first side and a protruding member (3524) on a second side. The springs (3512) are additionally connected to a wall opposite the first side of the base member that is part of the housing of the secondary airway (3516). The base member of the diaphragm (3510) is also connected to a pair of lateral springs (3526) on its lateral edges, which are further connected to the walls of the housing of the secondary airway (3516) opposite the lateral edges of the base member. The restrictive orifice (3514) is configured to limit the flow rate of the carrier gas (e.g. air) through the aerosol generation chamber (3528) in order to allow for the condensation of a liquid formulation comprising a pharmaceutically active agent as provided herein vaporized by the heater element (3502) to particles comprising about 1 to about 5 urn MMAD. The restrictive orifice (3514) limits the flow rate of the carrier gas (i.e. air) about 1 to about 10 liters per minute (LPM) (a range from about $1.667 \times 10^{-5}$ m$^3$/s to about $1.667 \times 10^{-4}$ m$^3$/s) at, e.g., a vacuum of about 1 to about 15 inches of water (a range from about 249 Pa to about 3738 Pa). Inhalation through the mouthpiece (3506) can produce a flow of carrier gas (e.g. air) through the restrictive orifice (3514) that can produce an inhalation resistance. The inhalation resistance produces a pressure differential across the opening of the first channel (3518) connecting the primary airway (3504) with the secondary airway (3516). The inhalation resistance causes the springs (3512) coupled to the first side of the diaphragm (3510) to compress and the lateral springs (3526) coupled to the lateral edges of the diaphragm (3510) to extend, whereby the protruding member of coupled to the second side of the diaphragm (3510) is removed from the third channel (3530) of the secondary airway (3516). Removal of the protruding member (3524) causes an additional flow of carrier gas (e.g. air) to enter the device. The additional flow of carrier gas (e.g. air) then enters the primary airway (3504) downstream of the heater element (3502) and aerosol generation area (3528) through the second channel (3520). The additional flow of carrier gas (e.g. air) can serve to mix or entrain the condensation aerosol comprising particles of about 1 to about 5 µm to produce a total flow rate suitable for delivery of the particles to the deep lung of a user of the device.

The one or more sources of additional or bypass carrier gas (e.g. air) can be configured to limit the flow rate of additional or bypass carrier gas to produce a total flow rate as provided herein. The flow rate can be limited by using a restrictive orifice on the one or more sources of additional or bypass carrier gas (e.g. air). The restrictive orifice can comprise any valve or flap as known in the art. The valve or flap can be moderated at specific flow rates. The flow rates that moderate the valve or flap can be the limited to flow rates provided herein. The valve or flap can be opened at specific inhalation resistance levels. The restrictive orifice can be opened at inhalation resistances comprising a vacuum of about 1 to about 10 inches of water (a range from about 249 Pa to about 2488 Pa).

The flow rate can be limited by using a restrictive orifice on the inlet for a carrier gas (e.g. air). The restrictive orifice can comprise any valve or flap as known in the art. The valve or flap can be moderated at specific flow rates. The flow rates that moderate the valve or flap can be the limited flow rates provided herein. The valve or flap can be opened at specific inhalation resistance levels. The restrictive orifice can be opened at inhalation resistances comprising a vacuum of about 1 to about 10 inches of water (a range from about 249 Pa to about 2488 Pa). The restrictive orifice can be configured to limit the flow rates to flow rates as provided herein. The restrictive orifice can be configured into a slot as depicted in FIG. 30B. An aerosol generation area or heater element as provided herein can be within a flow-through passageway. The flow-through passageway can be a primary flow through passageway.

Device Dimensions

In some cases, an electronic agent (e.g., nicotine) delivery device comprises the dimensions of an electronic cigarette with an overall cyclindrical shape to resemble a combustible cigarette.

"About" can mean a referenced numeric indication plus or minus 10% of that referenced numeric indication. For example, the term about 4 can include a range of 3.6 to 4.4.

FIG. 39 illustrates an example environment 3900 for implementing devices and methods described herein in accordance with an embodiment. As illustrated, one or more user devices 3902 connect via a network 3904 to an electronic agent (e.g., nicotine) delivery device 3906 as provided herein which can be configured to produce a condensation aerosol comprising a pharmaceutically active agent (e.g., nicotine) as provided herein. The electronic agent (e.g., nicotine) delivery device 3906 can comprise a controller, which can be programmable, as provided herein and the electronic agent (e.g., nicotine) delivery device 3906 can be connected to the network 3904 through the programmable controller. In some cases, the condensation aerosol comprising the pharmaceutically active agent (e.g., nicotine) is produced from a liquid formulation comprising the pharmaceutically active agent (e.g., nicotine) as provided herein. In various embodiments, the user devices 3902 can include any device capable of communicating with the network 3904, such as personal computers, workstations, laptops, smartphones, mobile phones, tablet computing devices, smart TVs, game consoles, internet-connected set up boxes, and the like. In some embodiments, the user devices 3902 can include applications such as web browsers and/or applications (e.g., mobile apps) that are capable of communicating with the electronic agent (e.g., nicotine) delivery device 3906 and/or a system that uses the electronic agent (e.g., nicotine) delivery device 3906. In some cases, the user devices 3902 communicate with the electronic agent (e.g., nicotine) delivery device 3906 via the programmable controller as provided herein. The user can be a patient, and/or a healthcare provider (e.g., physician, physician's assistant, nurse, nurse practitioner, pharmacist or other medical professional). In some cases, a first user uses the device, while a second user uses the other user devices 3902. In some cases, a first user uses the device and the other user devices 3902, while the second user also uses the user devices 3902.

In some embodiments, the electronic agent (e.g., nicotine) delivery device 3906 can communicate with a data store 3908 in order perform the functionalities described herein (e.g., track device usage, adjust dose, frequency of administration, delivery schedule, customize feedback, administer challenge doses, etc.). For example, the data store 3908 can be used to store historical (e.g. user use history, dosage history, delivery schedule history, frequency of administration history, etc.), evaluation rules, and the like.

In some embodiments, the data store 3908, or any other data stores discussed herein, can include one or more data files, databases, (e.g., SQL database), data storage devices (e.g., tape, hard disk, solid-state drive), data storage servers, or the like. The data store 3908 can be connected to the electronic agent (e.g., nicotine) delivery device 3906 locally or remotely via a network. In some embodiments, data store 3908, or any other data stores discussed herein, can comprise one or more storage services provisioned from a "cloud storage" provider, for example, Amazon Simple Storage Service ("Amazon S3"), provided by Amazon.com, Inc. of Seattle, Wash., Google Cloud Storage, provided by Google, Inc. of Mountain View, Calif., and the like.

In various embodiments, the network 3904 can include the Internet, a local area network ("LAN"), a wide area network ("WAN"), a cellular network, wireless network or any other public or private data and/or telecommunication network.

FIG. 40 illustrates example components of an electronic agent (e.g., nicotine) delivery system 4000, in accordance with an embodiment. In this example, the electronic agent (e.g., nicotine) delivery system 4000 includes a data collector 4002 residing on a user or client device 4004. The system further comprises an electronic agent (e.g., nicotine) delivery device 4006, which can be the same as 3906 as depicted in FIG. 39. The electronic agent (e.g., nicotine) delivery device 4006 can comprise a programmable controller, wherein the data collector resides on the programmable controller. The data collector can be implemented as a browser script using JavaScript or any other scripting language. The data collector can be configured to communicate with a web-based backend database. For example, the data collector can be configured to collect parameter information about the electronic agent (e.g., nicotine) delivery device 4006 such as discussed herein and transmit such parameter information to the web-based backend database, for example, using an application programming interface (API) provided by the user device 4004. In some embodiments, the collection and/or communication with the user device 4004 can be triggered by an event on the electronic agent (e.g., nicotine) delivery device 4006. For example, the event can include a click on a portion (e.g., a button or a link) of a user display on the electronic agent (e.g., nicotine) delivery device 4006, use of the delivery device by a user or patient, and the like. The user display can be on the programmable controller as provided herein.

In some embodiments, the electronic agent (e.g., nicotine) delivery device 4006 can be configured to receive parameter information (e.g., dosage, frequency of administration, dosing schedule, etc.) provided by the data collector of the user device and to compare and/or analyze the parameter information received from the data collector of the user device to the parameter information from use of the electronic agent (e.g., nicotine) delivery device 4006. To that end, the electronic agent (e.g., nicotine) delivery device 4006 can utilize an evaluation engine 4008. The evaluation engine 4008 can be configured to analyze the parameter information in order to customize or adjust output parameters of the electronic agent (e.g., nicotine) delivery device 4006. In some embodiments, the evaluation engine 4008 can be implemented using one or more server-side library files. In some embodiments, the evaluation engine 4008 can be implemented using one or more algorithms as provided herein for analyzing the respective parameter.

In some embodiments, customized feedback or a treatment regimen (e.g., agent dosage, frequency of administration and/or delivery schedule) can be evaluated based on some or all of the parameters as provided herein. For example, a lookup table (e.g., stored in memory) can be used to determine the weight values associated with some or all of the parameters. The weight values may or may not be further weighted, combined or otherwise processed to derive a final customized feedback or treatment regimen. In some embodiments, the lookup table and the one or more algorithms for deriving the customized feedback or treatment regimen can be included on one or more rules that are pre-determined based on historical data such as past usage and/or user activities. In some embodiments, analysis of parameter information and/or generation of customized feedback or treatment regimen can be performed in real time or nearly real time with respect to the receipt of the parameter information. In other embodiments, any or all of the above operations may be performed in an asynchronous mode, for example, using batch processing.

In some embodiments, the generated feedback and/or treatment regimen can be stored in a data store 4010. In some embodiments, the data store 4010 can include a memory of a server, one or more data storage device (e.g., SSD, hard disk, taps), or a cloud-based storage service such as discussed in connection with FIG. 39. The data store 4010 may or may not be owned and/or operated by the same as the provider of the electronic agent (e.g., nicotine) delivery device 4006.

FIG. 41 illustrates example components of a computer device 4100 for implementing aspects of devices and methods described herein, in accordance with an embodiment. In another embodiment, the computer device 4100 may be configured to implement a user device such as a user device 3902 discussed in connection with FIG. 39 and/or components or aspects of the electronic agent (e.g., nicotine) delivery device 3906 such as described in connection with FIGS. 39 and 40. In some embodiments, computing device 4100 can include many more components than those shown in FIG. 4100. However, it is not necessary that all of these components be shown in order to disclose an illustrative embodiment.

As shown in FIG. 41, computing device 4100 includes a network interface 4102 for connecting to a network such as discussed above. In some cases, the computing device 4100 is housed on a programmable controller on an electronic agent (e.g., nicotine) delivery device as provided herein. In various embodiments, the computing device 4100 may include one or more network interfaces 4102 for communicating with one or more types of networks such as the Internet, wireless networks, cellular networks, and any other network.

In an embodiment, computing device 4100 also includes one or more processing units 4104, a memory 4106, and an optional display or user interface as provided herein 4108, all interconnected along with the network interface 4102 via a bus 4110. The processing unit(s) 4104 can be capable of executing one or more methods or routines stored in the memory 4106. The display 4108 can be configured to provide a graphical user interface to a user operating the computing device 4100 for receiving user input, displaying output, and/or executing applications. In some cases, such as when the computing device 4100 is a server, the display 4108 may be optional.

The memory 4106 can generally comprise a random access memory ("RAM"), a read only memory ("ROM"), and/or a permanent mass storage device, such as a disk drive. The memory 4106 may store program code for an operating system 4112, one or more agent (e.g., nicotine) delivery routines 4114, and other routines. In various embodiments, the program code can be stored on a computer-readable storage medium, for example, in the form of a computer program comprising a plurality of instructions executable by one or more processors. The computer-readable storage medium can be non-transitory. The one or more agent (e.g., nicotine) delivery routines 4114, when executed, can provide various functionalities associated with the electronic agent (e.g., nicotine) delivery device as described herein.

In some embodiments, the software components discussed above can be loaded into memory 4106 using a drive mechanism associated with a non-transient computer readable storage medium 4118, such as a floppy disc, tape, DVD/CD-ROM drive, memory card, USB flash drive, solid state drive (SSD) or the like. In other embodiments, the software components can alternatively be loaded via the network interface 4102, rather than via a non-transient computer readable storage medium 4118. In an embodiment, the computing device 4100 can also include an optional time keeping device (not shown) for keeping track of the timing of usage of the electronic agent (e.g., nicotine) delivery device.

In some embodiments, the computing device 4100 also communicates via bus 4110 with one or more local or remote databases or data stores such as an online data storage system via the bus 4110 or the network interface 4102. The bus 4110 can comprise a storage area network ("SAN"), a high-speed serial bus, and/or via other suitable communication technology. In some embodiments, such databases or data stores may be integrated as part of the computing device 4100.

Description of the eNT-100 Nicotine Inhaler

The aerosol is created inside the eNT-100 inhaler, which is itself inside a small cylindrical plastic housing that is used to blind the test subject from the test article. The test subject will inhale from a plastic tube that slides over the stainless-steel mouthpiece shown. Inside of the aerosol-generating inhaler is a small heater element that is used to vaporize the nicotine solution under flow conditions that result is a 1.4 to 2.5 micron aerosol particle. The nicotine inhaler further comprises a positive displacement pump to meter out a dose of the nicotine solution onto the heater element.

The eNT-100 is designed to create the aerosol when the inhalation rate reaches 20 lpm (about $3 \times 10^{-4}$ m$^3$/s). At that flow rate the aerosol produced has a particle size of 2.5 micron volume median diameter (VMD) with a GSD of 1.6. The upper end of the inhalation flow rate is determined by the flow rate that can be produced under what is considered an upper limit of vacuum that the human lung can produce by inhalation (13 inches of water is considered that upper limit (about 3235 Pa)). At that vacuum, the inhalation flow rate is 50 lpm (about $8.33 \times 10^{-4}$ m$^3$/s) and the particle size is 1.4 micron VMD with a GSD of 1.2.

The bulk of the aerosol is created within 1 second of the inhaler being breath-activated. Within 1.4 seconds the entire aerosol is created. An estimate of the aerosol produced between the 1 second and the 1.4 second time point is around 5-10% of the total amount of the aerosol. As a result, the bulk of the aerosol is delivered to the respiratory tract in the first ⅓ to ½ of the volume of the total inhalation volume, thereby allowing the aerosol to be "chased" down into the deep lung by the balance of the inhalation.

The eNT-100 system can generate an emitted dose of +1-20% of the dose (or loaded dose). The dose (or loaded dose) can be the amount of nicotine solution pumped onto the heater element prior to the creation of the aerosol and can be +/−2% of the target dose (the label claimed dose or goal dose). The emitted dose can be 92% to 97% of the dose. For example, the amount actually delivered to the lung if the label claim dose is 100 μg would be between 90% and 99%.

While preferred embodiments have been shown and described herein, it will be obvious to those skilled in the art that such embodiments are provided by way of example only. Numerous variations, changes, and substitutions will now occur to those skilled in the art. It should be understood that various alternatives to the embodiments of the invention described herein may be employed. It is intended that the following claims define the scope of the invention and that methods and structures within the scope of these claims and their equivalents be covered thereby.

What is claimed is:

1. A device for generating an aerosol of a liquid, comprising:
    a housing having an inlet and an outlet;
    a liquid container in the housing for containing the liquid;
    an air passageway in the housing from the inlet to the outlet;
    a wire coil in the air passageway, the wire coil concentric with a tube in the air passageway, on one side of the liquid container, with the tube extending horizontally;
    a pump in the housing connected to the liquid container;
    the tube extending from the pump at least partially into the wire coil for pumping liquid from the liquid container onto the wire coil; and
    a sensor in the housing for detecting inhalation, and a battery in the housing electrically connected to the sensor, the pump and the wire coil.

2. The device of claim 1 wherein the liquid in the tube is not vaporized before leaving the tube.

3. The device of claim 1 wherein the liquid is dispensed from the tube onto the wire coil and then vaporized by direct contact with the wire coil.

4. The device of claim 1 wherein electric current flows from the battery directly to the wire coil without flowing through the tube.

5. The device of claim 1 wherein the liquid moves within the tube contacting an internal surface of the tube and not an external surface of the tube.

6. The device of claim 5 wherein the wire coil comprises an open coil having spaces between adjacent loops of the wire coil.

7. The device of claim 5 wherein the pump comprises a positive displacement pump.

8. The device of claim 5 with the tube not extending into the liquid container.

9. The device of claim 8 with the tube positioned to cause liquid to flow along the coil.

10. The device of claim 1 wherein a segment of the passageway is perpendicular to the wire coil.

11. The device of claim 10 with the liquid container containing a liquid comprising nicotine.

12. A device for generating an aerosol of a liquid, comprising:
    an air passageway between an inlet and an outlet in a housing;
    a liquid container for holding a liquid in the housing;
    a wire coil and a rod in the air passageway, on one side of the liquid container, the wire coil in a segment of the air passageway arranged to provide air flow over the wire coil in a direction perpendicular to a longitudinal axis of the rod;
    with the rod within the wire coil and extending from a first end of the wire coil to a second end of the coil, and with the wire coil oriented parallel to a longitudinal axis of the air passageway, with the rod outside of the liquid container and adapted for moving liquid from the liquid container to the wire coil;
    a pump in the housing connected for pumping liquid from the liquid container onto the rod and to the wire coil; and
    a battery in the housing electrically connected to the pump and to the rod which conducts electricity to the wire coil.

13. The device of claim 12 with the liquid container containing a liquid comprising nicotine.

14. The device of claim 12 with the rod positioned to cause liquid to flow along the coil.

15. The device of claim 12 wherein a segment of the rod extending through the wire coil is capable of holding a liquid.

16. The device of claim 12 wherein the wire coil is concentric with the rod.

17. The device of claim 16 wherein the wire coil comprises an open coil having spaces between adjacent loops of the wire coil.

18. A device for generating an aerosol of a liquid, comprising:
    a housing having an inlet and an outlet;
    a liquid container in the housing containing a liquid;
    an air passageway in the housing from the inlet to the outlet;
    a wire coil and a rod in the air passageway, whereby the rod conducts electricity to the wire coil, with the rod extending through the wire coil, and with the rod connected to the liquid container for moving liquid from the liquid container to the wire coil;
    a pump in the housing connected to the liquid container for pumping liquid from the liquid container to the wire coil via the rod; and
    a sensor in the housing for detecting inhalation, and a battery in the housing electrically connected to the sensor, the pump and the wire coil.

* * * * *